(12) United States Patent
Cox et al.

(10) Patent No.: US 11,179,159 B2
(45) Date of Patent: Nov. 23, 2021

(54) METHODS AND DEVICES FOR TREATMENT OF VASCULAR DEFECTS

(71) Applicant: SEQUENT MEDICAL, INC., Aliso Viejo, CA (US)

(72) Inventors: Brian J. Cox, Laguna Niguel, CA (US); Dean Schaefer, Aliso Viejo, CA (US); Robert F. Rosenbluth, Laguna Niguel, CA (US)

(73) Assignee: SEQUENT MEDICAL, INC., Aliso Viejo, CA (US)

( * ) Notice: Subject to any disclaimer, the term of this patent is extended or adjusted under 35 U.S.C. 154(b) by 199 days.

(21) Appl. No.: 15/595,660

(22) Filed: May 15, 2017

(65) Prior Publication Data
US 2017/0245862 A1 Aug. 31, 2017

Related U.S. Application Data

(63) Continuation of application No. 14/869,688, filed on Sep. 29, 2015, now abandoned, which is a
(Continued)

(51) Int. Cl.
*A61F 2/91* (2013.01)
*A61F 2/915* (2013.01)
(Continued)

(52) U.S. Cl.
CPC .... *A61B 17/12031* (2013.01); *A61B 17/1219* (2013.01); *A61B 17/12118* (2013.01);
(Continued)

(58) Field of Classification Search
CPC ........ A61B 17/12118; A61B 17/12172; A61B 17/12177; A61B 17/1219;
(Continued)

(56) References Cited

U.S. PATENT DOCUMENTS 3,874,388 A 4/1975 King et al.
4,282,875 A 8/1981 Serbinenko
(Continued)

FOREIGN PATENT DOCUMENTS

AU 2009242528 3/2016
CA 2722037 10/2009
(Continued)

OTHER PUBLICATIONS

A Complete Microcatheter Portfolio; A Broad Selection of Microcatheters. Boston Scientific Brochure 2007.
(Continued)

*Primary Examiner* — Katrina M Stransky
(74) *Attorney, Agent, or Firm* — One LLP

(57) ABSTRACT

Methods of implanting a device in the lumen of a blood vessel are described. The method includes providing a microcatheter and a device. The device includes a first hub, a second hub, a support structure including a plurality of struts disposed between the first hub and the second hub, and a layer of material disposed over the plurality of struts. The support structure has a low profile, radially constrained state with an elongated tubular configuration suitable for delivery from a microcatheter. The support structure also has an expanded state, a smooth outer surface, and has an axially shortened configuration relative to the radially constrained state. The microcatheter is advanced to a region of interest within the blood vessel. The support structure is advanced through the lumen of and out the distal end of the microcatheter where it expands to the expanded state.

24 Claims, 34 Drawing Sheets

Related U.S. Application Data continuation of application No. 14/044,349, filed on Oct. 2, 2013, now abandoned, which is a continuation of application No. 13/794,473, filed on Mar. 11, 2013, now abandoned, which is a continuation of application No. 13/415,676, filed on Mar. 8, 2012, now abandoned, which is a continuation of application No. 12/602,997, filed as application No. PCT/US2008/065694 on Jun. 3, 2008, now abandoned.

(60) Provisional application No. 61/044,822, filed on Apr. 14, 2008, provisional application No. 60/971,366, filed on Sep. 11, 2007, provisional application No. 60/948,683, filed on Jul. 9, 2007, provisional application No. 60/941,928, filed on Jun. 4, 2007, provisional application No. 60/941,916, filed on Jun. 4, 2007.

(51) Int. Cl.
| | |
|---|---|
| A61F 2/06 | (2013.01) |
| A61F 2/86 | (2013.01) |
| A61F 2/82 | (2013.01) |
| A61F 2/90 | (2013.01) |
| A61F 2/00 | (2006.01) |
| A61B 17/12 | (2006.01) |

(52) U.S. Cl.
CPC .. *A61B 17/12172* (2013.01); *A61B 17/12177* (2013.01); *A61B 17/12181* (2013.01); *A61F 2/06* (2013.01); *A61F 2/82* (2013.01); *A61F 2/86* (2013.01); *A61F 2/90* (2013.01); *A61F 2/91* (2013.01); *A61F 2/915* (2013.01); *A61B 17/12022* (2013.01); *A61B 2017/1205* (2013.01); *A61F 2/0077* (2013.01); *A61F 2002/823* (2013.01); *A61F 2002/9155* (2013.01); *A61F 2002/91558* (2013.01); *A61F 2210/0076* (2013.01); *A61F 2220/005* (2013.01); *A61F 2220/0075* (2013.01); *A61F 2230/006* (2013.01); *A61F 2230/0054* (2013.01); *A61F 2230/0069* (2013.01); *A61F 2230/0076* (2013.01)

(58) Field of Classification Search
CPC ........ A61B 17/12031; A61B 17/12181; A61B 17/12022; A61F 2/06; A61F 2/82; A61F 2/90; A61F 2/91; A61F 2/915; A61F 2/86
See application file for complete search history.

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Molgaard-Nielsen |
| 4,675,361 A | 6/1987 | Ward |
| 4,729,278 A | 3/1988 | Graeff |
| 4,998,539 A | 3/1991 | Delsanti |
| 5,061,275 A | 10/1991 | Wallsten et al. |
| 5,071,407 A | 12/1991 | Termin et al. |
| 5,108,407 A | 4/1992 | Geremia et al. |
| 5,122,136 A | 6/1992 | Guglielmi et al. |
| 5,154,705 A | 10/1992 | Fleischhacker et al. |
| 5,158,545 A | 10/1992 | Trudell et al. |
| 5,165,421 A | 11/1992 | Fleischhacker et al. |
| 5,263,963 A | 11/1993 | Garrison |
| 5,334,210 A | 8/1994 | Gianturco |
| 5,378,239 A | 1/1995 | Termin |
| 5,536,247 A | 7/1996 | Thornton |
| 5,562,725 A | 10/1996 | Schmitt et al. |
| 5,569,245 A | 10/1996 | Guglielmi et al. |
| 5,578,074 A | 11/1996 | Mirigian |
| 5,591,222 A | 1/1997 | Susawa et al. |
| 5,601,595 A | 2/1997 | Smith |
| 5,630,840 A | 5/1997 | Mayer |
| D380,266 S | 6/1997 | Boatman et al. |
| 5,645,559 A | 7/1997 | Hachtman et al. |
| 5,725,552 A * | 3/1998 | Kotula .................. A61F 2/01 |
| | | 606/213 |
| 5,725,570 A | 3/1998 | Heath |
| 5,733,294 A | 3/1998 | Forber |
| 5,749,883 A | 5/1998 | Halpern |
| 5,759,161 A | 6/1998 | Ogawa |
| 5,766,219 A | 6/1998 | Horton |
| 5,846,261 A | 12/1998 | Kotula et al. |
| 5,873,907 A | 2/1999 | Frantzen |
| 5,907,893 A | 6/1999 | Zadno-Azizi |
| 5,916,235 A | 6/1999 | Guglielmi |
| 5,925,060 A | 7/1999 | Forber |
| 5,927,345 A | 7/1999 | Samson |
| 5,928,260 A | 7/1999 | Chin et al. |
| 5,935,148 A * | 8/1999 | Villar ............... A61B 17/12022 |
| | | 606/213 |
| 5,944,733 A | 8/1999 | Engelson |
| 5,944,738 A | 8/1999 | Amplatz |
| 5,951,599 A | 9/1999 | McCrory |
| 5,964,797 A | 10/1999 | Ho |
| 5,980,554 A | 11/1999 | Lenker et al. |
| 5,984,929 A | 11/1999 | Bashiri et al. |
| 5,989,242 A | 11/1999 | Saadat et al. |
| 6,033,423 A | 3/2000 | Ken et al. |
| 6,063,070 A | 5/2000 | Eder |
| 6,063,104 A | 5/2000 | Villar et al. |
| 6,086,577 A | 7/2000 | Ken et al. |
| 6,093,199 A | 7/2000 | Brown et al. |
| 6,123,715 A | 9/2000 | Amplatz |
| 6,139,564 A | 10/2000 | Teoh et al. |
| 6,142,975 A | 11/2000 | Jalisi et al. |
| 6,152,144 A | 11/2000 | Lesh et al. |
| 6,159,206 A | 12/2000 | Ogawa |
| 6,166,061 A | 12/2000 | Wallace et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,190,402 B1 | 2/2001 | Horton et al. |
| 6,193,708 B1 | 2/2001 | Ken et al. |
| 6,203,779 B1 | 3/2001 | Ricci et al. |
| 6,221,086 B1 | 4/2001 | Forber |
| 6,277,126 B1 | 8/2001 | Barry et al. |
| 6,290,721 B1 | 9/2001 | Heath |
| 6,315,709 B1 | 11/2001 | Garibaldi et al. |
| 6,325,815 B1 | 12/2001 | Kusleika |
| 6,342,068 B1 | 1/2002 | Thompson |
| 6,344,048 B1 | 2/2002 | Chin et al. |
| 6,346,117 B1 | 2/2002 | Greenhalgh |
| 6,350,270 B1 | 2/2002 | Roue |
| 6,368,338 B1 | 4/2002 | Konya |
| 6,368,339 B1 | 4/2002 | Amplatz |
| 6,375,668 B1 | 4/2002 | Gifford |
| 6,375,670 B1 | 4/2002 | Greenhalgh |
| 6,383,174 B1 | 5/2002 | Eder |
| 6,391,037 B1 | 5/2002 | Greenhalgh |
| 6,425,914 B1 | 7/2002 | Wallace et al. |
| 6,428,558 B1 * | 8/2002 | Jones ............... A61B 17/12022 |
| | | 606/151 |
| 6,447,531 B1 | 9/2002 | Amplatz |
| 6,454,780 B1 | 9/2002 | Wallace |
| 6,461,370 B1 | 10/2002 | Gray et al. |
| 6,463,317 B1 | 10/2002 | Kucharczyk |
| 6,468,266 B1 | 10/2002 | Bashir et al. |
| 6,478,773 B1 | 11/2002 | Gandhi et al. |
| 6,500,149 B2 | 12/2002 | Gandhi et al. |
| 6,506,204 B2 | 1/2003 | Mazzocchi |
| 6,511,468 B1 | 1/2003 | Cragg et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 * | 7/2003 | Palmer ............. A61B 17/12022 |
| | | 606/200 |

(56) References Cited

U.S. PATENT DOCUMENTS

| | | | |
|---|---|---|---|
| 6,599,308 B2 | 7/2003 | Amplatz |
| 6,605,102 B1 | 8/2003 | Mazzocchi et al. |
| 6,605,111 B2 | 8/2003 | Bose et al. |
| 6,607,539 B1 | 8/2003 | Hayashi et al. |
| 6,613,074 B1 | 9/2003 | Mitelberg |
| 6,632,241 B1 | 10/2003 | Hancock |
| 6,635,068 B1 | 10/2003 | Dubrul et al. |
| 6,638,257 B2 | 10/2003 | Amplatz |
| 6,652,556 B1 | 11/2003 | Van Tassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,150 B1 | 2/2004 | Van Tassel |
| 6,689,486 B2 | 2/2004 | Ho et al. |
| 6,719,778 B1 | 4/2004 | Van Tassel et al. |
| 6,730,119 B1 | 5/2004 | Smalling |
| 6,743,236 B2 | 6/2004 | Barry et al. |
| 6,743,251 B1 | 6/2004 | Eder |
| 6,746,468 B1 | 6/2004 | Sepetka et al. |
| 6,746,890 B2 | 6/2004 | Gupta et al. |
| 6,752,826 B2 | 6/2004 | Holloway et al. |
| 6,780,196 B2 | 8/2004 | Chin et al. |
| 6,811,560 B2 | 11/2004 | Jones et al. |
| 6,818,006 B2 | 11/2004 | Douk et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,936,055 B1 | 8/2005 | Ken et al. |
| 6,940,209 B2 | 9/2005 | Henderson |
| 6,953,472 B2 | 10/2005 | Palmer et al. |
| 6,953,473 B2 | 10/2005 | Porter |
| 6,966,892 B2 | 11/2005 | Gandhi et al. |
| 6,994,092 B2 * | 2/2006 | van der Burg ..... A61B 17/0057 |
| | | | 128/887 |
| 7,001,409 B2 | 2/2006 | Amplatz |
| 7,004,962 B2 | 2/2006 | Stinson |
| 7,011,671 B2 | 3/2006 | Welch |
| 7,044,958 B2 | 5/2006 | Douk et al. |
| 7,052,513 B2 | 5/2006 | Thompson |
| 7,083,632 B2 | 8/2006 | Avellanet et al. |
| 7,101,390 B2 | 9/2006 | Nelson |
| 7,122,043 B2 | 10/2006 | Greenhalgh et al. |
| 7,128,736 B1 | 10/2006 | Abrams et al. |
| 7,179,276 B2 | 2/2007 | Barry et al. |
| 7,182,774 B2 | 2/2007 | Barry et al. |
| 7,195,636 B2 | 3/2007 | Avellanet et al. |
| 7,198,613 B2 | 4/2007 | Gandhi et al. |
| 7,201,918 B2 | 4/2007 | Cruise |
| 7,229,454 B2 | 6/2007 | Tran |
| 7,229,461 B2 | 7/2007 | Chin et al. |
| 7,275,471 B2 | 10/2007 | Nishri et al. |
| 7,326,225 B2 | 2/2008 | Ferrera et al. |
| 7,329,279 B2 | 2/2008 | Haug et al. |
| 7,331,980 B2 | 2/2008 | Dubrul |
| 7,410,482 B2 | 8/2008 | Murphy |
| 7,419,503 B2 | 9/2008 | Pulnev et al. |
| 7,490,396 B2 | 2/2009 | Bradley |
| 7,524,319 B2 | 4/2009 | Dubrul |
| 7,569,066 B2 | 8/2009 | Gerberding |
| 7,573,382 B2 | 8/2009 | Choubey et al. |
| 7,575,582 B2 | 8/2009 | Gandhi et al. |
| 7,578,826 B2 | 8/2009 | Gandhi et al. |
| 7,597,704 B2 | 10/2009 | Frazier et al. |
| 7,648,532 B2 | 1/2010 | Greenhalgh et al. |
| 7,695,488 B2 | 4/2010 | Berenstein |
| 7,722,637 B2 | 5/2010 | Barry et al. |
| 7,745,732 B2 | 6/2010 | Michael et al. |
| 7,806,919 B2 | 10/2010 | Bloom et al. |
| 7,862,577 B2 | 1/2011 | Gray et al. |
| 7,942,925 B2 | 5/2011 | Yodaf |
| 7,989,703 B2 | 8/2011 | Schaffer |
| 8,043,326 B2 | 10/2011 | Hancock |
| 8,043,329 B2 | 10/2011 | Khairkhahan |
| 8,066,757 B2 | 11/2011 | Ferrera et al. |
| 8,142,456 B2 | 3/2012 | Rosqueta et al. |
| 8,182,506 B2 | 5/2012 | Fitz et al. |
| 8,192,480 B2 | 6/2012 | Tieu et al. |
| 8,313,505 B2 | 11/2012 | Amplatz et al. |
| 8,398,670 B2 | 3/2013 | Amplatz |
| 8,430,012 B1 | 4/2013 | Marchand |
| 8,506,619 B2 | 8/2013 | Ortiz et al. |
| 8,551,132 B2 | 10/2013 | Eskridge et al. |
| 8,597,320 B2 | 12/2013 | Sepetka et al. |
| 8,597,323 B1 | 12/2013 | Plaza et al. |
| 8,715,338 B2 | 5/2014 | Frid |
| 8,728,117 B1 | 5/2014 | Janardhan et al. |
| 8,758,395 B2 | 6/2014 | Kleshinski et al. |
| 8,840,735 B2 | 9/2014 | Schaffer |
| 8,845,679 B1 | 9/2014 | Janardhan et al. |
| 9,078,658 B2 | 7/2015 | Hewitt et al. |
| 9,198,668 B2 | 12/2015 | Theobald et al. |
| 9,198,670 B2 | 12/2015 | Hewitt et al. |
| 9,259,337 B2 | 2/2016 | Cox et al. |
| 9,272,323 B2 | 3/2016 | Schaffer |
| 9,295,473 B2 | 3/2016 | Hewitt et al. |
| 9,492,174 B2 | 11/2016 | Hewitt et al. |
| 9,504,588 B2 | 11/2016 | Sadasivan et al. |
| 2001/0031981 A1 | 10/2001 | Evans et al. |
| 2002/0065552 A1 | 5/2002 | Jayaraman et al. |
| 2002/0103542 A1 | 8/2002 | Bilbo |
| 2002/0143349 A1 | 10/2002 | Gifford, III et al. |
| 2002/0143361 A1 | 10/2002 | Douk et al. |
| 2002/0156499 A1 | 10/2002 | Konya et al. |
| 2002/0169473 A1 | 11/2002 | Sepetka et al. |
| 2002/0183787 A1 | 12/2002 | Wahr et al. |
| 2002/0187288 A1 | 12/2002 | Lim et al. |
| 2003/0012816 A1 | 1/2003 | West et al. |
| 2003/0028209 A1 * | 2/2003 | Teoh ................ A61B 17/12172 |
| | | | 606/191 |
| 2003/0171739 A1 | 9/2003 | Murphy et al. |
| 2003/0171774 A1 | 9/2003 | Freudenthal et al. |
| 2003/0181942 A1 | 9/2003 | Sutton et al. |
| 2003/0187473 A1 | 10/2003 | Berenstein et al. |
| 2003/0199913 A1 | 10/2003 | Dubrul et al. |
| 2004/0059370 A1 | 3/2004 | Green, Jr. et al. |
| 2004/0098027 A1 | 5/2004 | Tech et al. |
| 2004/0111147 A1 | 6/2004 | Rabkin et al. |
| 2004/0122367 A1 | 6/2004 | Van Tassel et al. |
| 2004/0143239 A1 | 7/2004 | Zhou et al. |
| 2004/0158311 A1 | 8/2004 | Berhow |
| 2004/0172053 A1 | 9/2004 | Barry et al. |
| 2004/0186562 A1 | 9/2004 | Cox |
| 2004/0193206 A1 | 9/2004 | Gerberding et al. |
| 2004/0193208 A1 | 9/2004 | Talpade et al. |
| 2004/0220563 A1 | 11/2004 | Eder |
| 2004/0260333 A1 | 12/2004 | Dubrul et al. |
| 2005/0021075 A1 | 1/2005 | Bonnette et al. |
| 2005/0033408 A1 | 2/2005 | Jones et al. |
| 2005/0053782 A1 | 3/2005 | Sen et al. |
| 2005/0096728 A1 | 5/2005 | Ramer |
| 2005/0112349 A1 | 5/2005 | Laurencin et al. |
| 2005/0113861 A1 * | 5/2005 | Corcoran ......... A61B 17/12022 |
| | | | 606/200 |
| 2005/0113868 A1 | 5/2005 | Devellian et al. |
| 2005/0119684 A1 | 6/2005 | Guterman et al. |
| 2005/0133046 A1 | 6/2005 | Becker et al. |
| 2005/0149173 A1 | 7/2005 | Hunter et al. |
| 2005/0216052 A1 | 9/2005 | Mazzocchi et al. |
| 2005/0222489 A1 | 10/2005 | Rahdert et al. |
| 2005/0228422 A1 | 10/2005 | Machold et al. |
| 2005/0228434 A1 | 10/2005 | Amplatz et al. |
| 2005/0267516 A1 | 12/2005 | Soleimani et al. |
| 2005/0277978 A1 | 12/2005 | Greenhalgh |
| 2006/0009798 A1 | 1/2006 | Callister et al. |
| 2006/0009799 A1 | 1/2006 | Kleshinski et al. |
| 2006/0009800 A1 | 1/2006 | Christianson et al. |
| 2006/0052815 A1 | 3/2006 | Fitz et al. |
| 2006/0052816 A1 | 3/2006 | Bates et al. |
| 2006/0064151 A1 | 3/2006 | Guterman et al. |
| 2006/0083721 A1 | 4/2006 | Cohen et al. |
| 2006/0116708 A1 | 6/2006 | Ogawa et al. |
| 2006/0135947 A1 | 6/2006 | Soltesz et al. |
| 2006/0155323 A1 | 7/2006 | Porter et al. |
| 2006/0178694 A1 | 8/2006 | Greenhalgh et al. |

(56) References Cited

U.S. PATENT DOCUMENTS

| | | |
|---|---|---|
| 2006/0200192 A1 | 9/2006 | Fitz et al. |
| 2006/0200234 A1 | 9/2006 | Hines |
| 2006/0212055 A1 | 9/2006 | Karabey et al. |
| 2006/0217799 A1 | 9/2006 | Mailander et al. |
| 2006/0235464 A1 | 10/2006 | Avellanet et al. |
| 2006/0247680 A1 | 11/2006 | Amplatz et al. |
| 2006/0252984 A1 | 11/2006 | Rahdert et al. |
| 2006/0253149 A1 | 11/2006 | Gandhi et al. |
| 2006/0271086 A1 | 11/2006 | Ramzipoor et al. |
| 2007/0021816 A1 | 1/2007 | Rudin |
| 2007/0031584 A1 | 2/2007 | Roth |
| 2007/0061006 A1 | 3/2007 | Desatnik et al. |
| 2007/0088387 A1 | 4/2007 | Eskridge et al. |
| 2007/0100419 A1 | 5/2007 | Licata et al. |
| 2007/0106323 A1 | 5/2007 | Barry et al. |
| 2007/0112380 A1 | 5/2007 | Figulla |
| 2007/0142906 A1 | 6/2007 | Figulla |
| 2007/0144124 A1 | 6/2007 | Schewe et al. |
| 2007/0167911 A1 | 7/2007 | Gandhi et al. |
| 2007/0167980 A1 | 7/2007 | Figulla et al. |
| 2007/0173028 A1 | 7/2007 | Morsi |
| 2007/0203062 A1 | 8/2007 | Ellis-Behnke et al. |
| 2007/0208373 A1 | 9/2007 | Zaver et al. |
| 2007/0208376 A1 | 9/2007 | Meng |
| 2007/0225760 A1 | 9/2007 | Moszner et al. |
| 2007/0233186 A1 | 10/2007 | Meng |
| 2007/0255388 A1 | 11/2007 | Rudakov et al. |
| 2007/0265656 A1 | 11/2007 | Amplatz et al. |
| 2007/0288083 A1 | 12/2007 | Hines |
| 2008/0033341 A1 | 2/2008 | Grad |
| 2008/0033366 A1 | 2/2008 | Matson |
| 2008/0033475 A1 | 2/2008 | Meng |
| 2008/0033478 A1 | 2/2008 | Meng |
| 2008/0097495 A1* | 4/2008 | Feller, III ......... A61B 17/12022 606/157 |
| 2008/0119886 A1 | 5/2008 | Greenhalgh et al. |
| 2008/0161936 A1* | 7/2008 | Feller .............. A61B 17/12022 623/23.76 |
| 2008/0195139 A1 | 8/2008 | Donald et al. |
| 2008/0200945 A1 | 8/2008 | Amplatz et al. |
| 2008/0221600 A1 | 9/2008 | Dieck et al. |
| 2008/0228215 A1 | 9/2008 | Strauss et al. |
| 2009/0025820 A1 | 1/2009 | Adams |
| 2009/0062812 A1 | 3/2009 | Fitz et al. |
| 2009/0062834 A1 | 3/2009 | Moftakhar |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112305 A1 | 4/2009 | Goldmann et al. |
| 2009/0132024 A1 | 5/2009 | Berkhoff |
| 2009/0227976 A1 | 9/2009 | Calabria |
| 2009/0275974 A1 | 11/2009 | Marchand |
| 2009/0287291 A1 | 11/2009 | Becking et al. |
| 2009/0287294 A1 | 11/2009 | Rosqueta et al. |
| 2009/0318948 A1 | 12/2009 | Linder et al. |
| 2010/0023048 A1 | 1/2010 | Mach |
| 2010/0069948 A1 | 3/2010 | Veznedaroqlu |
| 2010/0094409 A1 | 4/2010 | Barker et al. |
| 2010/0106235 A1 | 4/2010 | Kariniemi et al. |
| 2011/0022149 A1 | 1/2011 | Cox |
| 2011/0029008 A1 | 2/2011 | Gesswein |
| 2011/0046658 A1 | 2/2011 | Connor et al. |
| 2011/0046719 A1 | 2/2011 | Frid |
| 2011/0054515 A1 | 3/2011 | Bridgeman |
| 2011/0082493 A1 | 4/2011 | Samson et al. |
| 2011/0152823 A1 | 6/2011 | Mohiuddin |
| 2011/0152993 A1 | 6/2011 | Marchand |
| 2011/0202085 A1 | 8/2011 | Loganathan et al. |
| 2011/0208227 A1 | 8/2011 | Becking |
| 2011/0208233 A1 | 8/2011 | McGuckin |
| 2011/0224776 A1 | 9/2011 | Sepekta et al. |
| 2011/0295298 A1 | 12/2011 | Moszner |
| 2011/0319926 A1 | 12/2011 | Becking |
| 2012/0143237 A1 | 6/2012 | Cam |
| 2012/0165919 A1 | 6/2012 | Cox |
| 2012/0197283 A1 | 8/2012 | Marchand et al. |
| 2012/0271337 A1 | 10/2012 | Figulla et al. |
| 2012/0283768 A1 | 11/2012 | Cox |
| 2013/0116722 A1 | 5/2013 | Aboytes et al. |
| 2013/0123830 A1 | 5/2013 | Becking et al. |
| 2013/0211495 A1 | 8/2013 | Halden et al. |
| 2013/0245667 A1 | 9/2013 | Marchand et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2014/0005713 A1 | 1/2014 | Bowman |
| 2014/0005714 A1 | 1/2014 | Quick et al. |
| 2014/0018841 A1 | 1/2014 | Peiffer |
| 2014/0052233 A1 | 2/2014 | Cox et al. |
| 2014/0074151 A1 | 3/2014 | Tischler et al. |
| 2014/0135734 A1 | 5/2014 | Dakin et al. |
| 2014/0135817 A1 | 5/2014 | Tischler et al. |
| 2015/0182674 A1 | 7/2015 | Schaffer |
| 2016/0030052 A1 | 2/2016 | Cragg et al. |
| 2016/0192941 A1 | 7/2016 | Hewitt et al. |
| 2016/0262769 A1 | 9/2016 | Cragg et al. |
| 2016/0324528 A1 | 11/2016 | Hebert et al. |
| 2016/0335757 A1 | 11/2016 | Florent et al. |
| 2017/0245862 A1 | 8/2017 | Cox et al. |

FOREIGN PATENT DOCUMENTS

| | | |
|---|---|---|
| CN | 106974691 | 7/2017 |
| EP | 0706876 | 7/2000 |
| EP | 0808138 | 5/2005 |
| EP | 1576929 | 9/2005 |
| EP | 1844717 | 10/2007 |
| EP | 1923019 | 5/2008 |
| EP | 2055263 | 6/2009 |
| EP | 2258275 | 12/2011 |
| EP | 2157937 | 3/2017 |
| FR | 2333169 | 6/1977 |
| JP | 52141092 | 11/1977 |
| JP | H4-47415 | 4/1992 |
| JP | 6124952 | 4/2017 |
| WO | WO 95/30384 A2 | 11/1995 |
| WO | WO 1996/01591 | 1/1996 |
| WO | WO 1997/26939 | 7/1997 |
| WO | WO 1999/03404 | 1/1999 |
| WO | WO 1999/05977 | 2/1999 |
| WO | WO 1999/62432 | 12/1999 |
| WO | WO 01/45571 | 6/2001 |
| WO | WO 2001/93782 | 12/2001 |
| WO | WO 2002/00139 | 1/2002 |
| WO | WO 2003/011151 | 2/2003 |
| WO | WO 2003/032818 | 4/2003 |
| WO | WO 2003/063732 | 8/2003 |
| WO | WO 2004/047649 | 6/2004 |
| WO | WO 2005/117718 | 6/2004 |
| WO | WO 2004/093742 | 11/2004 |
| WO | WO 2006/026744 | 3/2006 |
| WO | WO 2006/055683 | 5/2006 |
| WO | WO 2007/096183 | 8/2007 |
| WO | WO 2008/151204 | 12/2008 |
| WO | WO 2009/121006 | 1/2009 |
| WO | WO 2009/036219 | 3/2009 |
| WO | WO 2009/126747 | 10/2009 |
| WO | WO 2009/132045 | 10/2009 |
| WO | WO 2009/134337 | 11/2009 |
| WO | WO 2009/135166 | 11/2009 |
| WO | WO 2011/057002 | 5/2011 |
| WO | WO 2013/102848 A2 | 7/2013 |
| WO | WO 2014/169261 | 10/2014 |
| WO | WO 2015/171268 | 11/2015 |
| WO | WO 2015/192019 | 12/2015 |

OTHER PUBLICATIONS

Allen et al., "Micromachine Wedge Stepping Motor," pp. 1-6, Nov. 12-20, 1998 ASME International Mechanical Engineering Congress, Anaheim, CA.

(56) References Cited

OTHER PUBLICATIONS

Altes et al., "Creation of Saccular Aneurysms in the Rabbit: A model Suitable for Testing Endovascular Devices," American Roentgen Ray Society, Feb. 2000.

Ansari et al., "Thrombosis of a Fusiform Intracranial Aneurysm Induced by Overlapping Neuroform Stents: Case Report," *Neurosurgery*,E950-E951 vol. 60, No. 5, May 2007.

Alritech Press Release, Minneapolis, Jun. 18, 2007 "Atritech Announces Intellectual Property Acquisition, Transaction Establishes Company as leader in Left Atrial Appendage Market."

Caroff, J. et al., "Woven Endobridge (WEB) Device for endovascular treatment of ruptured intracranial wide-neck aneurysms: a single-center experience," *Neuroradiology*, 56(9):755-761 (Sep. 2014).

Caroff, J. et al., "Role of C-Arm VasoCT in the Use of Endovascular WEB Flow Disruption in Intracranial Aneurysm Treatment," *AJNR Am. J. Neuroradiol.* 35(7): 1353-1357 (Jul. 2014).

Colla, R. et al., "Treatment of Wide-Neck Basilar Tip Aneurysms Using the Web II Device," *The Neuroradiology Journal* 26(6):669-677 (Dec. 2013).

De Backer, O. et al., "Percutaneous left atrial appendage occlusion for stroke prevention in atrial fibrillation: an update," *Open Heart*, 4:1-14 (2013).

Ding, Y.H. et al., "The Woven EndoBridge: A New Aneurysm Occlusion Device," *AJNR Am. J. Neruradiol.* 32:607-611 (Mar. 2011).

Duerig, T.W., "The Use of Superelasticity in Modern Medicine," MRS Bulletin, pp. 101-104 (Feb. 2002).

Fiorella, D. et al., "Interobserver variability in the assessment of aneurysm occlusion with the WEB aneurysm embolization system," *J. NeuroIntervent. Surg.* Jul. 1, 2014, pii: neurintsurg—2014-011251. doi: 10.1136/neurintsurg-2014-011251 [Epub ahead of print].

Fort Wayne Metals HHS Tube brochure, p. 28-29 (2009), Fort Wayne, Indiana, www.oldsite.fwmetals.com.

Grabenwoger et al., "Endotnelialization of Biosynthetic vascular Prosthesis After Laser Perforation," *Ann Thorac Surg*, 66:S110-S114(1 998).

Guider Softip XF Guide Catheters Brochure, Boston Scientific Corporation 2004.

Gupta et al., "Nitinol Thin Film three Dimensional Devices-Fabrication and Applications," From: SMST-2003: Proceedings of the international Conference on Shape Memory and Superelastic Technologies Published: 2004.

Hill et al., "Initial Results of the AMPLATZER® Vascular Plug in the treatment of Congenital Heart Disease," Technology and Services, *Business Briefing: US Cardiology*, pp. 1-3 (2004).

Jeffree et al., "The Porus, Guidewire-Directed, Detachable Aneurysm Liner: A New Concept in the Endovascular Treatment of Intracranial Aneurysms," *AJNR Am J Neuradiol* 20:774-779 (May 1999).

Kallmes et al., "A New Endoluminal, Flow-Disrupting Device for Treatment of Saccular Eneurysms," *Stroke*, Journal of the American Heart Association 38:1-7 (2007).

Klisch, J. et al., "The Woven EndoBridge Cerebral Aneurysm Embolization Device (WEB II): initial clinical experience," *Neuroradiology* 53:599-607 (2011).

Kónya, A. and Wright , K.C., "Preliminary Results with a New Vascular Basket Occluder in Swine," *JVIR*, 10(8)11043-1049 (1999).

Kwon et al., "Preliminary Results of the Luna Aneurysm Embolization System in a Rabbit Model: A New Intrasaccular Aneurysm Occlusion Device." *AJNR Am J Neuroradiol*, 32:602-606 (Mar. 2011).

Lendlein, A. and Kelch, S., "Shape-Memory Polymers," *Angew. Chem. Int. Ed.*, 41:2034-2057 (2002).

Lendlein, A. and Langer, R., "Biodegradable. Elastic Shape—Memory Polymers for Potential Biomedicai Applications," *Science* 296:1673-1676 (May 31, 2002).

Lieber, B.B. et al., "The Role of Blood Impulse In Cerebral Aneurysm Coil Compaction: Effect of Aneurysm Neck Size," IMECE2003-43099, Proceedings of IMECE'03, 2003 ASME international Mechanical Engineering Congress, Washington, D.C. (Nov. 15-21, 2003).

Liu, C. et al., "Review of progress in shape—memory polymers," *J. Mater. Chem.* 17:1543-1558(2007).

Lubicz, B. et al., "WEB Device for Endovascular Treatment of Wide-Neck Bifurcation Aneurysms," *AJNR Am. J. Neuroradiol.* 34(6):1209-1214 (Jun.-Jul. 2013).

Lubicz, B. et al., "WEB-DL Endovascular Treatment of Wide-Neck Bifurcation Aneurysms: Short- and Midterm Results in a European Study," *AJNR Am. J. Neuroradiol.*35(3):432-438 (Mar. 2014). doi: 10.3174/ajnr.A3869. Epub Jan. 23, 2014.

Major, S. and Hubalovsky, S., "Life of Nitinol Drawn Filed Wires with Ag or Au Core for Medical Application," *International Journal of Mechanics* 2(7):73-80 (2013).

Matinlinna et al., "An Introduction to Silanes and Their Clinical Applications in Dentistry," *The International Journal of Prosthodontics*, 17(2):155-164 (2004).

Mine et al., "Intrasaccular flow-diversion for treatment of intracranial aneurysms: the Woven EndoBridge," *Expert Rev. Med. Devices*11(3): 315-325 (May 2014). doi: 10.1586/17434440.2014.907741. Epub Apr. 2, 2014.

Nakayama et al., "Development of Microporous Covered Stents: Geometrical Design of the Luminal Surface." *The International Journal of Artificial Organs*, 28(6):600-608 (2005).

Nemat-Nasser, S. and Guo, W.-G, "Superelastic and cyclic response of NiTi SMA at various strain rates and temperatures," *Mechanics of Materials* 38:463-474 (2006).

Nishi et al., "Embolization of experimental aneurysms using a heparin-loaded stent graft with micropores," *Cardiovascular Radiation Medicine* 4:29-33 (2003).

Nishi et al., "Occlusion of Experimental Aneurysms with Heparin-Loaded, Microporous Stent Grafts," *Neurosurgery* 53(6)1397-1405 (Dec. 2003).

Papagiannaki, C. et al., "WEB Intrasaccular Flow Disruptor—Prospective, Multicenter Experience in 83 Patients with 85 Aneurysms," *AJNR Am. J. Neuroradiol.* 35(11):2106-2111 (Nov.-Dec. 2014). 35(11):2106-11. doi: 10.3174/ajnr.A4028. Epub Jul. 3, 2014.

Park, J. et al., "Percutaneous Left Atrial Appendage Transcatheter Occlusion (PLAATO) for Stroke Prevention in Atrial Fibrillation: 2-Year Outcome," *J Invasive. Cardiol.*, 21(9)1446-450 (2009).

Pelton, A.R. et al., "Optimisation of processing and properties of medical grade Nitinol wire," *Min. Invas. Ther. & Allied Technol.* 9(1)1107-118 (2000).

Pham, Q. et al., Electrospinning of Polymeric Nanofibers for Tissue Engineering Applications: A Review, *Tissue Engr* 12(5):1197-1211 (2006).

Pierot, L. et al., "Intrasaccular Flow-Disruption Treatment of intracranial Aneurysms: Preliminary Results of a Multicenter Clinical Study," *AJNR Am J Neuroradiol*. 33(7):1232-1238 (Aug. 2012). doi: 10.3174/ ajnr,A3191. Epub Jun. 7, 2012.

Pierot, L. et al., "Endovascular WEB Flow Disruption in Middle Cerebral Artery Aneurysms: Preliminary Feasibility, Clinical, and Anatomical Results in a Multicenter Study," *Neurosurgery* 73(1):27-35 (Jul. 2013).

Pierot, L. et al., "Role, safety, and efficacy of WEB flow disruption: a review," *EJMINT* Invited Review, 2014: 1419000139 (May 8, 2014).

Peirot, L. et al., "WEB Treatment of intracranial Aneurysms: Feasiblity, Complications, and 1-Month Safety Results with the Web DL and Web SL/SLS in the French Observatory," *AJNR Am J Neuroradiol*. Feb. 5, 2015 [Epub ehead of print].

Romero, J. et al. "Left Atrial Appendage Closure Devices." *Clinical Medicine Insights: Cardiology*, 8:45-52 (2014).

Rottiers, W. et al., "Shape Memory Materials and their applications," In Korolev's readings: conference proceedings, pp. 250-251 (2011).

Salamat et al., "Experimental Evaluation of a New Transcatheter Vascular Embolization Device in the Swine Model," *J Vasc Interv Radiol*, 12:301-311 (2002).

Schaffer, J.E. and Gordon, R., "Engineering Characteristics of Drawn Filled Nitinol Tube," SMST—2003: Proceedings of the

(56) References Cited

OTHER PUBLICATIONS

International Conference on Shape Memory and Superelastic Technologies (ASM International), p. 109-118 (2004).
Schmitz-Rode, T. et al., "Self-expandable spindle for transcatheter vascular occlusion: in vivo experiments. Work in progress." *Radiology* 188:95-100 (Jul. 1993).
Simgen, A. et al., "Evaluation of a newly designed flow diverter for the treatment of intracranial aneurysms in an elastase-induced aneurysm model, in New Zealand white rabbits," *Neuroradiology* 56:129-137 (2014).
Spelle, L. and Liebig, T., "Letter to the Editor," *Neuroradiol J.* Jun. 2014; 27(3)1369. doi: 10.15274/NRJ-2014-10048. Epub Jun. 17, 2014.
Stoeckel, D. et al., "Self-expanding nitinol stents: material and design considerations," *Eur. Radiol.* 14:292-301 (2004).
Turk, A. et al., "Evaluation of the TriSpan Neck Bridge Device for the Treatment of Wide-Necked Aneurysms: An Experimental Study in Canines, Editorial Comment: An Experimental Study in Canines," *Stroke* 32:492-497 (Feb. 2001).
Wallner, A.K. et al., "Coiling after Treatment with the Woven EndoBridge Cerebral Aneurysm Embolization Device," *Interventional Neuroradiology* 18:208-212 (2012).
Yeow, W.L. and Kar, S., Device- and LAA-Specific Characteristics for Successful LAA Closures: Tips and Tricks, *Intervent. Cardiol. Clin.*, 3:239-254 (2014).
Zimmermann et al., "Patent Foramen Oval Closure With the SeptRX Device, Initial Experience with the First "In-Tunnel" Device," *JACC Cardiovascular Interventions* vol. 3, No. 9., 2010.
International Preliminary Report on Patentability dated Dec. 7, 2009 for International Application No. PCT/US2008/065694 filed on Jun. 3, 2008 and published as WO/2008/151204 dated Dec. 11, 2008.
International Search Report and Written Opinion dated Oct. 31, 2008 for International Application No. PCT/US2008/065694 filed on Jun. 3, 2008.
International Preliminary Report on Patentability dated Nov. 2, 2010 for International Application No. PCT/US2009/042592 filed on May 1, 2009 and published as: WO/2009/135166 dated Nov. 5, 2009.
International Search Report and Written Opinion dated Nov. 26, 2009 for International Application No. PCT/US2009/042592 filed on May 1, 2009.
International Search Report and Written Opinion dated Jul. 28, 2011 for International Application No. PCT/US2010/055494 filed on Nov. 4, 2010 and published as WO/2011/057002 dated May 12, 2011.
Extended European Search Report dated Apr. 24, 2014, in EP Appl No. EP 08770070 filed Jun. 3, 2008.
Extended European Search Report dated Jul. 30, 2014, in EP Appl No. EP 10829110 filed Nov. 4, 2010.
International Search Report dated Jul. 21, 2015, for International Application No. PCT/US2015/025609.
International Search Report dated Jan. 11, 2016, for International Application No. PCT/US2015/025613.
JP, 2016-562549 Official Action, dated Mar. 8, 2019.
IN, 3614/DELNP/2012 Examination Report, dated Apr. 4, 2019.

* cited by examiner

METHODS AND DEVICES FOR TREATMENT OF VASCULAR DEFECTS

RELATED APPLICATIONS

This is a continuation of U.S. application Ser. No. 14/869,688, filed Sep. 29, 2015, which is a continuation of U.S. application Ser. No. 14/044,349, filed Oct. 2, 2013, which is a continuation of U.S. application Ser. No. 13/794,473, filed Mar. 11, 2013, now abandoned, which is a continuation of U.S. application Ser. No. 13/415,676, filed Mar. 8, 2012, now abandoned, which is a continuation of U.S. National Phase patent application Ser. No. 12/602,997, filed on Oct. 8, 2010, entitled "METHODS AND DEVICES FOR TREATMENT OF VASCULAR DEFECTS," naming Brian J. Cox et al. as inventors, which claims priority from international patent application number PCT/US2008/065694, filed on Jun. 3, 2008, entitled "Methods and Devices for Treatment of Vascular Defects," naming Brian J. Cox et al. as inventors, U.S. Provisional Patent Application Ser. No. 60/941,916, filed Jun. 4, 2007, entitled "Apparatus and Methods for Positioning and Delivery of Endoluminal Medical Devices," naming Brian J. Cox et al. as inventors, U.S. Provisional Patent Application Ser. No. 60/941,928, filed on Jun. 4, 2007, entitled "Method and Apparatus for Treatment of a Vascular Defect," naming Brian J. Cox et al. as inventors, U.S. Provisional Patent Application Ser. No. 60/948,683, filed on Jul. 9, 2007, entitled "Vascular Occlusion Devices," naming Brian J. Cox et al. as inventors, U.S. Provisional Patent Application Ser. No. 60/971,366, filed on Sep. 11, 2007, entitled "Method and Apparatus for Treatment of a Vascular Defect," naming Dean Schaefer et al. as inventors, and U.S. Provisional Patent Application Ser. No. 61/044,822, filed on Apr. 14, 2008, entitled "Methods and Devices for Treatment of Vascular Defects," naming Brian J. Cox et al. as inventors, which are all incorporated by reference herein in their entirety.

FIELD OF THE INVENTION

Generally, embodiments of devices and methods herein are directed to blocking a flow of fluid through a tubular vessel or into a small interior chamber of a saccular cavity within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels which transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these conditions include major surgery procedures which often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. Some such procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices is known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms and complexity and difficulty in the deployment thereof as most aneurysm treatments with this approach require the deployment of multiple coils.

Another approach to treating aneurysms without surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

A number of aneurysm neck bridging devices with defect spanning portions or regions have been attempted; however, none of these devices has had a significant measure of clinical success or usage. A major limitation in their adoption and clinical usefulness is the inability to position the defect spanning portion to assure coverage of the neck. Existing stent delivery systems that are neurovascular compatible (i.e. deliverable through a microcatheter and highly flexible) do not have the necessary rotational positioning capability. Another limitation of many aneurysm bridging devices described in the prior art is the poor flexibility. Cerebral blood vessels are tortuous and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm, with a decreased risk of inadvertent aneurysm rupture or blood vessel wall damage. In addition, what has been needed are methods and devices suitable for blocking blood flow in cerebral aneurysms over an extended period of time without a significant risk of deformation, compaction or dislocation.

SUMMARY

Some embodiments of a device for treatment of a patient's vasculature include an expandable body support structure. The expandable body support structure may include a low profile radially constrained state with an elongated tubular configuration that includes a first end, a second end, a longitudinal axis and elongate flexible struts disposed substantially parallel to each other with first ends thereof secured to a first ring and second ends thereof secured to a second ring. The first and second rings may be disposed substantially concentric to the longitudinal axis, and a middle portion of the expandable body may have a first transverse dimension with a low profile suitable for delivery from a microcatheter. The expandable body may also have an expanded relaxed state having an axially shortened configuration relative to the constrained state with the first ring disposed adjacent the second ring, both rings substantially concentric to the longitudinal axis and each strut forming a smooth arc between the first and second rings with a reverse bend at each end such that the arc of each strut extends axially beyond each respective ring and such that the middle portion has a second transverse dimension substantially greater than the first transverse dimension. Each strut may be configured to independently flex radially with respect to the longitudinal axis of the expandable body. A permeable layer defect spanning structure is disposed at and conforms to a profile of a second end of the expandable body when in the expanded relaxed state.

Some embodiments of a device for treatment of a patient's vasculature include an expandable body support structure having a low profile radially constrained state with a first end, a second end, an elongated tubular configuration having a longitudinal axis, elongate flexible struts connected at intersections between the first end and second end forming a plurality of open cells between struts in a middle portion of the expandable body, and a first transverse dimension suitable for delivery from a microcatheter configured for navigation in cerebral vasculature. The expandable body also has an expanded relaxed state with a tubular configuration including a second transverse dimension substantially greater than the first transverse dimension of the tubular configuration of the constrained state. A permeable layer may span at least one cell between struts of the expandable body. A permeable layer may also span a portion of a cell between struts.

Some embodiments of a device for treatment of a patient's vasculature include an expandable body support structure having a low profile radially constrained state with an elongated tubular configuration that includes a first end, a second end, a longitudinal axis and elongate flexible struts disposed substantially parallel to each other with first ends thereof secured relative to each other. A middle portion of the expandable body may have a first transverse dimension with a low profile suitable for delivery from a microcatheter. The expandable body also has an expanded relaxed state with an axially shortened configuration relative to the constrained state with each strut forming a smooth arc such that the arc of each strut extends axially beyond the first transverse dimension and such that the middle portion has a second transverse dimension substantially greater than the first transverse dimension. Each strut may be configured to independently flex in a radial orientation with respect to the longitudinal axis of the expandable body. A defect spanning structure comprising a permeable layer is disposed at and conforms to a profile of a second end of the expandable body when in the expanded relaxed state.

Some embodiments of a device for treatment of a patient's vasculature include an expandable body support structure having a low profile radially constrained state with a first end, a second end, an elongated tubular configuration having a longitudinal axis, elongate flexible struts connected at intersections between the first end and second end forming a plurality of open cells between struts in a middle portion of the expandable body. The expandable body has a first transverse dimension which is suitable for delivery from a microcatheter and which is configured for navigation in cerebral vasculature. The expandable body also has an expanded relaxed state with a tubular configuration including a second transverse dimension substantially greater than the first transverse dimension of the tubular configuration of the constrained state. A permeable layer is secured to the expandable body and may be configured to cover an aneurysm opening and which is axially displaced from the expandable body support structure and oriented substantially perpendicular to the longitudinal axis of the expandable body support structure when in the expanded relaxed state.

Some embodiments of a device for treatment of a patient's vasculature include an expandable body support structure having a low profile radially constrained state with an elongated tubular configuration that includes a first end, a second end, a longitudinal axis and elongate flexible struts disposed substantially parallel to each other with first ends thereof secured to a first ring and second ends thereof secured relative to each other. The first ring may be disposed substantially concentric to the longitudinal axis, and a middle portion of the expandable body may have a first transverse dimension with a low profile suitable for delivery from a microcatheter. The expandable body also has an expanded relaxed state having an axially shortened configuration relative to the constrained state with the second ends everted within a radially expanded middle portion and disposed adjacent the first ring substantially concentric to the longitudinal axis. Each strut may form a smooth arc between the first and second ends such that the arc of each strut extends axially beyond the first transverse dimension and such that the middle portion has a second transverse dimension substantially greater than the first transverse dimension. Each strut may also be configured to independently flex radially with respect to the longitudinal axis of the expandable body. A permeable layer defect spanning structure is disposed at and conforms to a profile of the first end of the expandable body when in the expanded relaxed state.

Some embodiments of a method of treating a vascular defect include providing a vascular defect treatment device having a support structure with an expandable body and a defect spanning structure that includes a plurality of microfibers that are substantially parallel to each other when the support structure is in an expanded relaxed state. A delivery system may be advanced to a position adjacent a vascular defect to be treated and the device positioned inside the vascular defect. Thereafter, the device may be deployed such that the expandable body self-expands and the defect spanning structure covers at least a portion of the defect opening or neck.

Some embodiments of a method of treating a vascular defect include providing a vascular defect treatment device having a support structure with an expandable body and a defect spanning structure that includes a plurality of microfibers that are substantially parallel to each other when the support structure is in an expanded relaxed state. A delivery system may be advanced to a position adjacent a vascular defect to be treated and the device positioned adjacent the vascular defect. The device may then be deployed such that the expandable body self-expands adjacent the vascular defect and the defect spanning structure covers at least a portion of the defect opening or neck.

Some embodiments of a method for treating a vascular defect include providing a device for treatment of a patient's vasculature having a support structure including a substantially hollow expandable body and a defect spanning structure that includes a permeable membrane disposed on the expandable body. A delivery system including a microcatheter may be advanced into a patient's body to a position adjacent a vascular defect to be treated. The device may then be rotationally positioned about a longitudinal axis of the catheter while the device is disposed in a radially constrained state at a distal end of the catheter. The rotational positioning may be carried out from a proximal end of the catheter with an elongate actuator releasably secured to the device. The device may be positioned until the defect spanning structure of the device is substantially aligned in a circumferential orientation with the vascular defect to be treated. The device may then be deployed so as to allow the device to achieve an expanded relaxed state with the permeable membrane at least partially covering the vascular defect so as to isolate the defect from the patient's vasculature.

Some embodiments of a method of treating a patient's vasculature include providing a device for treatment of a patient's vasculature that has a support structure with a self-expanding expandable body and a defect spanning structure has a permeable layer disposed on the expandable body. The device may be deployed at the confluence of three vessels of the patient's vasculature that form a bifurcation such that the defect spanning structure substantially covers the neck of a terminal aneurysm and one or more struts of the support structure span or cross each of the three vessels.

Some embodiments of a method of making a device for treatment of a patient's vasculature include forming a plurality of strut members into a substantially tubular member having a distal end and a proximal end wherein the strut members extend parallel to each other and a longitudinal axis of the tubular member in a cylindrical array. The strut members may also be secured to respective proximal and distal ends of the tubular structure. The struts are then shaped to form a globular support structure with a middle portion of the struts extending radially outward in a curving arc. For some embodiments, such a shape may be heat set or otherwise fixed. A permeable layer including a porous membrane, mesh or microfiber matrix that is less than about 50 microns thick may then be formed and secured to at least a portion of the support structure to form a defect spanning structure.

These features of embodiments will become more apparent from the following detailed description when taken in conjunction with the accompanying exemplary drawings.

DETAILED DESCRIPTION

Figure 1:
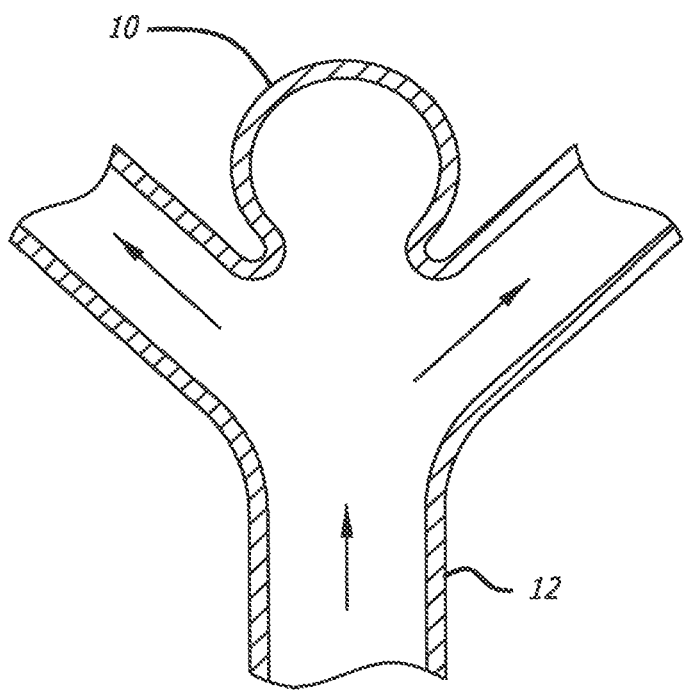
FIG. 1 is a sectional view of a terminal aneurysm.

As discussed above, there has been a need for devices and methods for the efficacious treatment of vascular defects that are suitable for minimally invasive deployment within a patient's vasculature, and particularly, within the cerebral vasculature of a patient. For such embodiments to be safely and effectively delivered to a desired treatment site and effectively deployed, the device embodiments may be configured for collapse to a low profile state with a transverse dimension suitable for delivery through a microcatheter and deployment from a distal end thereof. In addition, there has been a need for such devices that will maintain a clinically effective configuration with sufficient mechanical integrity once deployed so as to withstand the dynamic forces within a patient's vasculature over time.

Apparatus and method embodiments for the treatment of vascular defects including aneurysms and, more specifically, cerebral aneurysms, are discussed herein. Some embodiments are particularly useful for the treatment of cerebral aneurysms by reconstructing a vascular wall so as to wholly or partially isolate a vascular defect from a patient's blood flow. Some device embodiments include an endoluminal implant device for treatment of a patient's vasculature with a support structure and a defect spanning structure. Some embodiments of a device may be configured to be placed in a blood vessel adjacent a vascular defect to facilitate reconstruction, bridging of a vessel wall or both in order to treat the vascular defect.

For some of these embodiments, the support structure which may serve to anchor or fix the defect spanning structure in a clinically beneficial position may be secured to the patient's vasculature in the patient's vessel adjacent the vascular defect. In other embodiments, the support structure may be disposed in whole or in part within the vascular defect in order to anchor or fix the device with respect to the vascular structure. In either of these embodiments, the defect spanning structure, which is secured to the support structure, may be configured to span an opening, neck or other portion of the vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the defect spanning structure may include a membrane that allows some perfusion of blood through the membrane. The porosity of the membrane of the defect spanning structure may be configured to sufficiently isolate the vascular defect so as to promote healing and isolation of the defect, but allow sufficient flow through the membrane so as to reduce or otherwise minimize the mechanical force exerted on the membrane the dynamic flow of blood or other fluids within the vasculature against the membrane. Membrane embodiments may take on a variety of configurations to provide a desired clinical effect, including porous membranes, perforated membranes, membranes having multiple sizes of perforations, membranes having multiple layers, multiple layers of membranes, membranes having predetermined a porosity ratio and pore size, membranes configured for elution of bioactive agents as well as other configurations or any combination of these features.

Some device embodiments may also include a sealing member in the form of an elongate deformable element that is configured to conform to an irregular surface and form a seal between the defect spanning structure and the patient's vascular tissue. Such sealing members may be a continuous elongate element, such as with an annular ring, that may serve to prevent undesirable blood flow or flow of other fluids between the edges or periphery of the defect spanning structure and the tissue adjacent the defect spanning structure.

Figure 2:
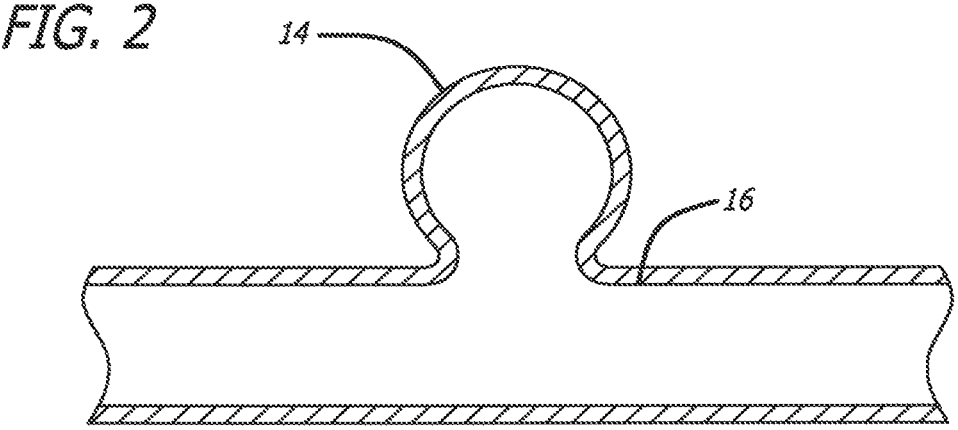
FIG. 2 is a sectional view of an aneurysm.

Some embodiments of devices for the treatment of a patient's vasculature discussed herein may be directed specifically to the treatment of specific types of defects of a patient's vasculature. For example, referring to FIG. 1, an aneurysm 10 commonly referred to as a terminal aneurysm is shown in section. Terminal aneurysms occur typically at bifurcations in a patient's vasculature where blood flow from a supply vessel splits into two or more branch vessels directed away from each other. The main flow of blood from the supply vessel 12, such as a basilar artery, sometimes impinges on the vessel where the vessel diverges and where the aneurysm sack forms. Terminal aneurysms may have a well defined neck structure where the profile of the aneurysm narrows adjacent the nominal vessel profile, but other terminal aneurysm embodiments may have a less defined neck structure or no neck structure. FIG. 2 illustrates a typical berry type aneurysm 14 in section where a portion of a wall of a nominal vessel section 16 weakens and expands into a sack like structure ballooning away from the nominal vessel surface and profile. Some berry type aneurysms may have a well defined neck structure as shown in FIG. 2, but others may have a less defined neck structure or none at all.

Embodiments of devices and methods for treatment of a patient's vasculature discussed herein may include a defect spanning structure configured to span all or a portion of a vascular defect in order to isolate the defect and promote healing, lessen or eliminate the risk or rupture or both. The defect spanning structure embodiments may include a variety of materials and configurations in order to provide a desired clinical result.

Figure 3:
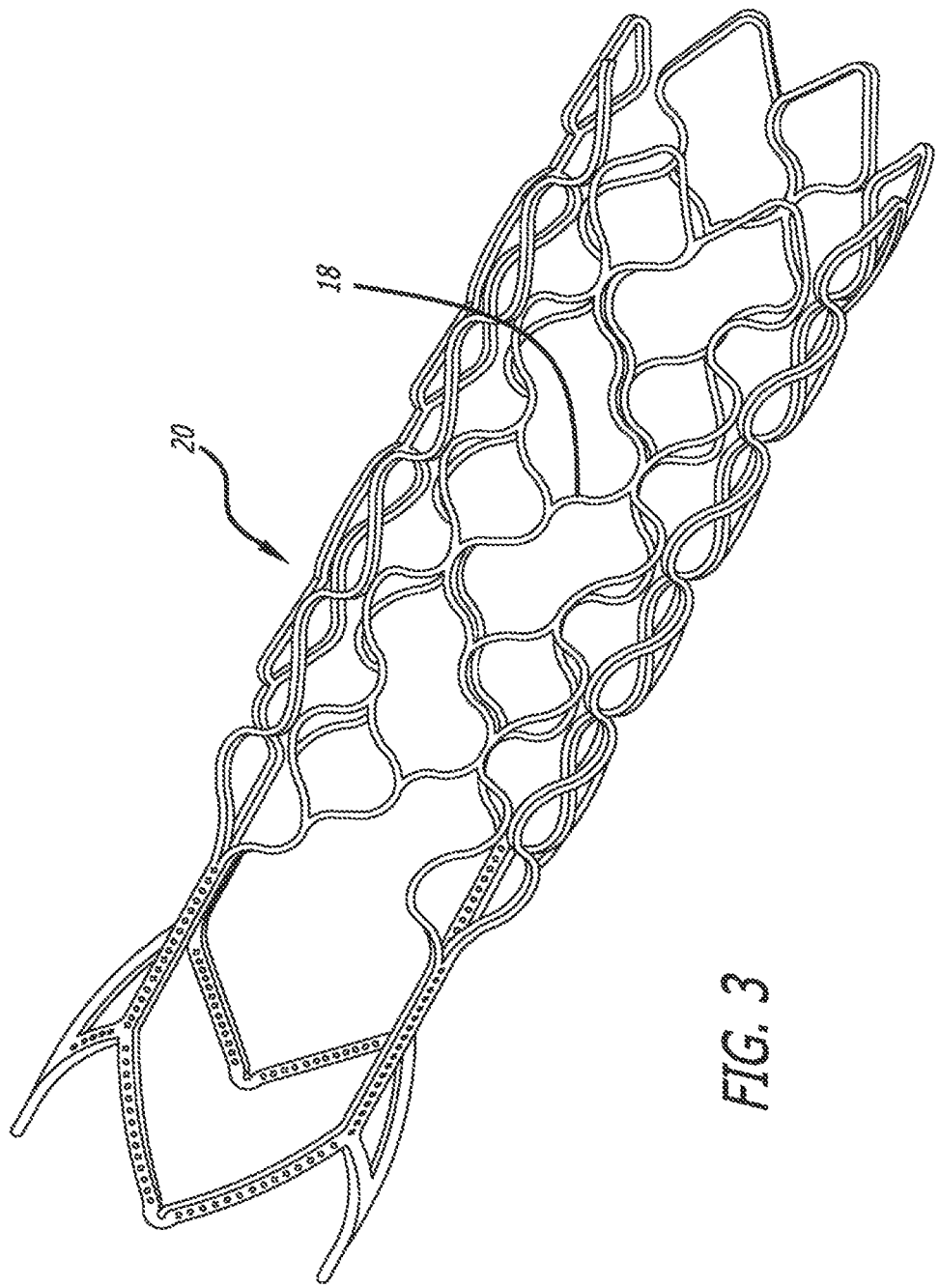
FIG. 3 is a perspective view of an embodiment of a laser cut tube in a tubular configuration prior to expansion and heat setting.
Figure 18:
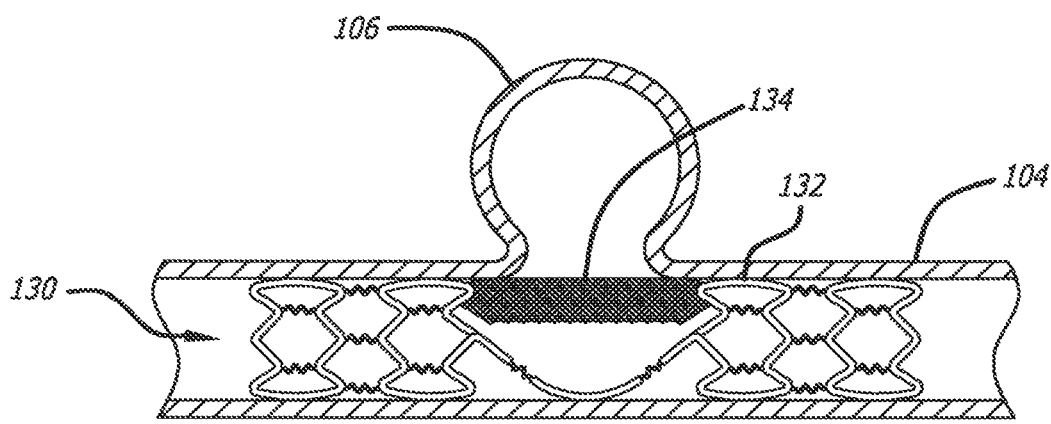
FIG. 18 illustrates an elevation view of an embodiment of a device for treatment of a patient's vasculature.

The defect spanning portion may be formed of a sheet material or fabric that is attached to the one or more surfaces of the support structure. Alternatively, the defect spanning portion may be fabricated as an integral part of the overall structure. These integral members may be cut by laser, photochemical etching or electrical discharge machining (EDM). In some embodiments, the defect spanning strut members 18 have at least one portion that has a wave-like shape as shown in the support structure embodiment 20 in FIG. 3. For some embodiments, material may be attached to the structure such that it substantially reduces the size of the fenestrations or cells and thus reduces the porosity in that area. For example, coatings, filaments, fibers, wires, struts, ribbons, sheet or fabric may be connected to portions of the structure to create small fenestrations or cells and thus higher density of the defect spanning portion (as shown in FIG. 18 below). Active materials such as a responsive hydrogel may be attached or otherwise incorporated into defect spanning structure embodiments such that it swells upon contact with liquids over time to reduce the porosity of the spanning structure. The defect spanning structure may have a microporous or microtextured surface. The microtextured surface may comprise pores, holes, voids, protrusions or other microfeatures. The microfeatures may be less than about 150 microns in diameter, height and/or depth.

Occlusive mesh and defect spanning structure embodiments generally may have a low volume to allow for the device to be collapsed into a small catheter for delivery. For some embodiments, the total volume of the occlusive membrane material may be less than about 5 mm3. For some embodiments, the total volume of the membrane material may be between 0.5 and 4 mm3. Defect spanning structure embodiments may be formed of strands of material and may be woven, braided or knitted as is known in the art of textile vascular grafts. Optionally, the device may include fibers or strands that are woven, braided or knitted as is known in the art of textile vascular grafts.

Defect spanning structure embodiments may be thinner than typical textiles used in vascular implants. The thickness of the defect spanning structure may be less than about 50 microns. In some embodiments, the defect spanning structure may be between about 2 and 10 microns thick. A thin defect spanning structure may allow it to be packed within the lumen of the support structure when collapsed and in a substantially cylindrical form for delivery through a catheter. The defect spanning structure may be porous and may be highly permeable to liquids. In contrast to most vascular prosthesis fabrics or grafts which typically have a water permeability below 2,000 ml/min/cm2 when measured at a pressure of 120 mmHg, the defect spanning structure may have a water permeability greater than about 2,000 ml/min/cm2 and may be between about 2,000 and 10,000 ml/min/cm2 when measured at a pressure of 120 mmHg. In some embodiments, the defect spanning structure is a porous thin membranous film.

Figure 4:
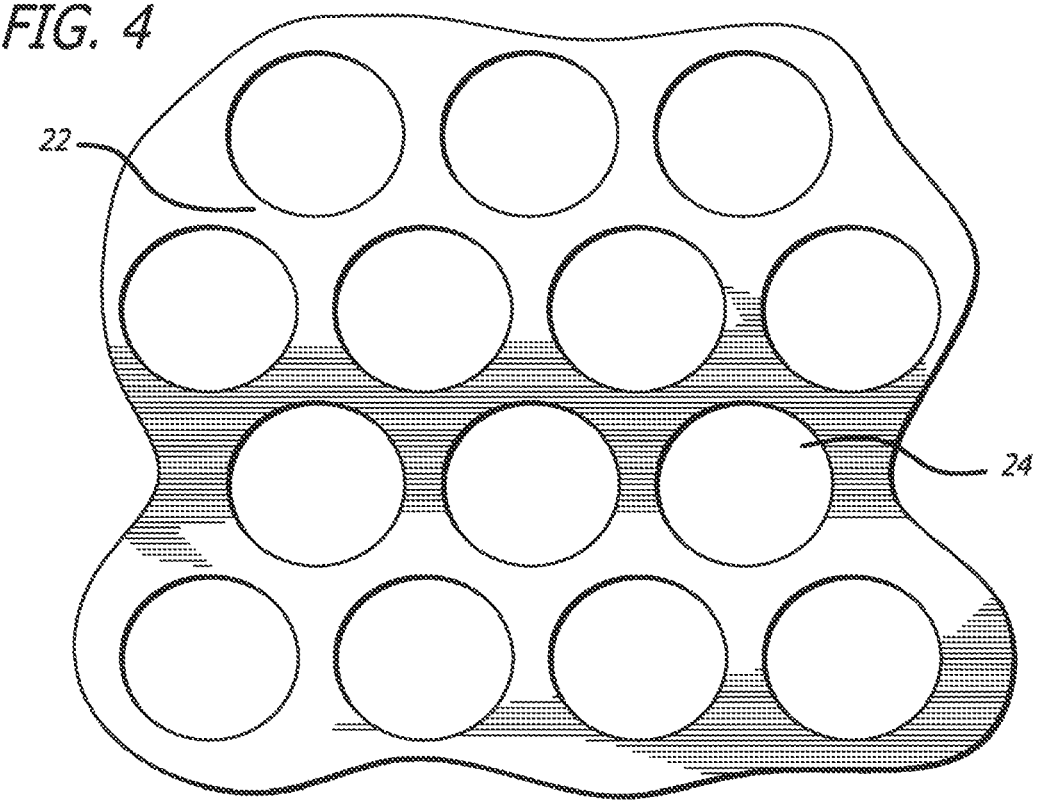
FIG. 4 illustrates an embodiment of a portion of a permeable layer for a defect spanning structure of a device for treatment of a patient's vasculature.
Figure 5:
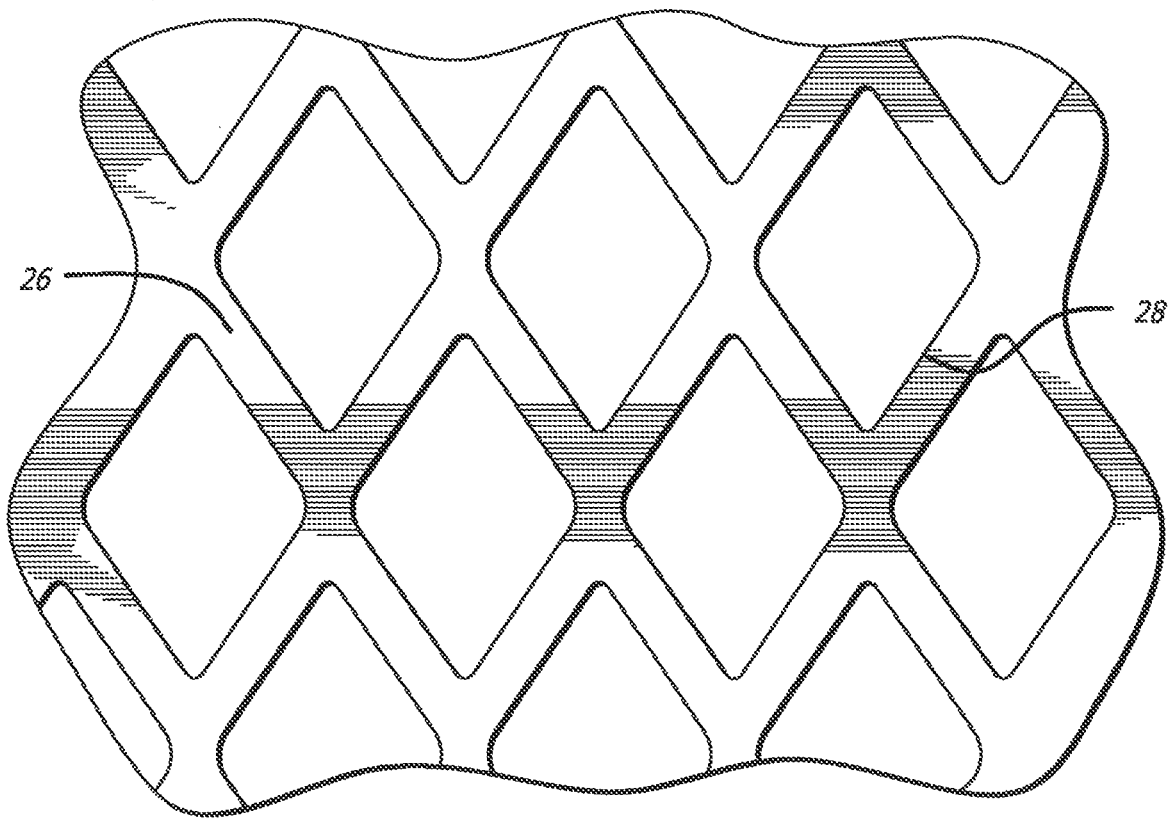
FIG. 5 illustrates an embodiment of a portion of a permeable layer for a defect spanning structure of a device for treatment of a patient's vasculature.

In some embodiments, the pores may be formed in an array such as those pores formed in the membrane embodiments shown in FIGS. 4 and 5. FIG. 4 shows a defect spanning structure membrane 22 having regularly spaced holes 24 having a substantially round shape through the membrane. FIG. 5 shows a defect spanning structure membrane 26 having a plurality of regularly spaced holes 28 having a substantially diamond shape.

Figure 6:
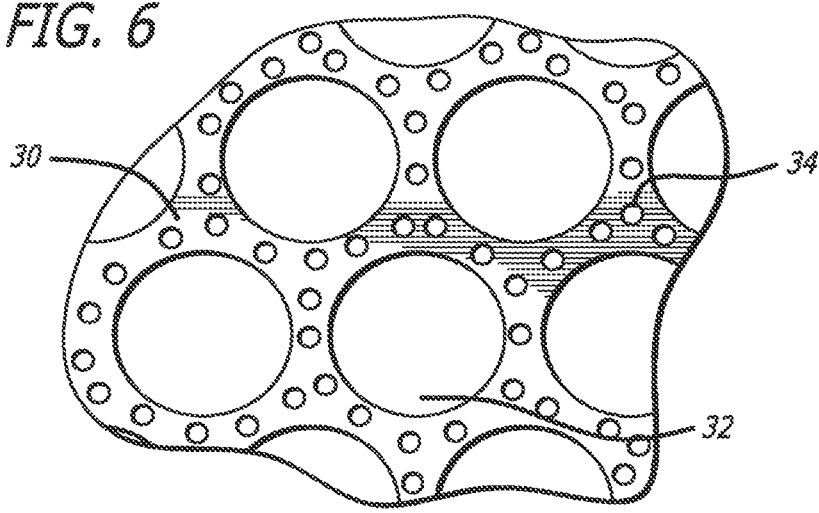
FIG. 6 illustrates an embodiment of a portion of a permeable layer for a defect spanning structure of a device for treatment of a patient's vasculature.

For some embodiments, the distance between the pores or web thickness may be less than about 100 microns and may be between about 20 and 60 microns. The pores may be in a variety of shapes including round, ovoid, square, and diamond. In some embodiments the defect spanning structure 30 may have macropores 32 and micropores 34 formed in the same membrane 30 as shown in FIG. 6. The macropores 32 may provide the majority of the desired permeability while the micropores 34 may provide improved healing and/or tissue ingrowth of the surfaces between the macropores 32. For some embodiments, the macropores 32 may be between about 100 microns and 500 microns in size (e.g., diameter). For some embodiments, the micropores 34 may be between about 10 microns and 100 microns in size. The macropores may be formed by laser perforation, mechanical perforation, surface treatments or any other suitable method during or after film formation. The micropores may be formed by various means known in the art of micropore formation including but not limited to the use of a porosigen during film formation, laser perforation, foaming processes, phase inversion processes or surface treatments during or after film formation.

Figure 7:
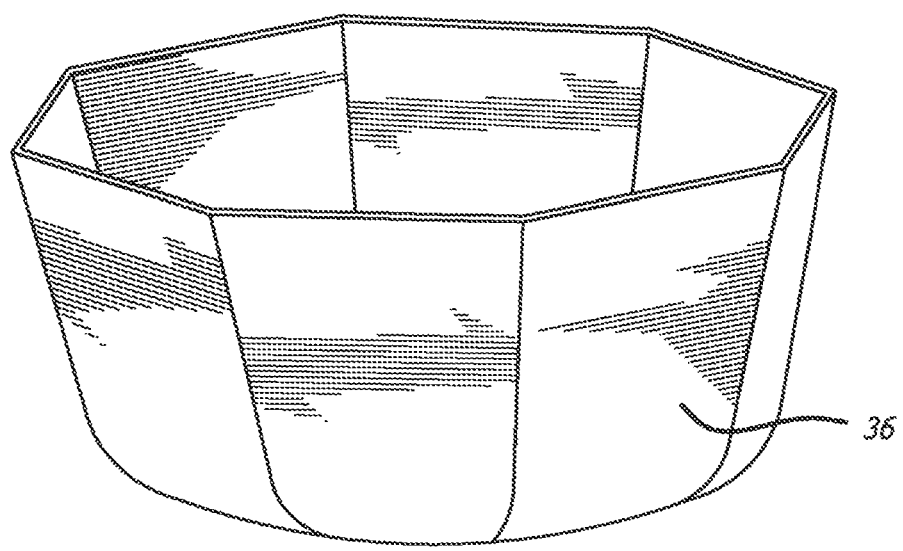
FIG. 7 shows a defect spanning structure in the form of a hemispherical dome with flat sides.

In some embodiments, the defect spanning structure may be formed in a generally three dimensional curved shape such as a hemisphere or substantially hemispheric shape. A three dimensional shape that may be desirable for some embodiments of permeable membranes of defect spanning structures may include a hemispherical dome 36 with flat or segmented sides without compound curvature wherein a membrane structure may extend directly or substantially directly between adjacent strut members as shown in FIG. 7. A membrane structure 36 having flat sides may provide minimization of extra membrane or spanning structure material that may be loose and buckle inward forming a path for blood to flow into an aneurysm around the device. For some embodiments, the membrane or defect spanning material may be stretched taught between adjacent strut members when a device is in an expanded deployed state.

For some embodiments, a portion of the proximal end opening area of the support structure may be covered or spanned by the defect spanning structure. The defect spanning structure for some embodiments may be highly porous having greater than about 60% porosity. In some embodiments, the area of the proximal end of a support structure covered by the defect spanning structure may be between about 10% and 40%. The defect spanning structure may be constructed by formation of a porous membrane or a network or array of small filamentary elements, fibers, wires or threads (hereinafter referred to as microfibers). The microfibers may have a thickness or diameter less than about 0.040 mm. In one embodiment, the thickness or diameter of the microfibers is between 0.015 and 0.030 mm.

Figure 8:
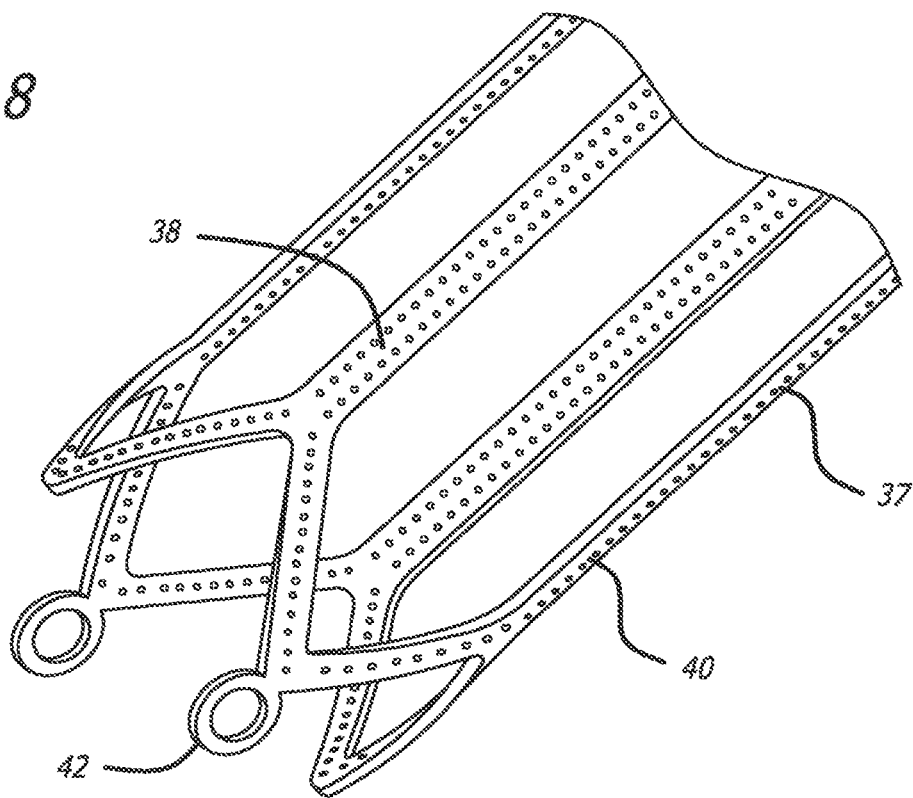
FIG. 8 is a perspective view of a distal or first end portion of a laser cut tube showing holes formed therein for securing microfibers or any other suitable filament.
Figure 9:
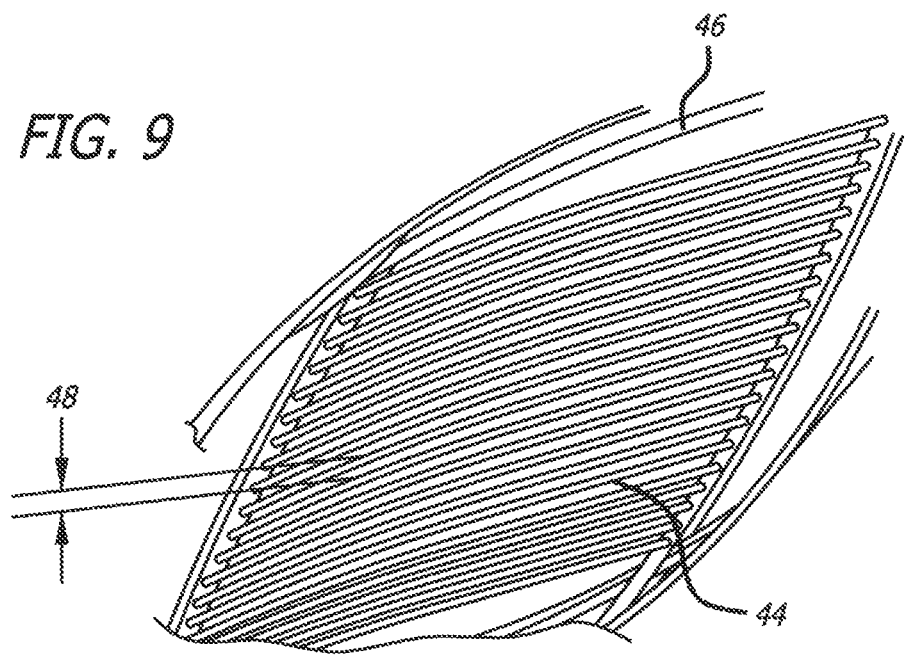
FIG. 9 shows a section of a support structure of a device for treatment of a patient's vasculature illustrating microfibers spanning an opening in the support structure.
Figure 10:
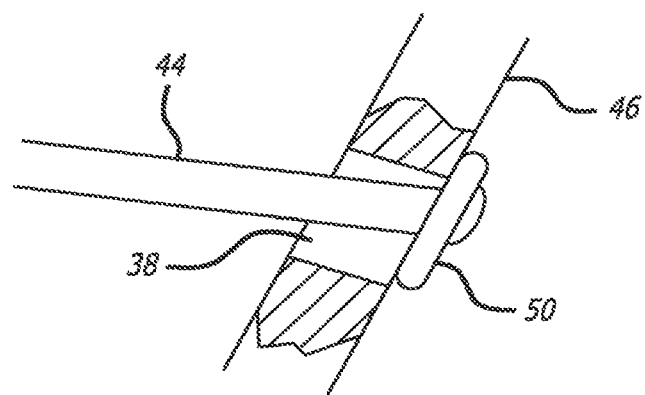
FIG. 10 is an elevation view in partial section of a junction between an end of a microfiber and a strut of a support structure of a device for treatment of a patient's vasculature.

In some embodiments, at least a portion of some struts of a support structure 37 have a plurality of holes or microholes 38 for attachment of the defect spanning structure as shown in FIG. 8. In some embodiments, there may be two rows of holes in a proximal portion of some struts 40 of the support structure 37. The holes 38 may be made such that they define a lumen that is perpendicular to the strut and the support structure 37. Thus the axis of the hole is radial to the support structure. Alternatively, the holes 38 may be tangential to the structure. For some embodiments, detachments loops 42 may be formed at an end, such as a first or proximal end of a support structure, such as support structure 37. In some embodiments, a defect spanning structure may be formed by a plurality of microfibers 44 that are threaded through the holes of one or more support structure struts 46 as shown in FIG. 9. The microfibers may span from strut to strut 46 in a substantially straight line or have a curved shape. The fibers 44 may be configured so as to substantially align with the surface or shape defined by the support structure. A gap between microfibers, as indicated by arrows 48 in FIG. 9, may be selected to generate a desired level of porosity of the defect spanning structure formed by the microfibers 44. The microfibers 44 may be attached to the structure by knots, adhesives or a small anchor element or member 50 that is attached to an end of a microfiber 44 and pulled against a hole 38 as shown in FIG. 10. For some embodiments, the fibers may have lengths configured to span a gap between struts and be held taught under tension when the support structure is in a relaxed deployed state.

Figure 11:
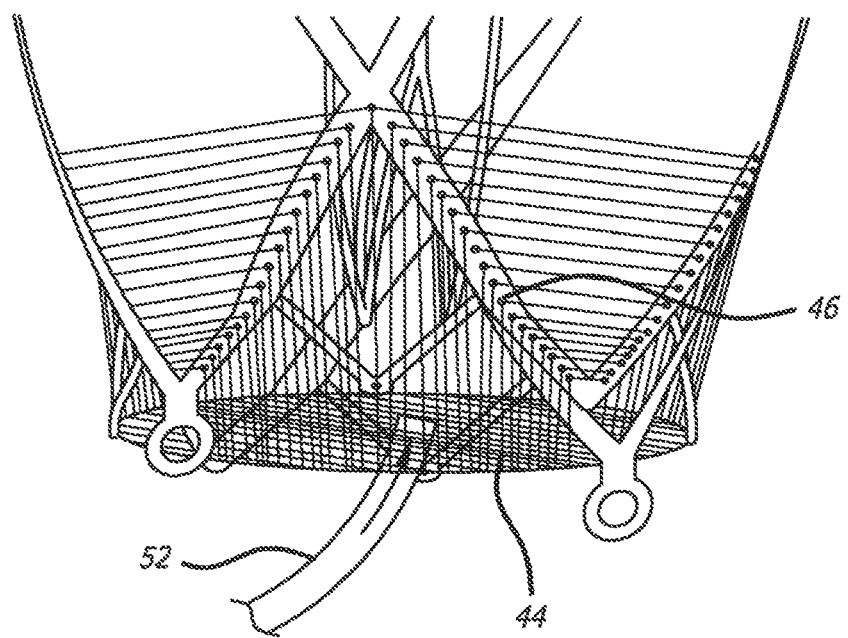
FIG. 11 is a perspective view of a proximal end of a device for treatment of a patient's vasculature having microfiber elements spanning gaps between a proximal portion of the support structure and with a distal portion of a microcatheter accessing an interior volume of the device.

Some of the microfibers may be substantially parallel as they span two struts. The gaps or slots 48 formed by the openings between two fibers may be less than about 0.125 mm for some embodiments. With the microfibers being arranged in a substantially parallel fashion as opposed to a mesh (e.g. braid), a guidewire or microcatheter 52 may be more easily be passed through the openings as shown in FIG. 11. This allows for a subsequent treatment such as the delivery of an embolic material and/or devices to fill at least a portion of the space behind the defect spanning structure. Further, mesh structures typically involve overlapping of fibers that result in a thicker, more voluminous membrane.

In some embodiments, the defect spanning structure may include a fabric which may be a mesh, network, weave, braid or other fabric construction of microfibers, wires or filaments. The fabric may be made in a variety of shapes including round, oval, elliptical. The thickness of the fabric may be between about 0.025 mm and about 0.25 mm. The individual microfibers may range in diameter from about 50 nm to about 50,000 nm (nanometers). In some embodiments, the microfibers may have a diameter or transverse dimension of about 500 nm to about 5,000 nm.

In some embodiments, the microporous structure may be formed by a mesh, matrix or other non-uniform structure of microfibers. For example, an electrospun mesh may be formed as described herein with pores that are on average between about 25 microns and 100 microns in size. Macroporosity of the mesh may be obtained by casting the fibers on to a macroporous (e.g., mesh) collector. A flow of gas through the collector or a vacuum may be used to reduce the spanning of the collector pores with fibers. Alternatively, macropores may be cut, burned or otherwise formed in a microporous mesh or microfiber matrix after it has been formed.

Figure 12:
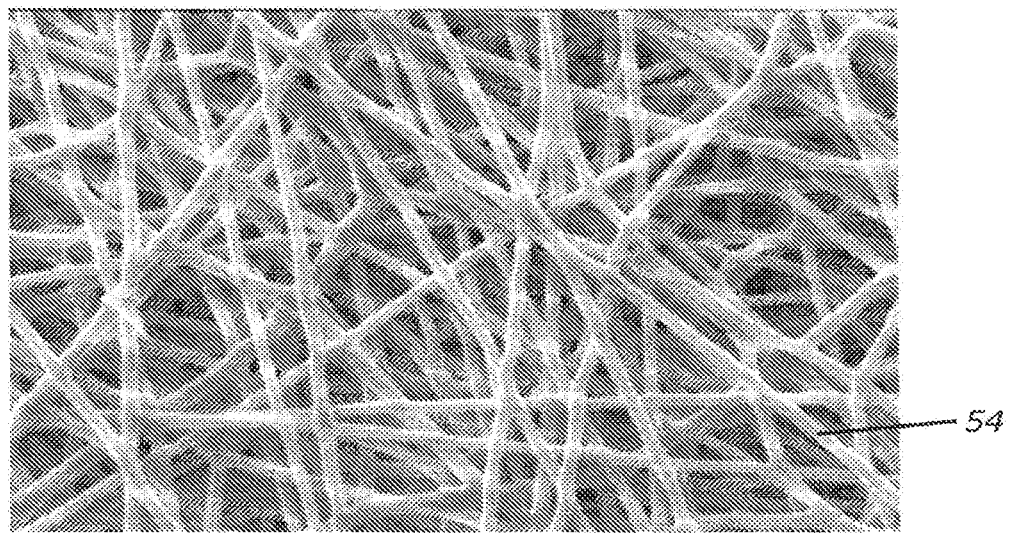
FIG. 12 is a view of an embodiment of electrospun microfiber.

Some process embodiments for making microfibers and/or fabric meshes include electrospinning. An example of an electrospun fabric 54 is shown in FIG. 12. Processes and materials for electrospinning fabric meshes for biomedical use are described by Quynh et al. in Electrospinning of Polymeric Nanofibers for Tissue Engineering Applications: A Review (Tissue Engr 2006; 12(5): 1197-1211, by Sen et al. in U.S. Patent Application No. 2005/0053782, filed Sep. 2, 2004, titled "Process for Forming Polymeric Micro and Nanofibers", by Laurencin et al. in U.S. Patent Application No. 2005/0112349, filed Sep. 10, 2004, titled "Polymeric Nanofibers for Tissue Engineering and Drug Delivery", by Devellian et al. in U.S. Patent Application No. 2005/0113868, filed Jun. 22, 2004, titled "Device, with Electrospun Fabric, for a Percutaneous Transluminal Procedure, and Methods thereof", and by Schewe et al. in U.S. Patent Application No. 2007/0144124, filed Dec. 23, 2005, titled "Spun Nanofiber, Medical Devices, and Methods", all of which are incorporated by reference herein in their entirety.

Some embodiments of electrospun fibers may be derived by charging a liquid typically to 5-30 kV vs. a ground a short distance away, which leads to charge injection into the liquid from the electrode. The sign of the injected charge depends upon the polarity of the electrode; a negative electrode produces a negatively charged liquid. The charged liquid is attracted to the ground electrode of opposite polarity, forming a so-called Taylor cone at the nozzle tip and, eventually, a fiber jet as the electric field strength exceeds the surface tension of the solution. Exemplary synthetic materials for producing electrospun fiber for the present invention include polyurethanes, polyimides, polyethers, silicones, polyesters, polyolefins, poly(ethylene-co-vinyl alcohol) copolymers from 2-propanol-water solutions and PVA poly(vinyl alcohol) fibers. Another class of materials for electroprocessing to make the compositions for embodiments herein may include extracellular matrix proteins. Examples include but are not limited to collagen, fibrin, elastin, laminin, and fibronectin.

Figure 13:
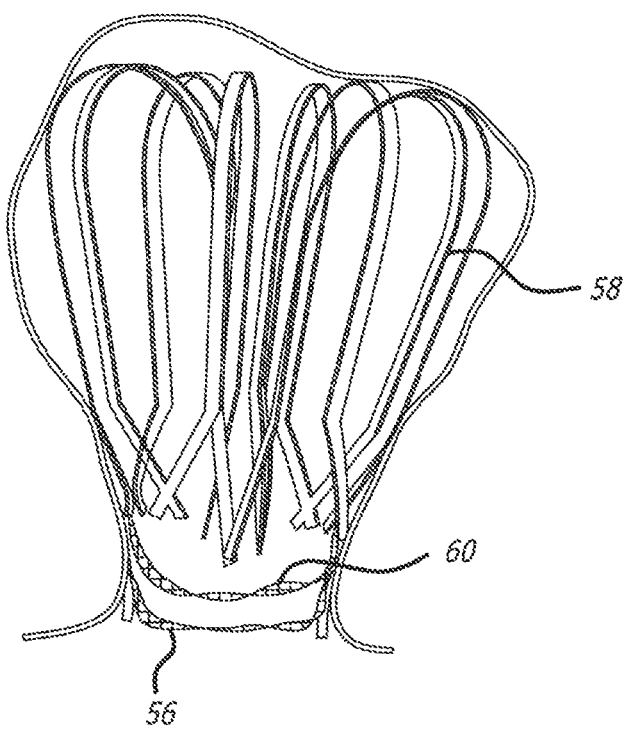
FIG. 13 is an elevation view in partial section of an embodiment of a device for treatment of a patient's vasculature deployed within an aneurysm.

Defect spanning structure embodiments of devices for treatment of a patient's vasculature may include multiple layers. A first or outer layer 56 may be attached to a proximal portion of a support structure 58. Subsequent or inner layer(s) 60 may be attached distal to the proximal end of the support structure struts as shown in FIG. 13 with some lower strut portions not shown for clarity of illustration. In some embodiments, the fabric layer or layers are fabricated directly on to the support structure 58, fusing to each other and/or the support structure as they are formed. The first or outer layer 56 may be constructed from a material with low bioactivity and hemocompatibility so as to minimize platelet aggregation or attachment and thus the propensity to form clot and thrombus. Optionally, the outer layer 56 may be coated or incorporate an antithrombogenic agent such as heparin or other antithrombogenic agents described herein or known in the art. One or more inner layers 60 distal to the first layer may be constructed of materials that have greater bioactivity and/or promote clotting and thus enhance the formation of an occlusive mass of clot and device within the vascular defect. Some materials that have been shown to have bioactivity and/or promote clotting include silk, polylactic acid (PLA), polyglycolic acid (PGA), collagen, alginate, fibrin, fibrinogen, fibronectin, Methylcellulose, gelatin, Small Intestinal Submucosa (SIS), poly-N-acetylglucosamine and copolymers or composites thereof.

Device embodiments discussed herein may be coated with various polymers to enhance it performance, fixation and/or biocompatibility. In addition, device embodiments may be made of various biomaterials known in the art of implant devices including but not limited to polymers, metals, biological materials and composites thereof. Device embodiments may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g., polyethylene terephthalate or PET), PolyEtherEther Ketone (PEEK), polytetrafluoroethylene (PTFE), polycarbonate urethane (PCU) and polyurethane (PU). The device may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable (e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable. Potentially suitable bioabsorbable materials include polylactic acid (PLA), poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials. An absorbable composite fiber may be made by combining a reinforcement fiber made from a copolymer of 18% glycolic acid and 82% lactic acid with a matrix material consisting of a blend of the above copolymer with 20% polycaprolactone (PCL). In some embodiments, the ratio of polylactide or lactic acid may be between about 65% and 90%.

In any of the device embodiments discussed herein, the defect spanning structure may be formed at least in part of acrylic, polyurethane, silicone, polypropylene, polyvinyl alcohol, polyesters (e.g., polyethylene terephthalate or PET), polybutester, and PolyEtherEther Ketone (PEEK). One potentially suitable group of materials includes polyurethanes-based polymers that may include a soft segment and a hard segment. The segments can be combined as copolymers or as blends. For example, polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

A group of materials that may be useful for the defect spanning structure may include silicone-urethane composites or siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as Elast-Eon (AORTECH BIOMATERIALS, Victoria, Australia); polytetramethyleneoxide (PTMO) and polydimethylsiloxane (PDMS) polyether-based aromatic siloxane-polyurethanes such as PurSil-10, -20, and -40 TSPU; PTMO and PDMS polyether-based aliphatic siloxane-polyurethanes such as PurSil AL-5 and AL-10 TSPU; aliphatic, hydroxy-terminated polycarbonate and PDMS polycarbonate-based siloxane-polyurethanes such as CarboSil-10, -20, and -40 TSPU (all available from Polymer Technology Group, Inc., Berkeley, Calif.).

The PurSil, PurSil-AL, and CarboSil polymers are thermoplastic elastomer urethane copolymers containing siloxane in the soft segment, and the percent siloxane in the copolymer is referred to in the grade name. For example, PurSil-10 contains 10% siloxane. These polymers are synthesized through a multi-step bulk synthesis in which PDMS is incorporated into the polymer soft segment with PTMO (PurSil) or an aliphatic hydroxy-terminated polycarbonate (CarboSil). The hard segment consists of the reaction product of an aromatic diisocyanate, MDI, with a low molecular weight glycol chain extender. In the case of PurSil-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking.

Other examples of siloxane-polyurethanes are disclosed in U.S. Patent Application Publication No. 2002/0187288 A1, titled "Medical Device Formed of Silicone-Polyurethane" filed Jun. 11, 2001, by Lim et al., which is incorporated herein by reference in its entirety. Another potentially suitable polyurethane based material for the defect spanning structure may be THORALON™ (THORATEC, Pleasanton, Calif.), as described by Jayaraman et al. in U.S. Patent Application No. 2002/0065552, filed Aug. 20, 2001, titled "Coated Vascular Grafts and Methods of Use", and by Ward in U.S. Pat. No. 4,675,361, filed Jun. 24, 1983, titled "Polymer Systems Suitable for Blood-Contacting Surfaces of a Biomedical Device, and Methods of Forming", both of which are incorporated by herein by reference in their entirety. According to these references, THORALON is a polyurethane base polymer (referred to as BPS-215) blended with a siloxane containing surface modifying additive (referred to as SMA-300). Base polymers containing urea linkages may also be used. The concentration of the surface modifying additive may be in the range of about 0.5% to about 5% by weight of the base polymer. The SMA-300 component (THORATEC) is a polyurethane including polydimethylsiloxane as a soft segment and the reaction product of diphenylmethane diisocyanate (MDI) and 1,4-butanediol as a hard segment.

Device embodiments discussed herein may include cells and/or other biologic material to promote healing. Device embodiments discussed herein may also be constructed to provide the elution or delivery of one or more beneficial drugs, other bioactive substances or both into the blood or the surrounding tissue. Device embodiments herein may include a surface treatment or coating on a portion, side or all surfaces that promotes or inhibits thrombosis, clotting, healing or other embolization performance measure. The surface treatment or coating may be a synthetic, biologic or combination thereof. For some embodiments, at least a portion of an inner surface of the defect spanning structure may have a surface treatment or coating made of a biodegradable or bioresorbable material such as a polylactide, polyglycolide or a copolymer thereof. Another surface treatment or coating material which may enhance the embolization performance of a device includes a polysaccharide such as an alginate based material. Potentially suitable alginate based materials are described by Becker et al. in U.S. Patent Application No. 2005/0133046, Ser. No. 10/738,317, filed on Dec. 17, 2003, titled Compositions and Methods for Improved Occlusion of Vascular Defects and by Cohen et al. in U.S. Patent Application No. 2006/0083721, Ser. No. 11/229,119, filed on Sep. 19, 2005, titled Injectable Cross-Linked Polymeric Preparations and Uses Thereof, which are hereby incorporated by reference in their entirety. Some coating embodiments may include extracellular matrix proteins such as ECM proteins. One example of such a coating may be Finale Prohealing coating which is commercially available from Surmodics Inc., Eden Prairie, Minn.

Defect spanning structure embodiments, including occlusive mesh embodiments, as well as support structure embodiments or both may include an antiplatelet agent, including but not limited to aspirin, glycoprotein IIb/IIIa receptor inhibitors (including, abciximab, eptifibatide, tirofiban, lamifiban, fradafiban, cromafiban, toxifiban, XV454, lefradafiban, klerval, lotrafiban, orbofiban, and xemilofiban), dipyridamole, apo-dipyridamole, persantine, prostacyclin, ticlopidine, clopidogrel, cromafiban, cilostazol, and nitric oxide. To deliver nitric oxide, the device embodiments may include a polymer that releases nitric oxide such as described by West et al., in U.S. Patent Application 2003/0012816, based on PCT filing dated Sep. 4, 2001, titled Nitric Oxide-Producing Hydrogel Materials, which is incorporated by reference herein in its entirety. Device embodiments may also deliver or include an anticoagulant such as heparin, low molecular weight heparin, hirudin, warfarin, bivalirudin, hirudin, argatroban, forskolin, ximelagatran, vapiprost, prostacyclin and prostacyclin analogues, dextran, synthetic antithrombin, Vasoflux, argatroban, efegatran, tick anticoagulant peptide, Ppack, HMG-CoA reductase inhibitors, and thromboxane A2 receptor inhibitors.

Bioactive agents suitable for use in the embodiments discussed herein may include those having a specific action within the body as well as those having nonspecific actions. Specific action agents are typically proteinaceous, including thrombogenic types and/or forms of collagen, thrombin and fibrogen (each of which may provide an optimal combination of activity and cost), as well as elastin and von Willebrand factor (which may tend to be less active and/or expensive agents), and active portions and domains of each of these agents. Thrombogenic proteins typically act by means of a specific interaction with either platelets or enzymes that participate in a cascade of events leading eventually to clot formation. Agents having nonspecific thrombogenic action are generally positively charged molecules, e.g., polymeric molecules such as chitosan, polylysine, poly(ethylenimine) or acrylics polymerized from acrylimide or methacrylamide which incorporate positively-charged groups in the form of primary, secondary, or tertiary amines or quarternary salts, or non-polymeric agents such as (tridodecylmethylammonium chloride). Positively charged hemostatic agents promote clot formation by a non-specific mechanism, which includes the physical adsorption of platelets via ionic interactions between the negative charges on the surfaces of the platelets and the positive charges of the agents themselves.

In some embodiments, the defect spanning structure and/or support structure may be coated with a composition that may include genetically engineered peptides, nanoscale structured materials or precursors thereof (e.g., self-assembling peptides). The peptides may have with alternating hydrophilic and hydrophobic monomers that allow them to self-assemble under physiological conditions. The composition may comprise a sequence of amino acid residues. Such compositions are described by Ellis-Behnke et al. in U.S. Patent Application 2007/0203062, filed Apr. 25, 2006, titled Compositions and Methods for Promoting Hemostasis and Other Physiological Activities, which is herein incorporated in its entirety by reference.

In some embodiments, the defect spanning structure may comprise a thin metallic film material. The thin film metal may be fabricated by sputter deposition and may be formed in multiple layers. The thin film may be a nickel-titanium alloy also known as nitinol. Methods for forming thin film nitinol structures are described by Gupta et al. in an undated paper titled "Nitinol Thin Film Three-Dimensional Devices—Fabrication and Applications", TiNi Alloy Company, 1619 Neptune Drive, San Leandro, Calif., and U.S. Pat. No. 6,746,890 by Gupta et al., filed Jul. 17, 2002, titled Three Dimensional Thin Film Devices and Methods of Fabrication, which are both incorporated by reference herein in their entirety.

In some embodiments, the defect spanning structure may be formed at least in part of a dissolvable polymer that is cast into a thin film. The film may be made by spraying the dissolved polymer onto a mandrel that has a surface with the desired shape of the membrane. The polymer may be dissolved using various solvents including but not limited to Dimethyl Acetamide (DMAC), Tetrahydrofuran (THF), Methyl Ethyl Ketone (MEK), Acetone, and Cyclohexanone. The amount of solvent in the dissolved polymer mixture may be high, that is greater than about 70% to produce a low viscosity mixture that produces a thin layer in each coat. A mixture of two or more solvents may be used to achieve the best membrane formation. In some embodiments, the mixture may be between 70% and 95% THF and between 5% and 25% DMAC. The sprayer may include a solution reservoir and an atomization chamber (nozzle) where air, at the correct pressure atomizes the solution. The solvent in the solution is allowed to evaporate either in a forced convection environment or in an oven or a combination of both. The resulting material is a very thin layer of polymer. Several other layers can then be sprayed on the thin polymer layer to achieve a desired thickness. The defect spanning structure may be formed in two spraying steps. In this case a first membrane may be cast and secured to a support structure. A second membrane may be then sprayed on the support structure side such that the solvent may be allowed to partially dissolve the membrane and fuse the membrane and the newly sprayed polymer once the solvent is allowed to evaporate. Thus the second layer is formed with struts of a support structure encapsulated between the two layers of the polymer layer.

Support structure embodiments may be configured to hold defect spanning structure embodiments in place which spans a vascular defect to allow healing, clotting mechanisms and/or vaso-occlusive materials to occlude the defect space. Methods are discussed that enable the defect spanning structure to be accurately positioned within a luminal organ such that it substantially covers the defect opening (e.g., aneurysm neck) and thus substantially blocks flow into the defect without covering large or significant portions of the parent vessel that may inadvertently occlude other blood vessels. Optionally, some device embodiments may be used to block the flow into a vessel that is intended to be occluded.

Figure 39:
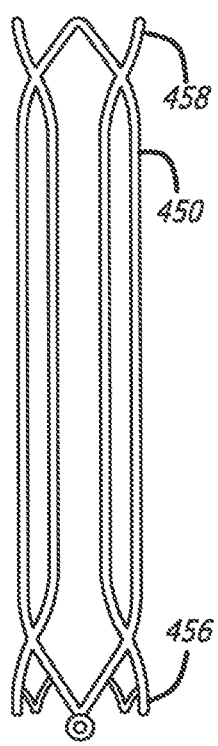
FIG. 39 is an elevation view of a laser cut tube prior to heat setting and formation of a support structure embodiment for a device for treatment of a patient's vasculature.
Figure 49:
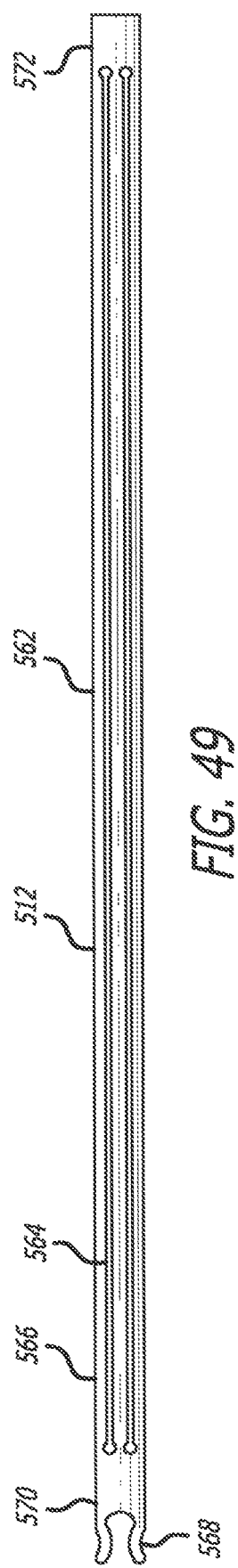
FIG. 49 is an elevation view of a laser cut tube prior to heat setting and formation of an embodiment of a support structure for a device for treatment of a patient's vasculature.

In any of the suitable device embodiments discussed herein, the support structure may include one or more fixation elements or surfaces to facilitate fixation of the device within a blood vessel or other vascular site. The fixation elements may comprise hooks, barbs, protrusions, pores, microfeatures, texturing, bioadhesives or combinations thereof. Embodiments of the support structure may be fabricated from a tube of metal where portions are removed. The removal of material may be done by laser, electrical discharge machining (EDM), photochemical etching and traditional machining techniques. In some embodiments, the support structure may have an initial manufactured configuration that is substantially tubular, as shown in FIGS. 39 and 49 discussed below. In any of the described embodiments, the support structure may be constructed with a plurality of wires, cut or etched from a sheet of a material, cut or etched from a tube or a combination thereof as in the art of vascular stent fabrication.

Support structure embodiments may be formed at least in part of wire, ribbon, or other filamentary elements. These filamentary elements may have circular, elliptical, ovoid, square, rectangular, or triangular cross-sections. Support structure embodiments may also be formed using conventional machining, laser cutting, electrical discharge machining (EDM) or photochemical machining (PCM). If made of a metal, it may be formed from either metallic tubes or sheet material. Some PCM processes for making stents are described in U.S. Pat. No. 5,907,893 by Zadno-Azizi et al., titled "Methods for the manufacture of radially expansible stents", filed Jan. 31, 1997 and in U.S. Patent Application 2007/0031584 by Roth, titled "Thin film stent", filed Oct. 10, 2006 which are both incorporated by reference herein in their entirety.

Figure 14:
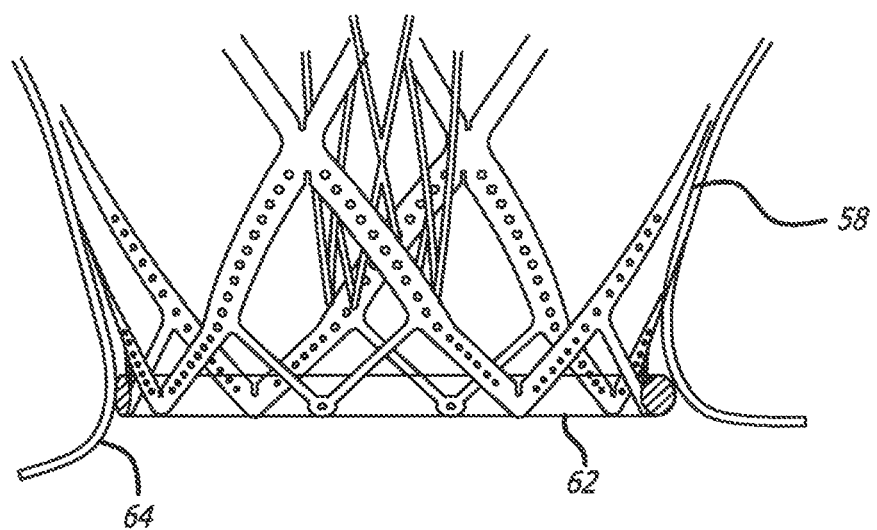
FIG. 14 is an elevation view in partial section of a proximal portion of an embodiment of a device for treatment of a patient's vasculature deployed within an aneurysm.
Figure 15:
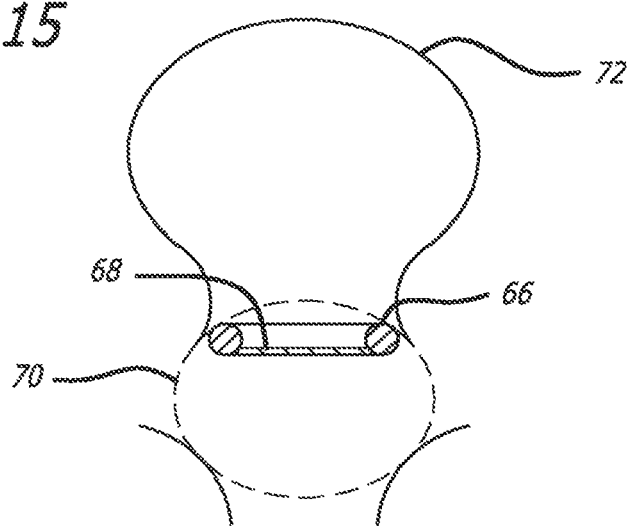
FIG. 15 is a sectional view of a terminal aneurysm with an embodiment of a device for treatment of a patient's vasculature deployed adjacent the aneurysm.

Support structure embodiments may further include fixation elements and/or one or more sealing members that extend from one or more of the support structure struts at or near the proximal end of the device to facilitate fixation of the device within the vascular defect. Fixation or sealing member embodiments may extend radially from the axis of a support structure thereby engaging the neck and/or inner surface of a parent blood vessel. A sealing member 62 having a substantially annular configuration may be secured to a proximal portion of a support structure 58 and sealed against a tissue surface of a patient's vascular defect, such as an aneurysm neck 64, as shown in FIG. 14. The fixation members may include a coating or small surface features such as pores, voids, filaments, barbs, fibers, or strands that engage, penetrate or otherwise facilitate attachment to the adjacent tissue. Pores or voids in the surface may be filled with a bioadhesive. Optionally, the fixation/sealing member(s) may be fabricated from a swellable material. Potentially suitable expansible swellable materials may include foams, sponge-like materials and hydrogels to facilitate sealing, fixation and/or healing of the device. Such materials may include microporous materials such as an open-celled foam, sponge, or other cellular structure. A potentially suitable swellable hydrogel is described in U.S. Pat. No. 6,878,384 by Cruise et al., titled "Hydrogels that undergo volumetric expansion in response to changes in their environment and their methods of manufacture and use", filed Mar. 13, 2001 which is incorporated by reference herein in its entirety. The expansible material may be formed into a torodial ring 66 about the periphery of the defect spanning structure 68 as shown in FIG. 15. A support structure 70 embodiment may be deployed adjacent a vascular defect 72 so as to position the defect spanning structure 68 across the neck of the vascular defect 72.

Device embodiments discussed herein may be delivered and deployed from a delivery and positioning system that includes a microcatheter, such as the type of microcatheter that is known in the art of neurovascular navigation and therapy. Device embodiments may be elastically collapsed and restrained by a tube or other radial restraint for delivery and deployment. The device may be delivered through a catheter such as a microcatheter for endovascular treatment of cerebral aneurysms. The microcatheter may generally be inserted through a small incision accessing a peripheral blood vessel such as the femoral artery. The microcatheter may be delivered or otherwise navigated to a desired treatment site from a position outside the patient's body over a guidewire under fluoroscopy or by other suitable guiding methods. The guidewire may be removed during such a procedure to allow insertion of the device through the catheter lumen in some methods.

Delivery and deployment of device embodiments discussed herein may be carried out by compressing the device to a radially constrained and longitudinally flexible state. The device is then delivered to a desired treatment site within the catheter, and then ejected or otherwise deployed from a distal end of the microcatheter. The device is then allowed to assume an expanded relaxed or partially relaxed state with the defect spanning structure of the device spanning or partially spanning a portion of the vascular defect or the entire vascular defect. The support structure will also be allowed to assume an expanded relaxed state so as to engage a portion of a patient's vasculature adjacent to or within the vascular defect to be treated. The device may also be activated by the application of an energy source to assume an expanded deployed configuration once ejected from the distal section of the microcatheter. Once the device is deployed at a desired treatment site, the microcatheter may then be withdrawn.

Delivery and positioning system embodiments may provide for the ability to rotate a device for treatment of a patient's vasculature in-vivo without translating torque along the entire length of the delivery apparatus. Some embodiments for delivery and positioning devices are described in co-owned U.S. Provisional Patent Application Ser. No. 60/941,916 by Cox et al. titled "Apparatus and Methods for Positioning and Delivery of Endoluminal Medical Devices, filed Jun. 4, 2007 which is incorporated by reference herein in its entirety. Embodiments of the delivery and positioning apparatus, discussed in more detail below with reference to FIGS. 64-72, may include a distal rotating member that allows rotational positioning of the vascular defect support structure. The delivery and positioning apparatus may include a distal rotating member which rotates the implant in-vivo without the transmission of torque along the entire length. Optionally, delivery system may also rotate the implant without the transmission of torque in the intermediate portion between the proximal end and the distal rotatable end. The delivery and positioning apparatus may be releasably secured to the defect spanning structure, support structure or any other suitable portion of the device for treatment of a patient's vasculature.

Device embodiments discussed herein may be releasable from a flexible, elongate delivery apparatus such as a guidewire or guidewire-like structure. The release of device embodiments from such a delivery apparatus may be activated by a thermal mechanism, electrolytic mechanism, hydraulic mechanism, shape memory material mechanism, or any other mechanism known in the art of endovascular implant deployment. Potentially suitable thermal release mechanisms are described by Gandhi et al. in U.S. Patent Application 2006/0253149, filed May 16, 2006, titled Apparatus for Deployment of Micro-Coil Using a Catheter, and by Fitz et al. in U.S. Patent Applications 2006/0052815, filed Aug. 25, 2005, titled Thermal Detachment System for Implantable Devices, and 2006/0200192, filed May 3, 2006, titled Thermal Detachment System for Implantable Devices, which are both incorporated by reference herein in their entirety.

Embodiments for deployment and release of therapeutic devices, such as deployment of embolic devices or stents within the vasculature of a patient, may include connecting such a device via a releasable connection to a distal portion of a pusher or acutator member. The therapeutic device may be detachably mounted to the distal portion of the pusher member by a filamentary tether, string, thread, wire, fiber, or the like, which may be referred to as the tether. The tether may be in the form of a monofilament, rod, ribbon, hollow tube, or the like. Some embodiments of the tether may have a diameter or maximum thickness of between about 0.05 mm and 0.2 mm. The tether may be configured to be able to withstand a maximum tensile load of between about 0.5 kg and 5 kg. The tether may be severed by the input of energy such as electric current to a heating element causing release of the therapeutic device. For some embodiments, the heating element may be a coil of wire with high electrical resistivity such as a platinum-tungsten alloy. The tether member may pass through or be positioned adjacent the heater element. The heater may be contained substantially within the distal portion of the pusher member to provide thermal insulation to reduce the potential for thermal damage to the surrounding tissues during detachment. In another embodiment, current may pass through the tether which also acts as a heating element.

Many materials may be used to make tether embodiments including polymers, metals and composites thereof. One class of materials that may be useful for tethers includes polymers such as polyolefin, polyolefin elastomer such as polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials that may be used for tether embodiment may include metals such as nickel titanium alloy (Nitinol), gold, platinum, tantalum and steel. Other materials that may be useful for tether construction includes wholly aromatic polyester polymers which are liquid crystal polyers (LCP) that may provide high performance properties and are highly inert. A commercially available LCP polymer is Vectran, which is produced by Kuraray Co. (Tokyo, Japan). The selection of the material may depend on the melting or softening temperature, the power used for detachment, and the body treatment site. The tether may be joined to the implant and/or the pusher by crimping, welding, knot tying, soldering, adhesive bonding, or other means known in the art.

Embodiments of devices and methods for release and deployment of a therapeutic device within the vasculature of a patient may include an elongate, flexible pusher member having an interior lumen, and a distal portion. The distal portion may include a mechanism for detachably mounting the therapeutic device to the pusher member. In general, such deployment apparatus embodiments may be inserted into a patient using a catheter or other tubular access device. The therapeutic device may be positioned at a desired placement or treatment site within a patient's vasculature and energy may then be delivered to a heating element which heats a tether causing it to fail by breaking, melting or any other suitable mechanism. Failure of the tether results in detachment of the therapeutic device from the pusher member and deployment of the therapeutic device in the patient's vasculature at the desired site.

Any embodiment of devices for treatment of a patient's vasculature, delivery system for such devices or both discussed herein may be adapted to deliver energy to the device for treatment of a patient's vasculature or to tissue surrounding the device at the implant site for the purpose of facilitating fixation of a device, healing of tissue adjacent the device or both. In some embodiments, energy may be delivered through a delivery system to the device for treatment of a patient's vasculature such that the device is heated. In some embodiments, energy may be delivered via a separate elongate instrument (e.g., catheter) to the device for treatment of a patient's vasculature and/or surrounding tissue at the site of the implant. Examples of energy embodiments that may be delivered include but are not limited to light energy, thermal or vibration energy, electromagnetic energy, radio frequency energy and ultrasonic energy. For some embodiments, energy delivered to the device may trigger the release of chemical or biologic agents to promote fixation of a device for treatment of a patient's vasculature to a patient's tissue, healing of tissue disposed adjacent such a device or both.

Defect spanning structure embodiments may be configured to react to the delivery of energy to effect a change in the mechanical or structural characteristics, deliver drugs or other bioactive agents or transfer heat to the surrounding tissue. For example, either the support structure and/or the defect spanning structure of device embodiments may be made softer or more rigid from the use of materials that change properties when exposed to electromagnetic energy (e.g., heat, light, or radio frequency energy). Application of an agent in combination with energy to a region of blood vessel wall weakness to strengthen the wall and/or inducing fibrosis is discussed in U.S. Pat. No. 6,719,7789, to Van Tassel, et al. filed Mar. 24, 2000, titled "Methods for Treatment of Aneurysms", which is incorporated by reference herein in its entirety. In another example, the defect spanning structure may include a polymer that reacts in response to physiologic fluids by expanding. An exemplary material is described by Cox in U.S. Patent Application No. 2004/0186562, filed Jan. 22, 2004, titled "Aneurysm Treatment Device and Method of Use", which is incorporated by reference herein in its entirety.

Figure 16:
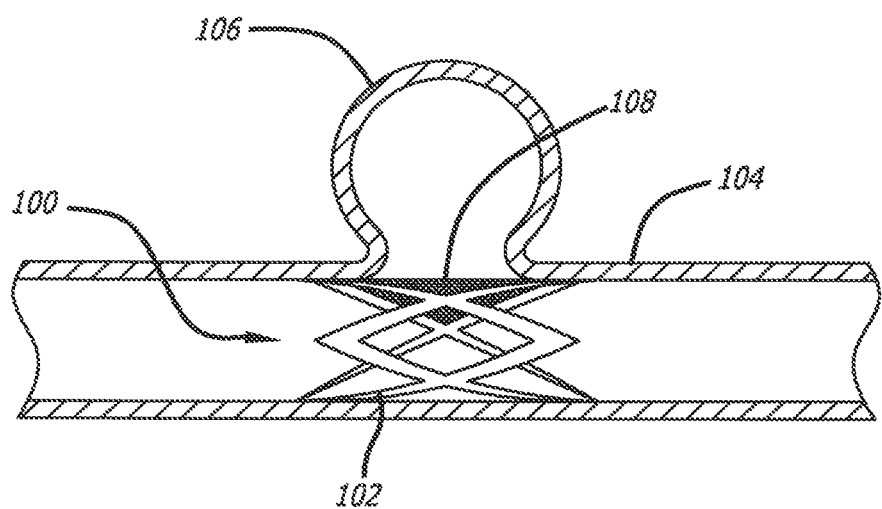
FIG. 16 shows a view in longitudinal section of an aneurysm with an embodiment of a device for treatment of a patient's vasculature deployed adjacent the aneurysm.
Figure 17:
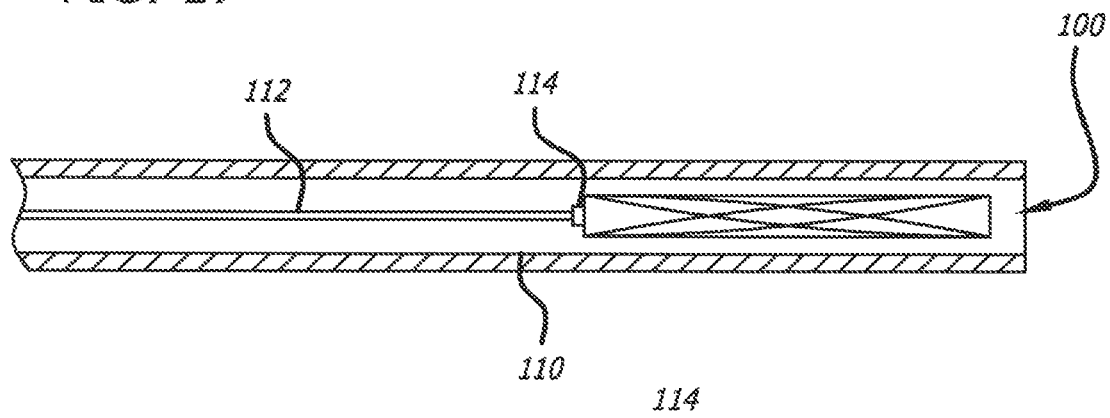
FIG. 17 shows the device of FIG. 16 disposed within a microcatheter in a collapsed radially constrained state.

Referring to FIG. 16, an embodiment of a device for treatment of a patient's vasculature 100 is shown in an expanded deployed state. A support structure 102 of the device includes strut members disposed in a substantially tubular configuration. The support structure is configured to span or cross the lumen of a parent vessel 104 both upstream and downstream of the vascular defect shown in the form of a berry aneurysm 108 extending from the parent vessel 104. A defect spanning structure 108 of the device is configured to substantially block flow of blood into the vascular defect when positioned substantially over the defect as shown. The expandable body support structure 102 includes a low profile radially constrained state as shown in FIG. 17 where the device 100 is disposed within a distal portion of a catheter 110.

The support structure 102 further includes a first end, a second end and an elongated tubular configuration having a longitudinal axis. The elongate flexible struts are connected or otherwise secured at intersections between the first end and second end forming a plurality of open cells between struts in a middle portion of the expandable body. The elongated tubular configuration has a first transverse dimension in a radially compressed state that is suitable for delivery from a microcatheter configured for navigation in a patient's cerebral vasculature as shown in FIG. 17. The radial constraint on the device may be applied by an inside surface of the inner lumen of the microcatheter 110, or it may be applied by any other suitable mechanism or structure that may be released or withdrawn in a controllable manner so as to eject the device from the distal end of the catheter.

The tubular configuration has an expanded relaxed state with a tubular configuration having a second transverse dimension substantially greater than the first transverse dimension of the tubular configuration of the constrained state which is configured to engage tissue of a patient's vasculature adjacent a vascular defect 106 as shown in FIG. 16. The engagement of the tubular member of the support structure 102 may be achieved by the exertion of an outward radial force against tissue of the patient's vessel of the tubular support structure. Such a force may be exerted in some embodiments wherein the nominal outer transverse dimension or diameter of the support structure in the relaxed unconstrained state is larger than the nominal inner transverse dimension of the vessel within which the support structure is being deployed. The elastic resiliency of the support structure may be achieved by an appropriate selection of materials, such as superelastic alloys, including nickel titanium alloys, stainless steel, or any other suitable material.

The defect spanning structure 108 in the form of a permeable layer spans at least one cell between struts of the expandable body and may be disposed against the opening to the vascular defect 106 so as to close off the opening to the vascular defect as shown in FIG. 16. The defect spanning structure may include any of the materials discussed above including perforated membranes, laser cut polymer membranes, microfibers, including electrospun microfibers, as well as others. The defect spanning structure may be secured to the support structure by adhesive bonding, suturing, lacing, or any other suitable method.

For some embodiments, the struts of the expandable body 102 may include perforations or holes which are configured for securing the permeable layer to the expandable body by lacing, suturing or the like. The defect spanning structure 108 in the form of a permeable layer may be disposed interior to an outer surface of the expandable body. The defect spanning structure may also include multiple layers. For some multiple layer embodiments, an outer layer may include an anti-thrombogenic agent and an inner layer disposed towards a cavity of a the vascular defect, such as the aneurysm shown, may include a thrombogenic agent that may be eluted therefrom, and particularly, eluted into the vascular defect. For some embodiments, the inner layer and outer layer may be secured together in a monolithic structure. For some embodiments, the permeable layer may include a thin membrane having a combination of macropores and micropores. For some embodiments, the macropores may have a transverse dimension of about 100 microns to about 500 microns and the micropores have a transverse dimension of about 10 microns to about 100 microns.

Some embodiments may include a sealing member (not shown) disposed about a perimeter of the permeable layer and configured to form a seal between the permeable layer and a surface of the patient's vasculature. Some embodiments of the sealing member may include a swellable polymer. For some embodiments, a total volume of the permeable layer may be less than about 5 mm3. For some embodiments, a total volume of permeable layer may be between about 0.5 mm3 and 4 mm3. For some embodiments, the permeable layer may have a porosity greater than about 60 percent and a thickness of less than about 50 microns. For some embodiments, the permeable layer may be about 2 microns to about 10 microns thick. For some embodiments, the expandable body of the support structure may have a first transverse dimension in a collapsed state configured for intraluminal delivery of about 0.2 mm to about 2 mm and a second transverse dimension in an expanded relaxed state after deployment or delivery of about 4 mm to about 30 mm.

A delivery system, such as any suitable embodiment of the delivery systems discussed and incorporated herein, may be used that allows for accurate positioning such that the defect spanning structure 108 substantially covers the defect opening or neck as shown in FIG. 16. The device 100 may be implanted substantially in a blood vessel 104 with the defect or "parent vessel". However, in some embodiments, a portion of the device 100 may extend into the defect opening or neck or into branch vessels. In some embodiments, the support structure comprises strut members that cross or span the lumen of the parent vessel both upstream and/or downstream of the vascular defect 106. Axial movement and deployment of the device 100 from a delivery system that includes a microcatheter 110 may be controlled by an elongate actuator member 112 that extends from a proximal end of the microcatheter 110 to a distal end thereof. The actuator 112 may also include a release mechanism 114 disposed on a distal end thereof that releasably secures a distal end of the actuator member 112 to the device. The release mechanism 114 may include any suitable embodiment of release or detachment mechanisms discussed herein.

Figure 19:
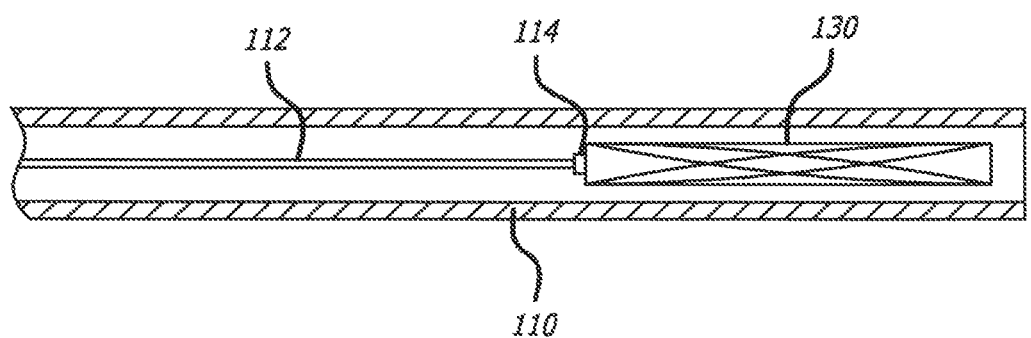
FIG. 19 shows the device of FIG. 18 disposed in a microcatheter in a collapsed radially constrained state.

FIG. 18 illustrates an embodiment of a device for treatment of a patient's vasculature 130 that has a similar configuration to that of the device 100 illustrated in FIGS. 16 and 17. The device for treatment of a patient's vasculature 130 is shown in an expanded deployed state in FIG. 18 with the support structure 132 of the device 130 engaged with the patient's vascular tissue of the vessel 104 adjacent the vascular defect 106. The support structure 132 of the device includes strut members configured to span or cross the lumen of a parent vessel both upstream and downstream of the vascular defect 106 shown in the form of a berry aneurysm extending from the parent vessel 104. The struts of the support structure may include undulated portions that are configured to elastically absorb axial compression and extension. A defect spanning structure 134 of the device is configured to substantially block flow of blood into the vascular defect 106 when positioned substantially over the defect as shown. The expandable body support structure 132 includes a low profile radially constrained state as shown in FIG. 19 that is suitable for delivery to a target vascular defect within a patient's body from a delivery system, such as the delivery system embodiments discussed herein. Some such delivery system embodiments may include one or more microcatheters 110, guidewires as well as other devices.

The support structure 132 further includes a first end, a second end and an elongated tubular configuration having a longitudinal axis. The elongate flexible struts are connected or otherwise secured at intersections between the first end and second end forming a plurality of open cells between struts in a middle portion of the expandable body. The elongated tubular configuration has a first transverse dimension in a radially compressed state that is suitable for delivery from a microcatheter 110 configured for navigation in a patient's cerebral vasculature as shown in FIG. 19.

The tubular configuration has an expanded relaxed state with a tubular configuration having a second transverse dimension substantially greater than the first transverse dimension of the tubular configuration of the constrained state which is configured to engage tissue of a patient's vasculature adjacent a vascular defect 106 as shown in FIG. 18. The elastic resiliency of the support structure 132 may be achieved by an appropriate selection of materials, such as superelastic alloys, including nickel titanium alloys, stainless steel, or any other suitable material. The defect spanning structure 134 of the device is integrally formed from the same material as the support structure 132 and includes a high density porous region that is configured to be disposed against the opening to the vascular defect 106 so as to close off the opening to the vascular defect as shown in FIG. 18. The defect spanning structure 134 may be coated with a variety of materials including any of the coating, bioactive or polymer materials discussed above.

Some embodiments may include a sealing member (not shown) disposed about a perimeter of the defect spanning structure and configured to form a seal between the permeable layer and a surface of the patient's vasculature. Some embodiments of the sealing member may include a swellable polymer. For some embodiments, the permeable layer may have a porosity greater than about 60 percent. For some embodiments, the support structure 132 may have a first transverse dimension in a collapsed state of about 0.2 mm to about 2 mm and a second transverse dimension of about 4 mm to about 30 mm.

Figure 20:
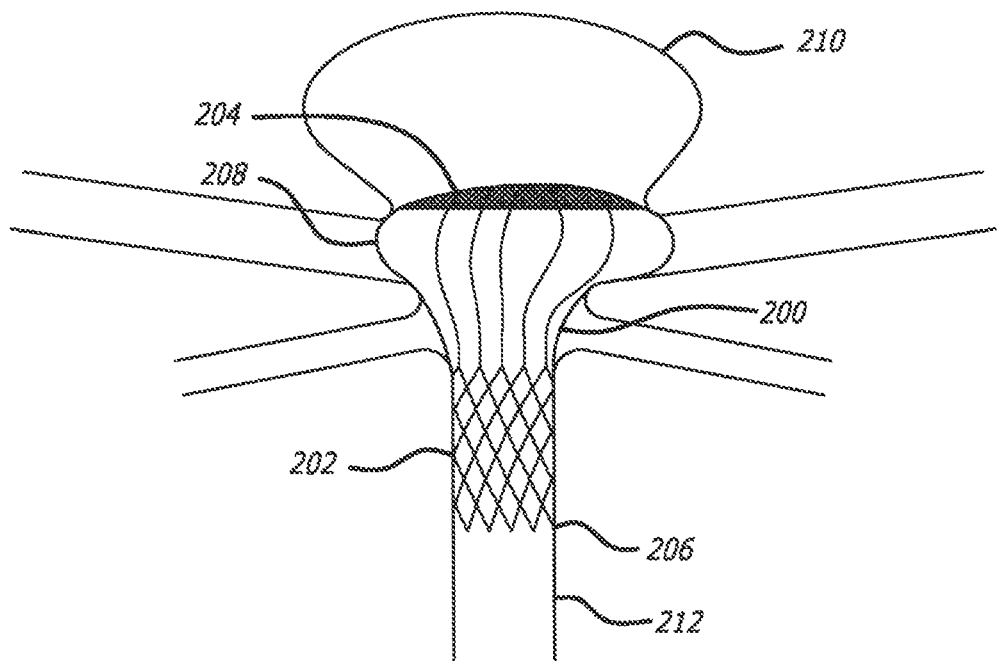
FIG. 20 is a sectional view of a terminal aneurysm with an embodiment of a device for treatment of a patient's vasculature deployed adjacent the aneurysm.
Figure 21:
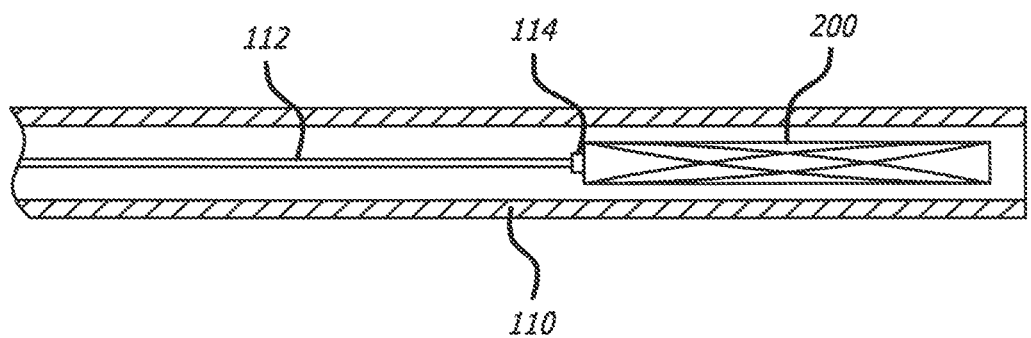
FIG. 21 shows the device of FIG. 20 disposed within a microcatheter in a collapsed radially constrained state.

FIG. 20 illustrates a device for treatment of a patient's vasculature 200 that includes a support structure 202 and a defect spanning structure 204. The support structure 202 includes an expandable body with a first end 206 and a second end 208. The defect spanning structure 204 is disposed at the second end of the expandable body and may include a permeable layer which conforms to a profile of the second end 208 of the expandable body in a relaxed expanded state. When in a relaxed, expanded state, as when deployed in a vascular defect such as terminal aneurysm 210, the first end portion of the expandable body has a tubular configuration, which may be engaged with a parent vessel 212, and the second end portion has a somewhat bulbous or spherical configuration. Second ends of the struts of the expandable body may be secured together relative to each other. The expandable body also has a low profile radially constrained state, as shown in FIG. 21, with an elongated tubular configuration that includes a longitudinal axis with the elongate flexible struts of the second end portion disposed substantially parallel to each other. The radial constraint on the device 200 may be applied by an inside surface of the inner lumen of the microcatheter 110, or it may be applied by any other suitable mechanism that may be released in a controllable manner upon ejection of the device from the distal end of the catheter. For example, a severable band or fiber may constrain the device until severed by the application of energy (e.g., heat) or mechanical means.

The bulbous second end portion of the expandable body has a first transverse dimension with a low profile suitable for delivery from a microcatheter 110 and an expanded relaxed state having an axially shortened configuration relative to the constrained state with each strut forming a smooth arc such that the arc of each strut extends axially beyond the first transverse dimension. In the expanded state the second end portion has a second transverse dimension substantially greater than the first transverse dimension. One or more of the struts may be configured to independently flex in a radial orientation with respect to the longitudinal axis of the expandable body.

The tubular configuration of the first end 206 of the expandable body may include a trunk portion with an open upstream end that extends into and engages one of the patient's vessels, which may include the parent vessel 212. For some embodiments, the trunk portion may be deployed to extend into the parent vessel of a terminal bifurcation such that the bulbous second end portion of the device is positioned at an apex portion of the bifurcation as shown in FIG. 20. Such embodiments may be useful for the treatment of basilar tip aneurysm embodiments. The engagement of the tubular portion of the first end portion 206 of the support structure 202 may be achieved by the exertion of an outward radial force against tissue of the patient's vessel 212 of the tubular support structure. Such a force may be exerted in some embodiments wherein the nominal outer transverse dimension or diameter of the support structure in the relaxed unconstrained state is larger than the nominal inner transverse dimension of the vessel within which the support structure is being deployed. The elastic resiliency of the support structure 202 may be achieved by an appropriate selection of materials, such as superelastic alloys, including nickel titanium alloys, stainless steel, or any other suitable material.

Embodiments of the permeable layer of the defect spanning structure 204 may include a convex configuration that spans the second end of the expandable body in a relaxed expanded state and extends along the struts towards the first end. In some embodiments, the permeable layer may span the struts of the support structure towards the first end to a longitudinal position of about 10 percent to about 60 percent the total length of the expandable body when the expandable body is in a relaxed expanded state. The defect spanning structure 204 may include any of the materials discussed above including perforated membranes, laser cut polymer membranes, microfibers, including electrospun microfibers, as well as others. The defect spanning structure may be secured to the support structure by adhesive bonding, suturing, lacing, or any other suitable method.

For some embodiments, the struts of the expandable body 202 may include perforations which are configured for securing the permeable layer to the expandable body by lacing, suturing or the like. The defect spanning structure 204 in the form of a permeable layer may be disposed interior to an outer surface of the expandable body. The defect spanning structure may also include multiple layers. For some multiple layer embodiment, an outer layer may include an anti-thrombogenic agent and an inner layer disposed towards a cavity of a the vascular defect, such as the aneurysm shown, may include a thrombogenic agent that may be eluted therefrom, and particularly, eluted into the vascular defect to promote thrombosis, stabilization or healing of the vascular defect. For some embodiments, the inner layer and outer layer may be secured together in a monolithic structure. For some embodiments, the permeable layer may include a thin membrane having a combination of macropores and micropores. For some embodiments, the macropores may have a transverse dimension of about 100 microns to about 500 microns and the micropores have a transverse dimension of about 10 microns to about 100 microns.

For some embodiments, a total volume of the permeable layer may be less than about 5 mm3. For some embodiments, a total volume of permeable layer may be between about 0.5 mm3 and 4 mm3. For some embodiments, the permeable layer may have a porosity greater than about 60 percent and a thickness of less than about 50 microns. For some embodiments, the permeable layer may be about 2 microns to about 10 microns thick. For some embodiments, the expandable body of the support structure may have a first transverse dimension in a collapsed state of about 0.2 mm to about 2 mm and a second transverse dimension in a relaxed deployed state of about 4 mm to about 30 mm. Some embodiments of the device 200 may include a sealing member (not shown) disposed about a perimeter or other suitable portion of the permeable layer, or defect spanning structure 204 generally, and be configured to form a seal between the permeable layer and a surface of the patient's vasculature. Some embodiments of the sealing member may include a swellable polymer.

A delivery system, such as the delivery systems discussed above, may be used that allows for accurate positioning such that the defect spanning structure 204 substantially covers the defect opening or neck of the vascular defect as shown in FIG. 20. The device 200 may be implanted substantially in a blood vessel with the defect or parent vessel 212. However, in some embodiments, a portion of the device may extend into the defect opening or neck or into branch vessels. In some embodiments, the support structure 202 includes strut members that cross or span the lumen of the parent vessel both upstream and/or downstream of the vascular defect. Axial movement and deployment of the device from the microcatheter 110 may be controlled by an actuator member 112 and release mechanism 114 that releasably secures the actuator member to the device 200 as shown in FIG. 21. The release mechanism may include any suitable embodiment of release mechanisms discussed above.

Figure 22:
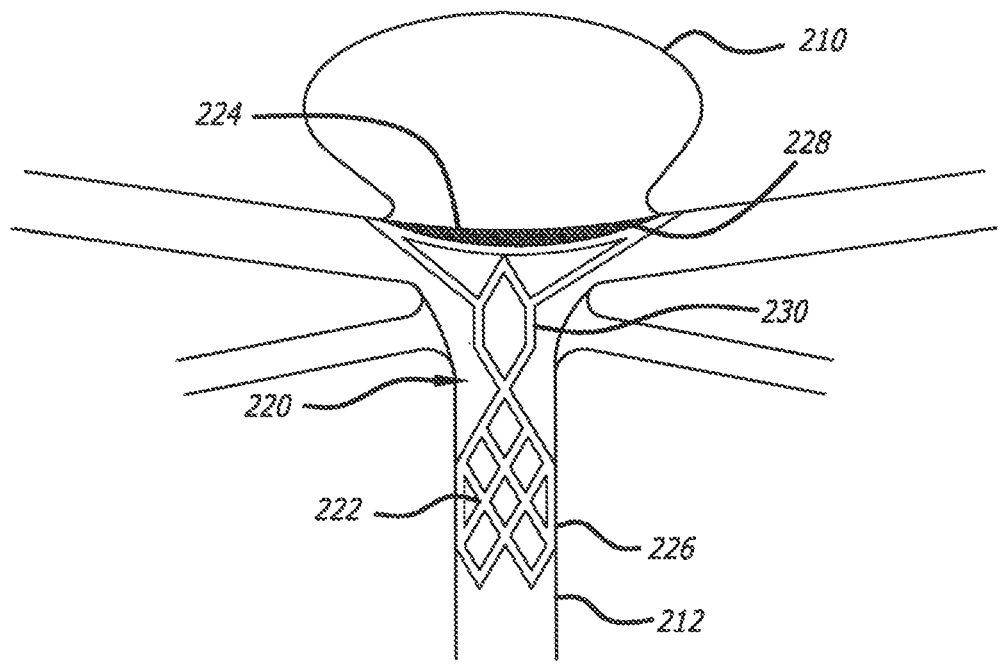
FIG. 22 is a sectional view of a terminal aneurysm with an embodiment of a device for treatment of a patient's vasculature deployed adjacent the aneurysm.
Figure 23:
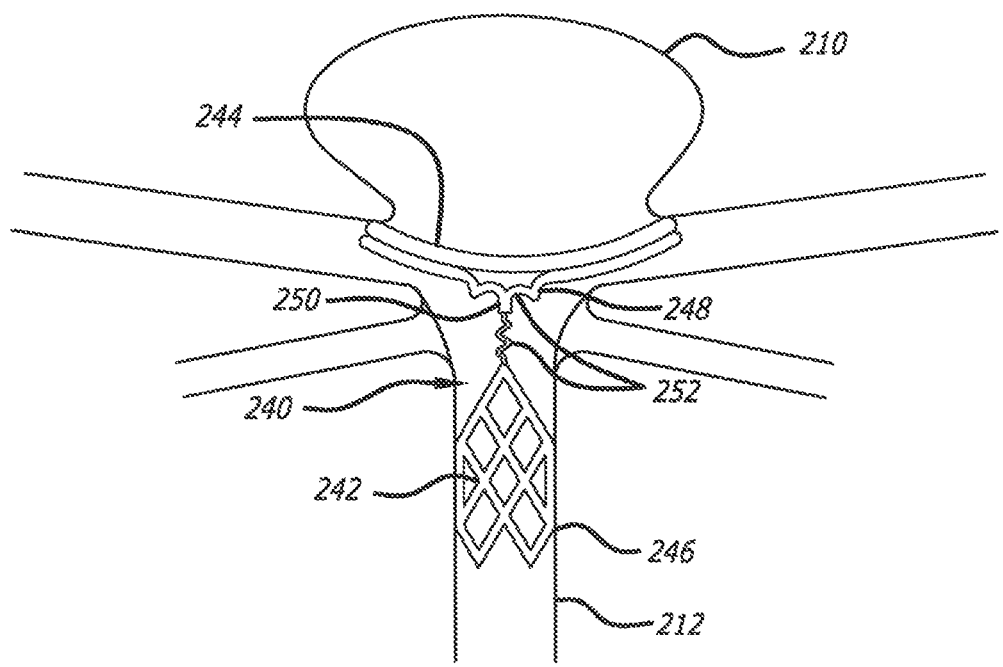
FIG. 23 is a sectional view of a terminal aneurysm with an embodiment of a device for treatment of a patient's vasculature deployed adjacent the aneurysm.

FIGS. 22 and 23 show embodiments of devices for treatment of a patient's vasculature that have configurations that are similar in some respects to the device of FIGS. 20 and 21. However, the embodiments of FIGS. 22 and 23 include a generally tubular support structure, a defect spanning structure that has at least some surface substantially perpendicular to an axis of the support structure and a connecting structure which connects the support structure to the defect spanning structure as shown in FIG. 22. The connecting structure and defect spanning structure may include one or more flexible elements to facilitate conformance of the defect spanning structure to anatomical variations of the patient's vasculature adjacent the vascular defect to be treated as shown in FIG. 23. Variations in the patient's vasculature may include angular deviations, dimensional deviations, off axis vascular defects and the like.

FIG. 22 illustrates an embodiment of a device for treatment of a patient's vasculature 220 including a support structure 222 and a defect spanning structure 224. The support structure 222 includes an expandable body with a first end 226 and a second end 228. The defect spanning structure 224 is disposed at the second end 228 of the expandable body and may include a permeable layer which conforms to a profile of a second end platform of the expandable body in a relaxed expanded state. When in a relaxed, expanded state, the first end portion of the expandable body has a tubular configuration. The second end platform is coupled to the tubular first end portion by a connecting structure 230 in the form of strut members. The expandable body has a low profile radially constrained state (not shown) with an elongated configuration. When the device 220 is in a collapsed, radially constrained state, as discussed above with regard to other embodiments and shown in FIG. 22A, the radial constraint on the device 220 may be applied by an inside surface of an inner lumen of a microcatheter 110, or it may be applied by any other suitable mechanism that may be released in a controllable manner upon ejection of the device from the distal end of the catheter 110.

Referring to FIG. 23, the device for treatment of a patient's vasculature 240 is shown that includes a support structure 242 and a defect spanning structure 244. The support structure 242 includes an expandable body with a first end 246 and a second end 248. The defect spanning structure 244 is disposed at the second end 248 of the expandable body and may include a permeable layer which conforms to a profile of a second end platform of the expandable body when the device is in a relaxed expanded state. When in a relaxed, expanded state, the first end portion of the expandable body may have a substantially tubular configuration.

The second end platform is coupled to the tubular first end portion by a connecting structure 250 in the form of a flexible coupling that extends generally along the longitudinal axis of the expandable body member. The flexible coupling may include one or more flexing members 252. The second end platform of the expandable body may be nominally disposed substantially perpendicular to the longitudinal axis of the tubular first end portion of the expandable body in a relaxed state but is configured to flex or otherwise deflect at the flexible coupling in any angular orientation or direction perpendicular to the longitudinal axis in order to accommodate a patient's anatomical variations. For some embodiments, the second end platform of the defect spanning structure may flex over an angle of up to about 40 degrees from perpendicular with the longitudinal axis of the first end tubular portion, more specifically, up to about 20 degrees from perpendicular with the longitudinal axis of the first end tubular portion of the device.

The engagement of the tubular portion of the first end portion of the support structure 242 may be achieved by the exertion of an outward radial force against tissue of the patient's vessel 212 of the tubular support structure. Such a force may be exerted in some embodiments wherein the nominal outer transverse dimension or diameter of the first end tubular portion of the support structure 242 in the relaxed unconstrained state is larger than the nominal inner transverse dimension of the vessel within which the support structure is being deployed. The elastic resiliency of the support structure may be achieved by an appropriate selection of materials, such as superelastic alloys, including nickel titanium alloys, stainless steel, or any other suitable material.

Embodiments of the defect spanning structure 244 and permeable layer thereof may include a convex configuration that spans the second end platform portion of the expandable body. The second end platform portion may include one or more strut or frame members that may be made from the same or a similar material as the material of the first end tubular portion of the device. The struts or frame members of the second end platform as well as the flexible coupling member 250 may also be a continuous or monolithic structure with respect to the first end tubular portion and support structure 242 generally. In some embodiments, the permeable layer and defect spanning structure 244 may have a major transverse dimension across the outer surface of the platform of about 4 mm to about 30 mm. The defect spanning structure 244 may include any of the materials discussed above including perforated membranes, laser cut polymer membranes, microfibers, including electrospun microfibers, as well as others. The defect spanning structure 244 may be secured to the strut or frame members of the second end platform by adhesive bonding, suturing, lacing, or any other suitable method.

For some embodiments, the struts of the second end platform portion may include perforations which are configured for securing the permeable layer to the expandable body by lacing, suturing or the like. The permeable layer of the defect spanning structure 244 may be disposed on either side of the frame or strut members of the second end platform. The defect spanning structure 244 may also include multiple layers. For some multiple layer embodiments, an outer layer which is exposed to a patient's vasculature system includes an anti-thrombogenic agent. An inner layer disposed towards a cavity of a vascular defect, such as the aneurysm shown, may include a thrombogenic agent that may be eluted therefrom, and particularly, eluted into the vascular defect. For some embodiments, the inner layer and outer layer may be secured together in a monolithic structure. For some embodiments, the permeable layer may include a thin membrane having a combination of macropores and micropores. For some embodiments, the macropores may have a transverse dimension of about 100 microns to about 500 microns and the micropores have a transverse dimension of about 10 microns to about 100 microns.

For some embodiments, a total volume of the permeable layer may be less than about 5 mm3. For some embodiments, a total volume of permeable layer may be between about 0.5 mm3 and 4 mm3. For some embodiments, the permeable layer may have a porosity greater than about 60 percent and a thickness of less than about 50 microns. For some embodiments, the permeable layer may be about 2 microns to about 10 microns thick. For some embodiments, the expandable body of the support structure may have a first transverse dimension in a collapsed state of about 0.2 mm to about 2 mm and a second transverse dimension in a relaxed state of about 4 mm to about 30 mm. Some embodiments of the device 240 may include a sealing member (not shown) disposed about a perimeter or other suitable portion of the permeable layer, or defect spanning structure 244 generally, and be configured to form a seal between the permeable layer and a surface of the patient's vasculature. Some embodiments of the sealing member may include a swellable polymer.

Figure 22A:
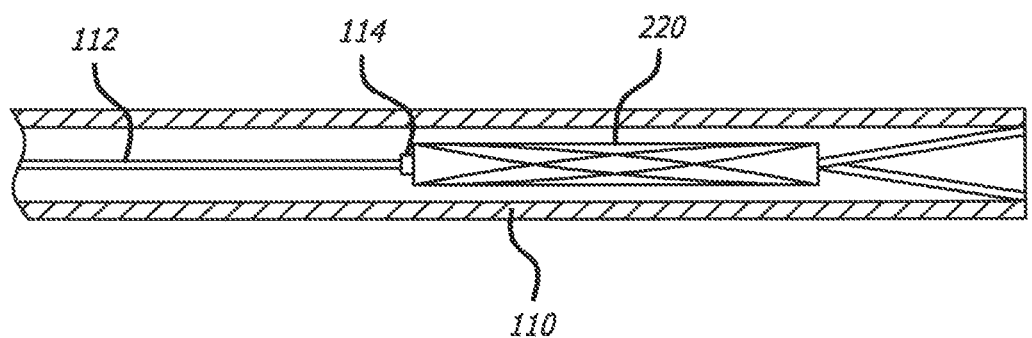
FIG. 22A shows the device of FIG. 22 disposed within a microcatheter in a collapsed radially constrained state.
Figure 24:
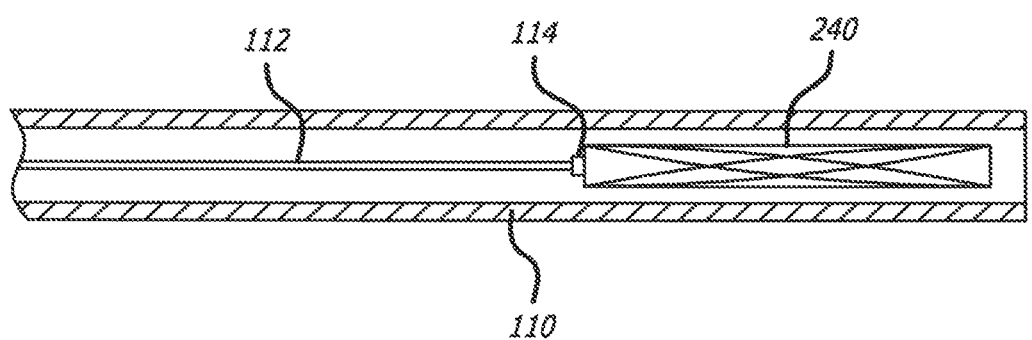
FIG. 24 shows the device of FIG. 23 disposed within a microcatheter in a collapsed radially constrained state.

Delivery systems and methods, such as any of the delivery systems and methods discussed herein, may be used to deliver either of the device embodiments shown in FIGS. 22 and 23. The devices of FIGS. 22 and 23 may be delivered by microcatheter embodiments 110 when disposed in a collapsed radially constrained state as shown in FIGS. 22A and 24, respectively. Such delivery devices and methods allow for accurate positioning such that the defect spanning structure substantially covers the defect opening or neck as shown in FIGS. 22 and 23. The device may be implanted substantially in a blood vessel with the defect 210 or parent vessel 212. However, in some embodiments, a portion of the device may extend into the defect opening or neck or into branch vessels.

Figure 25:
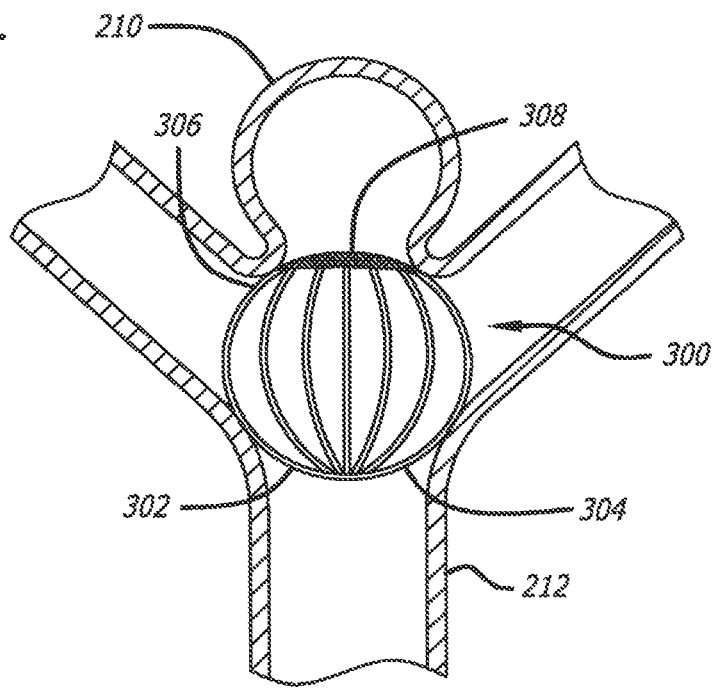
FIG. 25 is a sectional view of a terminal aneurysm with an embodiment of a device for treatment of a patient's vasculature deployed adjacent the aneurysm.

Referring to FIG. 25, a device for treatment of a patient's vasculature 300 is shown that includes a support structure 302 that includes an expandable body with a first end 304 and a second end 306. A defect spanning structure 308 is disposed at the second end 306 of the expandable body and may include a permeable layer which conforms to a profile of the second end of the expandable body when the expandable body is in a relaxed expanded state. When in a relaxed, expanded state, the expandable body may have a substantially spherical or globular shape with a first end portion of the expandable body 302 having a substantially hemispherical configuration and a second end portion also has a somewhat bulbous or hemispherical configuration. First ends and second ends of the struts of the expandable body may be secured together relative to each other and allow the ends to pivot relative to each other so as to allow expansion of the expandable body.

Figure 26:
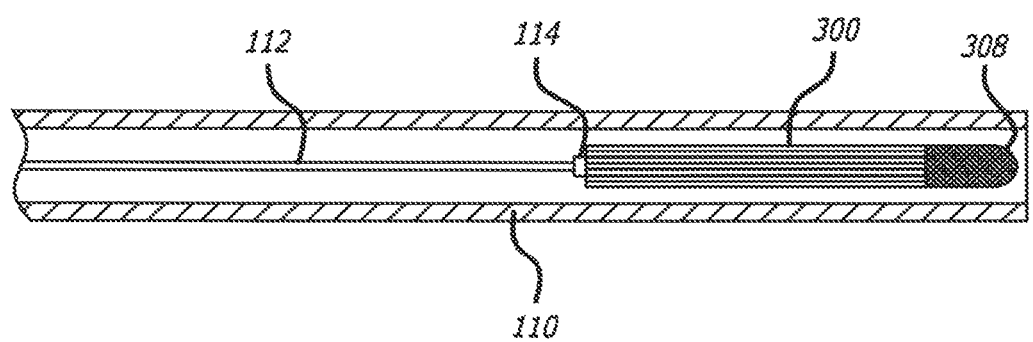
FIG. 26 shows the device of FIG. 25 disposed within a microcatheter in a collapsed radially constrained state.

The expandable body also has a low profile radially constrained state, as shown in FIG. 26, with an elongated configuration that includes a longitudinal axis. In the collapsed, radially constrained state, the elongate flexible struts of the expandable body may be disposed substantially parallel to each other. The radial constraint on the device may be applied by an inside surface of the inner lumen of a microcatheter 110, such as the distal end portion of the microcatheter shown in FIG. 26, or it may be applied by any other suitable mechanism that may be released in a controllable manner upon ejection of the device from the distal end of the catheter 110 to allow outward self-expansion of the expandable body and device 300.

Embodiments of the support structure 302 form a spherical, bulbous or globular structure. The defect spanning structure 308 may have low porosity, small pores or no porosity at all and a second portion that is fenestrated or open-celled and highly porous to blood flow. The structure 302 may include strut members made of wire or cut from sheet or tube stock. While the device 300 may have a substantially spherical, bulbous or globular shape in its natural, relaxed, undeformed or minimum energy state, the structure may be compliant to conform to various vessel anatomy; thus, the shape after implantation may have deviations from its natural shape. The portion of device 300 surface area that is of lower or no porosity may be less than about 25% of the total surface area. The support structure 302 may be substantially hollow. The device may be deployed such that the defect spanning portion 308 is positioned substantially covering the opening or neck of a vascular defect 210 as shown in FIG. 25. The device may be particularly useful in the treatment of bifurcation aneurysms or terminal aneurysms 210 that lie at the junction or terminus where a vessel 212 is branching into two vessels. When the device is used to treat a terminal aneurysm 210, the device structure may be placed at the junction of the three vessels making up the bifurcation and at least one strut member crosses or spans the lumen of all three vessels. For some embodiments, the support structure 302 may define a substantially closed structure with at least one diameter that is greater than the largest vessel of those proximate an aneurysm 210.

The bulbous or hemispherical second end portion of the expandable body has a first transverse dimension with a low profile suitable for delivery from a microcatheter 110. The expandable body has a second transverse dimension or diameter when in an expanded relaxed state having an axially shortened configuration relative to the constrained state with each strut forming a smooth arc such that the arc of each strut extends axially beyond the first transverse dimension. In the expanded state the second end portion has a second transverse dimension substantially greater than the first transverse dimension. One or more of the struts may be configured to independently flex in a radial orientation with respect to the longitudinal axis of the expandable body. The hemispherical configuration of the first end 304 of the expandable body 302 may extend into and engage one of the patient's vessels, which may include the parent vessel 212. The bulbous second end portion of the device is positioned at an apex portion of the bifurcation as shown in FIG. 25 with the defect spanning structure 308 engaged with and isolating the vascular defect 210 in the form of the terminal aneurysm shown. Such embodiments may be useful for the treatment of basilar tip aneurysm embodiments.

The engagement of the bulbous portion of the first end portion of the support structure 302 may be achieved by the exertion of an outward radial force against tissue of the patient's vessel of the support structure. Such a force may be exerted in some embodiments wherein the nominal outer transverse dimension or diameter of the support structure 302 in the relaxed unconstrained state is larger than the nominal inner transverse dimension of the vessel within which the support structure is being deployed. The elastic resiliency of the support structure may be achieved by an appropriate selection of materials, such as superelastic alloys, including nickel titanium alloys, stainless steel, or any other suitable material.

Embodiments of a permeable layer of the defect spanning structure 308 may include a convex configuration that spans the second end of the expandable body in a relaxed expanded state and extends along the struts towards the first end. In some embodiments, the permeable layer may span the struts towards the first end to a longitudinal position of about 10 percent to about 60 percent the total length of the expandable body when the expandable body is in a relaxed expanded state. The defect spanning structure 308 may include any of the materials discussed above including perforated membranes, laser cut polymer membranes, microfibers, including electrospun microfibers, as well as others. The defect spanning structure may be secured to the support structure by adhesive bonding, suturing, lacing, or any other suitable method.

For some embodiments of the device 300, the struts of the expandable body of the support structure 302 may include perforations which are configured for securing the permeable layer to the expandable body by lacing, suturing or the like. The defect spanning structure 308 may include a permeable layer which may be disposed interiorly or exteriorly to an outer surface or structure of the expandable body. The defect spanning structure 308 may also include multiple layers. For some such multiple layer embodiments, an outer layer of the permeable layer may include an anti-thrombogenic agent and an inner layer disposed towards the vascular defect 210, such as the aneurysm shown, may include a thrombogenic agent that may be eluted therefrom. The thrombogenic agent eluted from the inner layer, and particularly, eluted into the vascular defect, may promote thrombosis, stabilization or healing of the vascular defect. For some embodiments, the inner layer and outer layer may be secured together in a monolithic structure. For some embodiments, the permeable layer may include a thin membrane having a combination of macropores and micropores. For some embodiments, the macropores may have a transverse dimension of about 100 microns to about 500 microns and the micropores have a transverse dimension of about 10 microns to about 100 microns.

For some embodiments, a total volume of the permeable layer of the defect spanning structure 308 may be less than about 5 mm3. For some embodiments, a total volume of permeable layer may be between about 0.5 mm3 and 4 mm3. For some embodiments, the permeable layer may have a porosity greater than about 60 percent and a thickness of less than about 50 microns. For some embodiments, the permeable layer may be about 2 microns to about 10 microns thick. For some embodiments, the expandable body of the support structure 302 may have a first transverse dimension in a collapsed radially constrained state of about 0.2 mm to about 2 mm and a second transverse dimension in a relaxed expanded state of about 4 mm to about 30 mm. Some embodiments of the device 300 may include a sealing member (not shown) disposed about a perimeter or other suitable portion of the permeable layer, or defect spanning structure 308 generally, and be configured to form a seal between the permeable layer and a surface of the patient's vasculature. Some embodiments of the sealing member may include a swellable polymer.

A delivery system, such as the delivery systems discussed above, may be used that allows for accurate positioning such that the defect spanning structure substantially covers the defect opening or neck as shown in FIG. 25. The device may be implanted or deployed substantially in a blood vessel 212 adjacent the defect 210. However, in some embodiments, a portion of the device 300 may extend into the defect opening or neck or into branch vessels. Axial movement and deployment of the device 300 from the microcatheter 110 may be controlled by an actuator member 112 and release mechanism 114 that releasably secures the actuator member to the device as shown in FIG. 26. The delivery systems, methods and release mechanisms suitable for use with the device of FIG. 25 may include any suitable embodiment or embodiments discussed or incorporated herein.

In use, the device 300 shown in FIG. 25, or any other suitable device embodiment discussed herein, may be deployed by advancing a delivery system, such as the delivery system discussed above, or any other suitable delivery system discussed or incorporated herein, to a position adjacent a vascular defect 210 to be treated. The device 300 may then be positioned adjacent the vascular defect 210 such as the aneurysm shown and deployed such that the expandable body self-expands adjacent the vascular defect and the defect spanning structure 308 covers at least a portion of the defect opening or neck. For some embodiments, the device 300 is positioned adjacent the vascular defect 210 from a proximal end of the delivery system with an elongate actuator 112 which may be releasably secured to the device and further comprising releasing or detaching the device from the elongate actuator. The device 300 may be released or detached from the delivery system by any suitable detachment mechanism or mechanisms. For example, thermal, mechanical, electrolytic, shape memory as well as any other suitable mechanism or mechanisms may be used.

During deployment, the device 300 may be rotated in order to achieve a desired position prior to or during deployment of the device. For some embodiments, the device may be rotated about a longitudinal axis of the delivery system with or without the transmission or manifestation of torque being exhibited along a middle portion of a delivery catheter 110 being used for the delivery. Suitable catheters for such use have been described and incorporated herein. These delivery and deployment methods may be used for deployment within berry aneurysms, terminal aneurysms, or any other suitable vascular defect embodiments.

Some method embodiments include deploying the device at a confluence of three vessels of the patient's vasculature that form a bifurcation such that the defect spanning structure substantially covers the neck of a terminal aneurysm and one or more struts of the support structure span or cross each of the three vessels.

For some embodiments, once the device 300 has been deployed, the attachment of platelets to the defect spanning structure may be inhibited and the formation of clot within an interior space of the vascular defect promoted or otherwise facilitated with a suitable choice of thrombogenic coatings, anti-thrombogenic coatings or any other suitable coatings applied either to the defect spanning structure or support structure adjacent thereto. Energy forms may also be applied through the delivery apparatus and/or a separate catheter to facilitate fixation and/or healing of the device adjacent the vascular defect for some embodiments. One or more embolic devices or embolic material may also optionally be delivered into the vascular defect adjacent the defect spanning structure after the device has been deployed.

Figure 27:
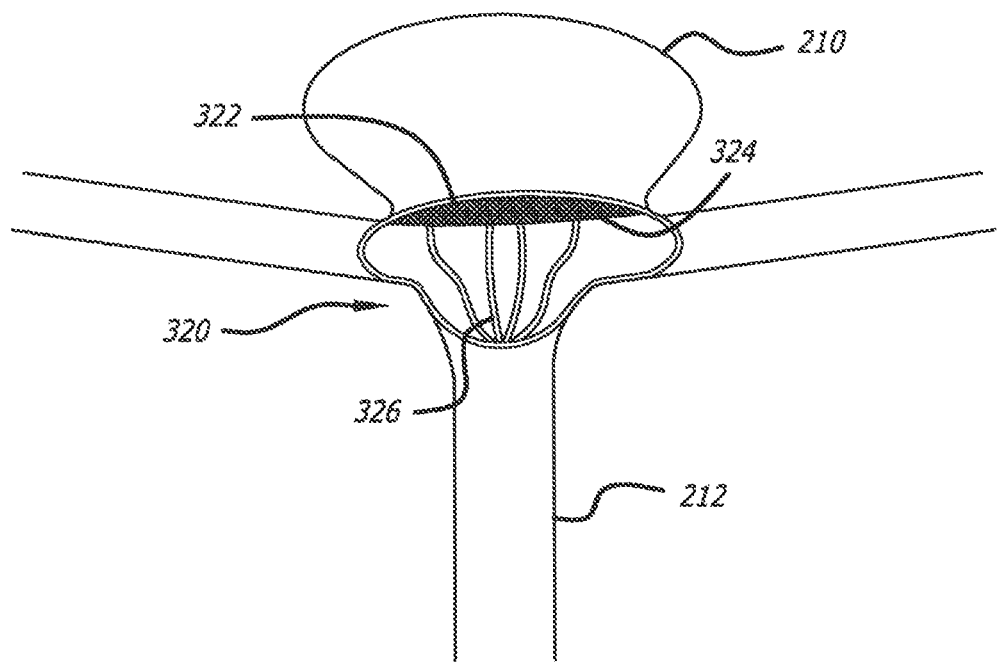
FIG. 27 is a sectional view of a terminal aneurysm with an embodiment of a device for treatment of a patient's vasculature deployed adjacent the aneurysm.

FIG. 27 illustrates an embodiment of a device for treatment of a patient's vasculature 320 that may have the same or similar features, dimensions and materials as those of the device of FIG. 25. The device 320 of FIG. 27 is shown with at least a portion of the defect spanning structure 322 forming a convex surface 324 that generally approximates the natural healthy vessel anatomy and with the first end of the defect spanning structure engaging the patient's anatomy so as to push the defect spanning portion 322 of the device against the opening of the patient's vascular defect 210 so as to isolate the defect the interior of the patient's vasculature. The support structure 326 may have a configuration that conforms to the vasculature adjacent the vascular defect 210.

Figure 28:
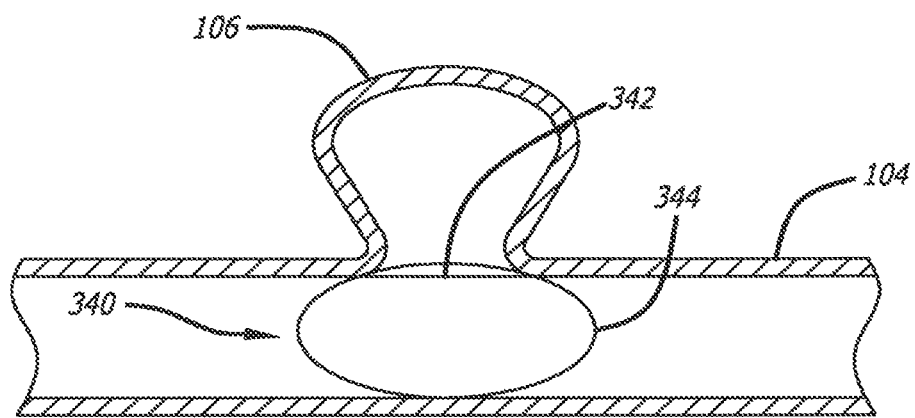
FIG. 28 shows a view in longitudinal section of an aneurysm with an embodiment of a device for treatment of a patient's vasculature deployed adjacent the aneurysm.

FIG. 28 illustrates an embodiment of a device for treatment of a patient's vasculature 340 that may have the same or similar features, dimensions and materials as those of the device of FIG. 25. The embodiment shown forms a bulbous or globular device being used in the treatment of the side-wall aneurysms and may also be used to treat aneurysms occurring at or near bifurcations but not "terminal". The device 340 in FIG. 28 is shown engaged with and isolating a typical berry type aneurysm 106 with the defect spanning structure 342 of the device spanning and isolating the vascular defect 106. In some embodiments, the device 340 may include a support structure 344 having an ovoid or elliptical cross-section and a defect spanning portion 342 that lies along a side wall as shown in FIG. 28.

Figure 31:
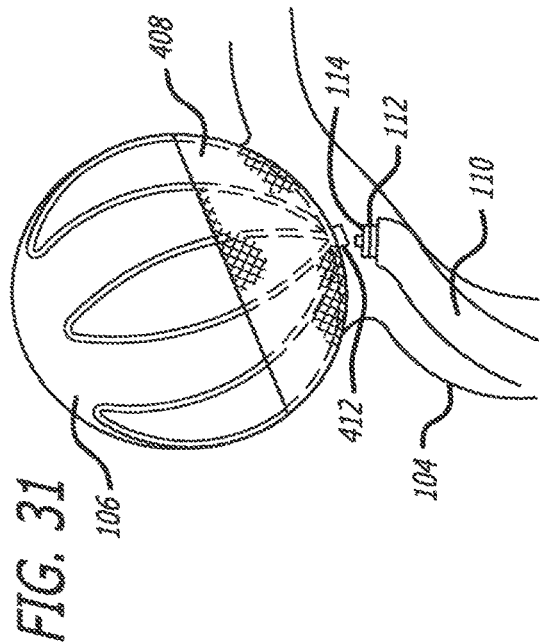
FIG. 31 is a sectional view of an aneurysm with an embodiment of a device for treatment of a patient's vasculature deployed within the aneurysm.

Referring to FIGS. 29-32, an embodiment of an intrasaccular device for treatment of a patient's vasculature 400 is shown that is configured to be deployed within an interior cavity of a patient's vascular defect. The device may have the same or similar features, dimensions and materials as those of the devices shown in FIGS. 25, 27 and 28 and discussed above. The device 400 may be used to treat either a side-wall or berry aneurysm 106 as shown in FIG. 31 or a bifurcation aneurysm, such as the terminal aneurysm 210 shown in FIG. 32. The device 400 may be disposed substantially within the vascular defect when deployed and implanted, however, in some embodiments, a portion of the device may extend into the neck or parent vessel.

Figure 29:
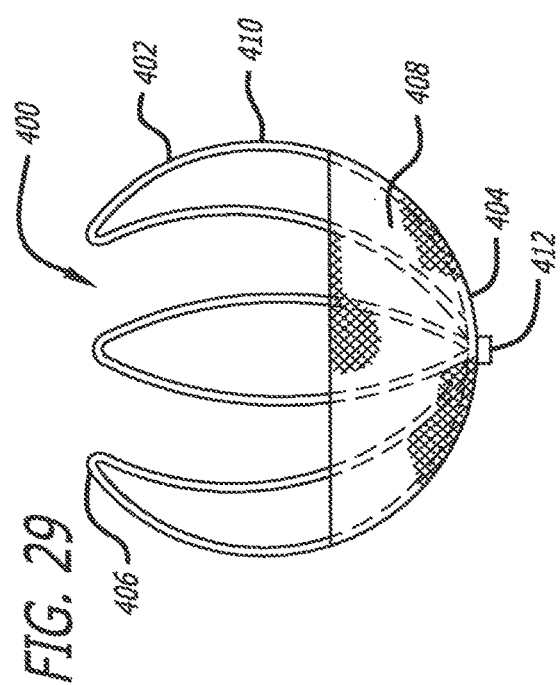
FIG. 29 illustrates an elevation view of an embodiment of a device for treatment of a patient's vasculature.

Referring to FIG. 29, the device for treatment of a patient's vasculature 400 is shown that includes a support structure 402 with an expandable body with a first end 404 and a second end 406. A defect spanning structure 408 is disposed at the first end of the expandable body and may include a permeable layer which conforms to a profile of the first end of the expandable body when the expandable body is in a relaxed expanded state. When in a relaxed, expanded state, the expandable body may have a substantially spherical or globular shape with a first end portion of the expandable body having a substantially hemispherical configuration. The second end portion also has a somewhat bulbous or hemispherical configuration, however, the second end portion and second ends of the struts 410 of the expandable body are not all secured together relative to each other and each second end of the struts of the expandable body are able to flex in a resilient manner substantially independent of other struts of the expandable body. The struts 410 of the expandable body are coupled at the first end 404 of the device to a hub portion or connection 412 that is disposed along a longitudinal axis of the expandable body. Each strut 410 forms a loop or leaflet portion that begins at the hub portion 412 and extends in a curving arc, which may take a spherical or bulbous shape, towards the second end. The struts form an apex at the second end and curves back to the hub with a curving arc to the hub portion. Each leaflet portion of the expandable body portion is capable of substantially independent flexing in an inward or outward radial direction.

As discussed, embodiments of the support structure 402 may form a spherical, bulbous or globular structure including the defect spanning portion 408. Embodiments of the defect spanning structure 408 may have a first portion with a low porosity, small pores or no porosity at all and a second portion that is fenestrated or open-celled and highly porous to blood flow. The expandable body of the support structure may include strut members 410 made of wire or cut from sheet or tube stock as well as other suitable materials. The surface area of the portion of device that is of lower or no porosity may be less than about 25% of the total surface area of the defect spanning structure 408. When placed in a vascular defect such as a cerebral aneurysm, the higher density portion reduces the flow into the aneurysm and encourages the formation of clot and thrombus. The higher density portion may be formed by a network of fibers, strands, wires or filaments. They may be on the outside, inside or integrally combined within the strut members. Preferably, the fibers are less than about 0.20 mm in diameter or thickness. Preferably the fibers are between about 10 and 100 microns. In one embodiment, they may be formed of nanofibers. The support structure 402 may be substantially hollow for some embodiments.

Figure 30:
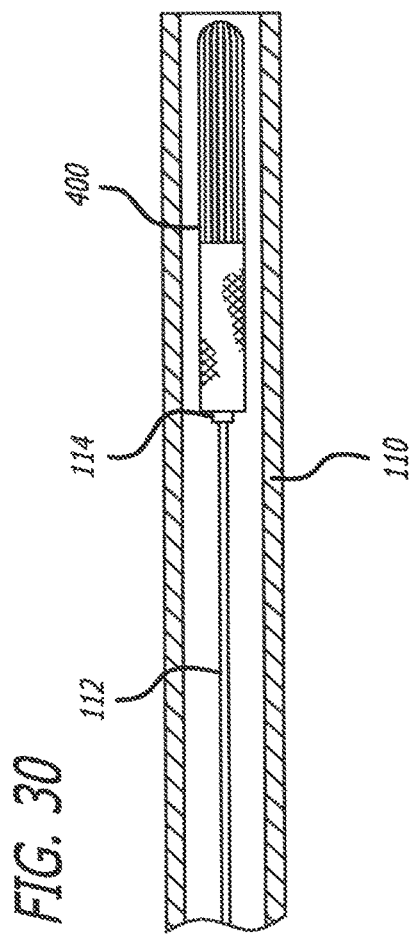
FIG. 30 shows the device of FIG. 10 disposed within a microcatheter in a collapsed radially constrained state.

The device 400 and expandable body thereof also have a low profile radially constrained state, as shown in FIG. 30, with an elongated configuration that includes a longitudinal axis. In the collapsed, radially constrained state, the elongate flexible struts 410 of the expandable body may be disposed substantially parallel to each other. The radial constraint on the device may be applied by an inside surface of the inner lumen of a microcatheter, such as the distal end portion of the microcatheter 110 shown in FIG. 30, or it may be applied by any other suitable mechanism that may be released in a controllable manner upon ejection of the device from the distal end of the catheter.

Figure 32:
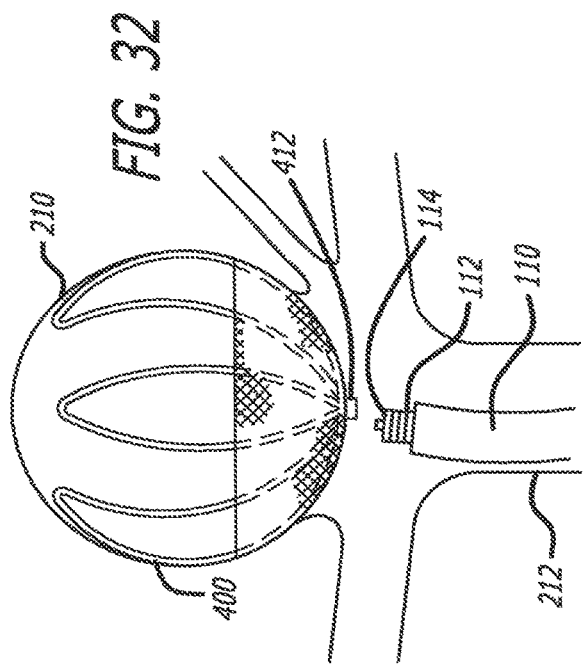
FIG. 32 is a sectional view of a terminal aneurysm with an embodiment of a device for treatment of a patient's vasculature deployed within the aneurysm.

The device 400 may be deployed within a target vascular defect such that the defect spanning portion 408 is positioned substantially covering the defect opening or neck of the aneurysm as shown in FIGS. 31 and 32. While the device 400 may have a substantially spherical, bulbous or globular shape in its natural, relaxed, undeformed or minimum energy state, the structure may be compliant to conform to various vessel anatomy; thus, the shape after implantation may have deviations from its natural shape. The structure may be formed from a plurality of strut members 410 that coalesce or are joined at one or more points. The device is collapsed into a substantially linear form for delivery through a catheter. When released from the distal end of the catheter, the device preferably self-expands due to elastic recoil to return to its lowest energy state shape. It may form a globe-like structure that has a generally oval, circular or ellipsoid cross-section. The distal portion that is deployed in the dome of the aneurysm may be open thus allowing at least a portion of the aneurysm to shrink after treatment. This may provide for the reduction of mass effect.

The engagement of the bulbous portion of the second end portion of the support structure 402 may be achieved by the exertion of an outward radial force against tissue of the inside surface of the cavity of the patient's vascular defect. A similar outward radial force may also be applied by the first end portion of the device so as to engage the defect spanning structure with the inside surface or adjacent tissue of the vascular defect. Such forces may be exerted in some embodiments wherein the nominal outer transverse dimension or diameter of the support structure in the relaxed unconstrained state is larger than the nominal inner transverse dimension of the vascular defect within which the support structure is being deployed. The elastic resiliency of the support structure 402 may be achieved by an appropriate selection of materials, such as superelastic alloys, including nickel titanium alloys, stainless steel, or any other suitable material for some embodiments.

Embodiments of the permeable layer of the defect spanning structure 408 may include a convex configuration that spans the first end 404 of the expandable body in a relaxed expanded state and extends along the struts 410 towards the second end 406. In some embodiments, the permeable layer may span the struts 410 towards the second end to a longitudinal position of about 10 percent to about 60 percent the total length of the expandable body when the expandable body is in a relaxed expanded state. Embodiments of the defect spanning structure 408 may include any of the materials discussed above including perforated membranes, laser cut polymer membranes, microfibers, including electrospun microfibers, as well as others. Embodiments of the defect spanning structure may be secured to the support structure by adhesive bonding, suturing, lacing, or any other suitable method.

For some embodiments of the device, the struts 410 of the expandable body of the support structure 402 may include perforations which are configured for securing the permeable layer to the expandable body by lacing, suturing or the like. The defect spanning structure 408 in the form of a permeable layer may be disposed interiorly or exteriorly to an outer surface or structure of the expandable body. The defect spanning structure 408 may also include multiple layers. For some such multiple layer embodiments, an outer layer of the permeable membrane, or defect spanning structure generally, disposed away from the vascular defect and towards the patient's vasculature may include an antithrombogenic agent. An inner layer disposed towards the vascular defect on an opposite side of the outer layer may include a thrombogenic agent that may be eluted therefrom. The thrombogenic agent eluted from the inner layer, and particularly, eluted into the vascular defect, may promote thrombosis, stabilization or healing of the vascular defect. For some embodiments, the inner layer and outer layer may be secured together in a monolithic structure. For some embodiments, the permeable layer may include a thin membrane having a combination of macropores and micropores. For some embodiments, the macropores may have a transverse dimension of about 100 microns to about 500 microns and the micropores have a transverse dimension of about 10 microns to about 100 microns.

For some embodiments, a total volume of the permeable layer of the defect spanning structure 408 may be less than about 5 mm3. For some embodiments, a total volume of permeable layer may be between about 0.5 mm3 and 4 mm3. For some embodiments, the permeable layer may have a porosity greater than about 60 percent and a thickness of less than about 50 microns. For some embodiments, the permeable layer may be about 2 microns to about 10 microns thick. For some embodiments, the expandable body of the support structure 402 may have a first transverse dimension in a collapsed radially constrained state of about 0.2 mm to about 2 mm and a second transverse dimension in a relaxed expanded state of about 4 mm to about 30 mm. Some embodiments of the device 400 may include a sealing member (not shown) disposed about a perimeter or other suitable portion of the permeable layer, or defect spanning structure 408 generally, and be configured to form a seal between the permeable layer and a surface of the patient's vasculature. Some embodiments of the sealing member may include a swellable polymer.

Delivery systems and methods, such as an suitable delivery system or method discussed or incorporated herein, may be used that allows for accurate positioning such that the device 400 is deployed within the vascular defect with the defect spanning structure 408 substantially covers the defect opening or neck as shown in FIGS. 31 and 32. The device 400 may be implanted substantially within a target vascular defect; however, in some embodiments, a portion of the device may extend into the defect opening or neck or into branch vessels. Axial movement and deployment of the device 400 from the microcatheter may be controlled by an actuator member 112 and release mechanism 114 that releasably secures a distal end of the actuator member to the device. The release or detachment mechanism may include any suitable embodiment of release mechanisms discussed or incorporated herein.

Figure 33:
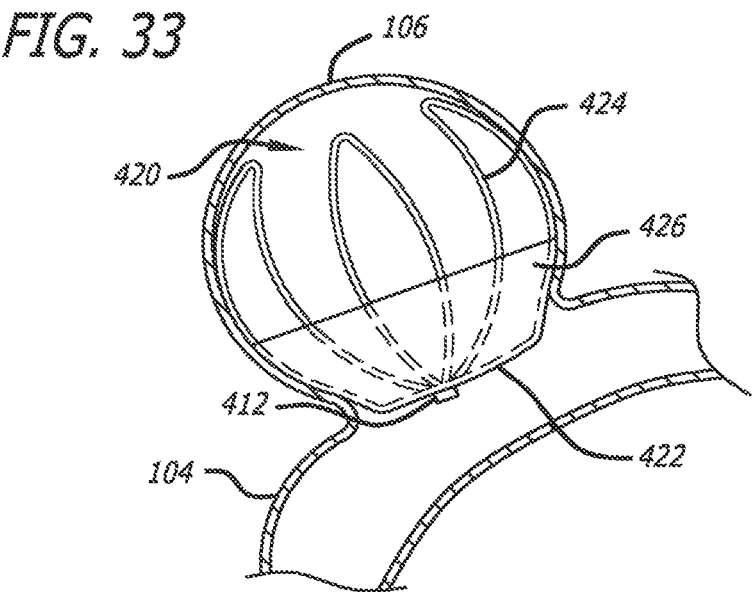
FIG. 33 is a sectional view of an aneurysm with an embodiment of a device for treatment of a patient's vasculature deployed within the aneurysm.
Figure 34:
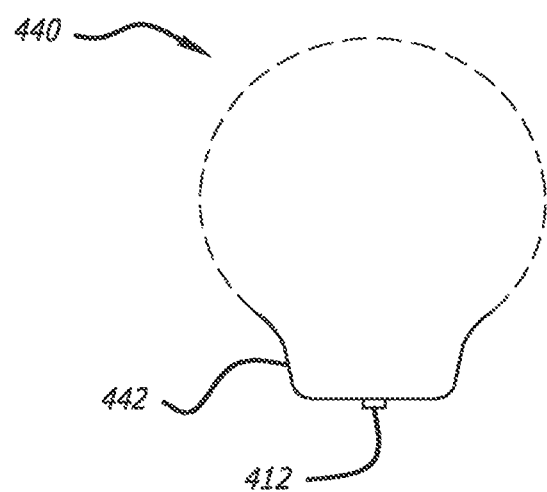
FIG. 34 is an elevation view of an outline of an embodiment of a device for treatment of a patient's vasculature having a recessed detachment hub.

FIGS. 33 and 34 illustrate an embodiment of a device 420 that may have the same or similar features, dimension and materials as those of the device of FIGS. 29-32. The device for treatment of a patient's vasculature 420 shown in FIG. 33 includes a substantially flattened first end 422 or side of the device a support structure 424 and a defect spanning structure 426. FIG. 34 illustrates an outline of an embodiment of a device for treatment of a patient's vasculature 440 that includes a trunk portion 442 extending from a first end 444 of the device. The trunk portion 442 is a somewhat cylindrical extension extending from the nominal globular or spherical shape of the device. For some of these embodiments, the detachment hub 412 may be recessed so that the profile of the device in the blood vessel lumen is reduced. The device embodiments 420 and 440 of FIGS. 33 and 34 may be delivered and deployed in the same manner and with any of the same devices and methods as those discussed above with regard to the device embodiment 400 of FIG. 29.

Figure 35:
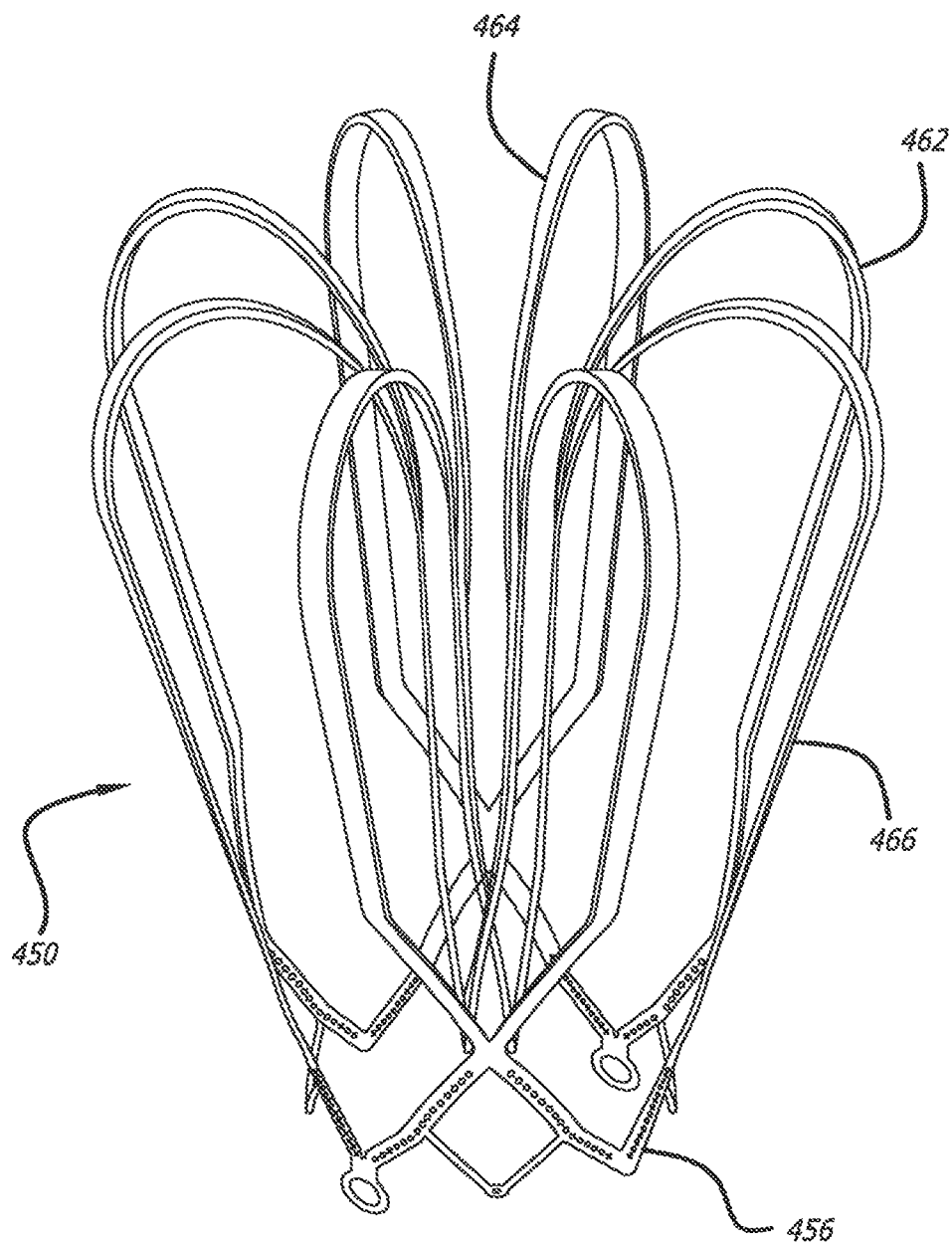
FIG. 35 is a perspective view of a heat set inverted or everted globe support structure of a device for treatment of a patient's vasculature.
Figure 36:
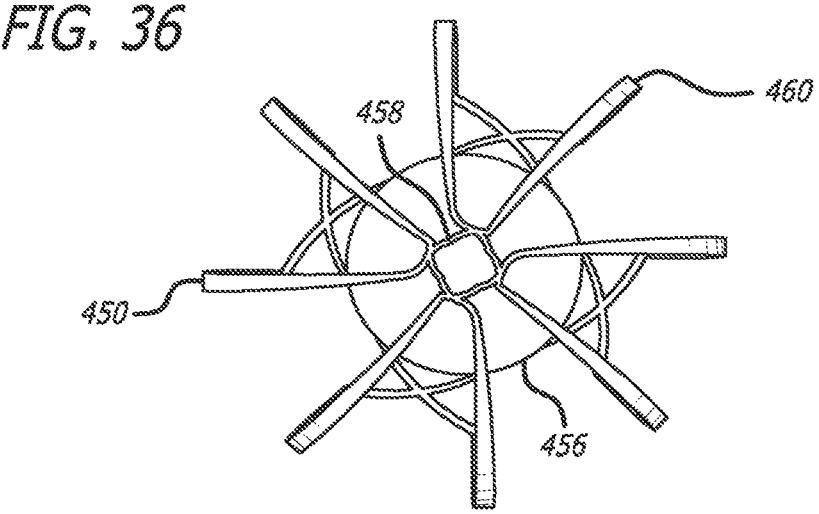
FIG. 36 is a proximal end view of the expandable body support structure of FIG. 35.
Figure 37:
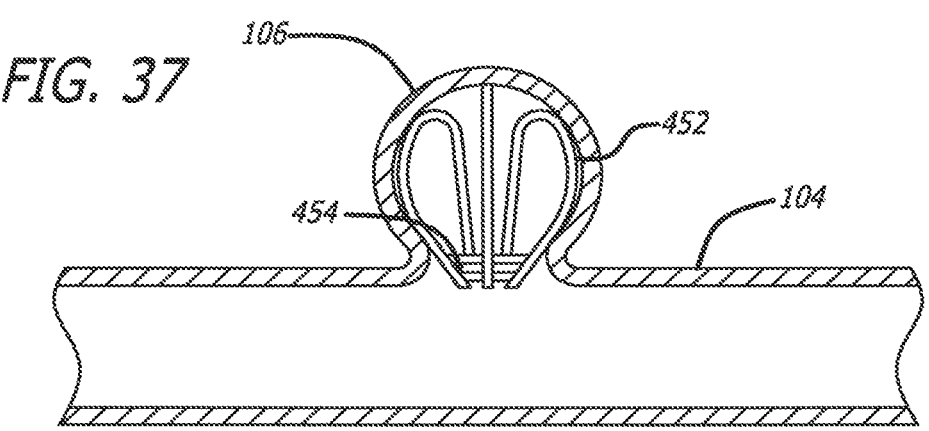
FIG. 37 shows a sectional view of an embodiment of a device for treatment of a patient's vasculature deployed in a vascular defect.

FIGS. 35 and 36 show an embodiment of a support structure 450 for an intrasaccular device embodiment for treatment of a patient's vasculature. The device 452 may be configured to readily conform to an inside cavity of a patient's vascular defect as shown in FIG. 37. The device 452 includes the expandable body support structure 450 having a low profile radially constrained state and a relaxed expanded state. The device 452 also includes a defect spanning structure 454 disposed at and conforming to a profile of a first end 456 of the expandable body 450 when the expandable body is in the expanded relaxed state. The defect spanning structure 454 may include a permeable layer.

Figure 38:
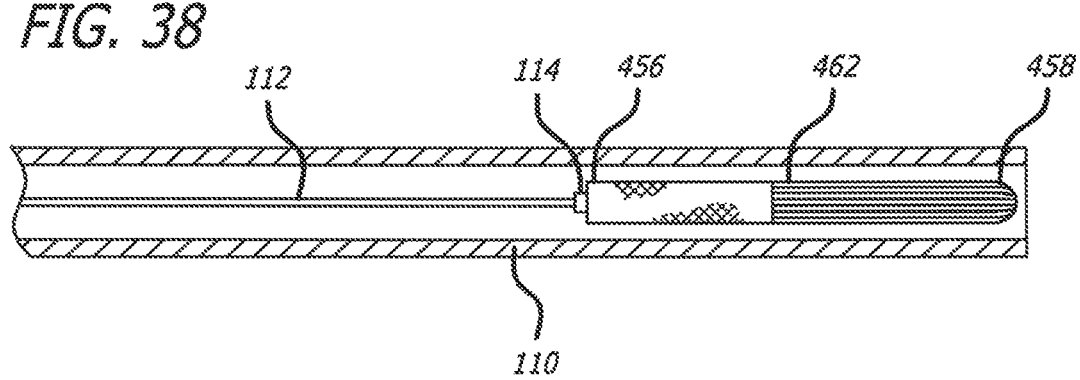
FIG. 38 shows the device of FIG. 37 disposed within a microcatheter in a collapsed radially constrained state.

In the radially constrained state, as shown in FIG. 38, the expandable body 450 has an elongated tubular configuration that includes the first end 456, a second end 458, a longitudinal axis and elongate flexible struts 460, portions of which are disposed substantially parallel to each other. The first ends of the struts 460 of the expandable body 450 are secured to each other in a first zig-zag shaped expandable section. The second ends of the struts 460 are secured relative to each other in a second zig-zag shaped expandable section. Both the first and second zig-zag shaped expandable sections are disposed substantially concentric to the longitudinal axis of the expandable body 450. A middle portion 462 of the expandable body has a first transverse dimension with a low profile suitable for delivery from a microcatheter 110.

In the expanded relaxed state, as shown in FIG. 35, the expandable body 450 has an axially shortened configuration relative to the constrained state with second ends and the second zig-zag shaped expandable section everted within a radially expanded middle portion 462 and disposed adjacent the first zig-zag shaped expandable section adjacent the first end 456. The second zig-zag shaped expandable section is also disposed substantially concentric to the longitudinal axis of the expandable body with each strut 460 forming a smooth arc between the first and second ends 456 and 458 such that the arc of each strut extends axially outward beyond the first transverse dimension. Further, the middle portion 462 has a second transverse dimension substantially greater than the first transverse dimension. In this expanded state, each strut is configured to independently flex radially with respect to the longitudinal axis of the expandable body so as to readily conform to a shape of an interior portion of a patient's vascular defect as shown in FIG. 37. When in an expanded everted state, the support structure 450 has a distal or second end 464 formed substantially at a distal apex of each strut 460 when the struts 460 are in a curved arc. The struts 460 may also have a tapered outer contour 466 when in this configuration.

Delivery systems and methods, such as an suitable delivery system or method discussed or incorporated herein, may be used that allows for accurate positioning and deployment of the device 452 such that the device is deployed within the vascular defect 106 with the defect spanning structure 454 substantially covering the defect opening or neck as shown in FIG. 37. The device 452 may be implanted substantially within the vascular defect; however, in some embodiments, a portion of the device may extend into the defect opening or neck or into branch vessels. Axial movement and deployment of the device 452 from the microcatheter 110 may be controlled by an actuator member 112 and release mechanism 114 that releasably secures a distal end of the actuator member 114 to the device 452. The release or detachment mechanism 114 may include any suitable embodiment of release mechanisms discussed or incorporated herein. While disposed within the microcatheter 110 or other suitable delivery system, as shown in FIG. 38, the struts 460 may take on an elongated, non-everted configuration substantially parallel to each other and a longitudinal axis of the catheter. Once the device 452 is ejected from the distal end of the catheter 110 or the radial constraint is otherwise removed, the second ends of the struts 460 may then curve back on themselves so as to assume the globular everted configuration within the vascular defect as shown in FIG. 37.

In a deployed expanded state, the device 452 may be configured to have an opening at the top or distal end 464 of the deployed device which may allow for the treated aneurysm to shrink and thus reduce mass effect on surrounding tissues as shown in FIG. 37. For these embodiments, the support structure sides 466 formed by the struts may be substantially flat or have convex surface. The distal end 464 of the device 452 may be heat treated to a shape or configuration that is substantially closed with the inverted or everted struts making or nearly making contact. In addition, the distal end 464 may have an opening to allow for some aneurysm shrinkage into the cavity formed by the device during the healing process. The proximal end 456 may be straight with a circular end, as shown in FIG. 36, or flare inward or outward to form a star-shaped proximal end opening (not shown).

In some embodiments, at least a portion of some struts 460 of the support structure 450 may include a plurality of holes for attachment of the defect spanning structure 454. In some embodiments, there may be two rows of holes in a proximal portion of some struts 460 as shown in FIG. 8 discussed above. The holes may be made such that they define a lumen that is perpendicular to the strut and the support structure 450. Thus the axis of each hole may be disposed radially to the support structure. For some embodiments, the holes may be tangential to the struts 460 of the support structure. For some embodiments, the defect spanning structure 454 may be formed by a plurality of microfibers that are threaded through the holes of one or more support structure struts as shown in FIG. 9 discussed above. The microfibers may span from strut to strut in a substantially straight line or have a curved shape. The fibers may be configured so as to substantially align with the surface or shape defined by the support structure 450. The microfibers may be attached to the structure by knots, adhesives or a small anchor element that is attached to an end of a microfiber as shown in FIG. 10. For some embodiments, the fibers may have lengths configured to span a gap between struts and be held taught under tension when the support structure is in a relaxed deployed state.

Some of the microfibers may be substantially parallel to each other in the span between two or more struts 460. The gaps or slots formed by the openings between two adjacent fibers or microfibers may be less than about 0.125 mm, for some embodiments. With the microfibers being arranged in a substantially parallel fashion as opposed to a mesh, such as a braid or the like, a guidewire or microcatheter may be more easily passed through the openings as shown in FIG. 11 discussed above. This may allow for subsequent treatment of the vascular defect. For example, subsequent treatments of the vascular defect may include the delivery of an embolic material, devices to fill at least a portion of the space behind the defect spanning structure 454, both of these or any other suitable treatment. Further, mesh structures typically involve overlapping of fibers that result in a thicker, more voluminous membrane, making the parallel disposition of the fibers more amendable to compaction than mesh which may be useful for achieving a low profile necessary for delivery through a microcatheter.

In some embodiments, the defect spanning structure 454 of the device 452 may include multiple layers. For some embodiments of the device, the first or outer layer of the defect spanning structure may be attached or secured to the proximal or first end portion of the support structure. Subsequent or inner layer(s) may be attached distal to the proximal end of the support structure struts 460. Such a configuration is shown in FIG. 13 with some lower strut portions not shown for clarity of illustration. In some embodiments, the fabric layer or layers may be fabricated directly on to the support structure, fusing to each other, the support structure or both of these as they are formed. As discussed above, the various layers may include bioactive agents so as to improve the performance of some embodiments.

Embodiments of the support structure 450 may further include fixation elements, sealing members or both. Some fixation element embodiments may be configured to extend from one or more of the support structure struts 460 at or near the proximal end 456 of the device to facilitate fixation of the device within the vascular defect. Sealing member embodiments may extend radially from the axis of the support structure or be otherwise configured to engage a neck of the vascular defect as shown in FIG. 14 and form a seal or reduce leakage between the defect spanning structure and tissue of the vascular defect.

Figure 40:
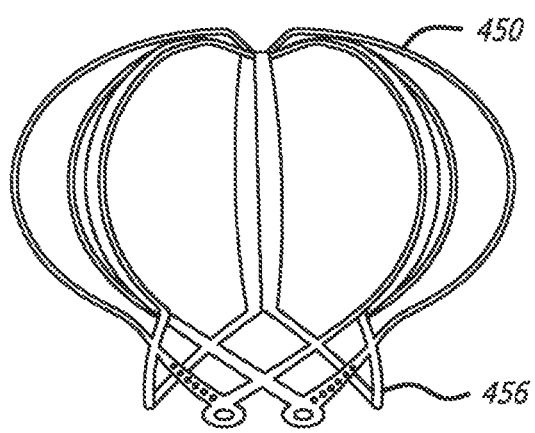
FIG. 40 is an elevation view of the laser cut tube of FIG. 39 in a partially expanded state for heat setting.
Figure 41:
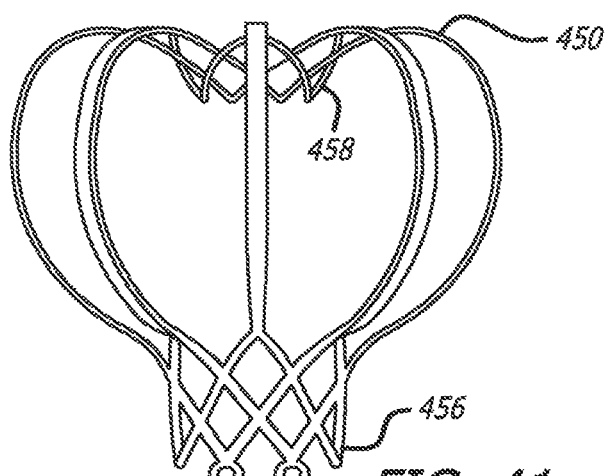
FIG. 41 is an elevation view of the laser cut tube of FIG. 39 with a distal end of the tube inverted or everted into the expanded globe structure of the laser cut tube for heat setting.
Figure 42:
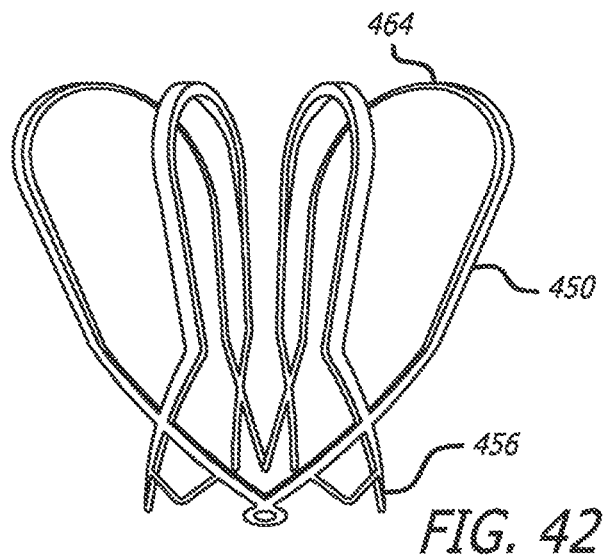
FIG. 42 is an elevation view of the laser cut tube of FIG. 39 with the distal end of the tube further inverted or everted into the globe structure of the laser cut tube for heat setting with the distal end of the tube adjacent the proximal end of the laser cut tube.

Embodiments of the support structure 450 of the device for treatment of a patient's vasculature may be fabricated from a tube of metal where portions of the tubular structure are selectively are removed. The removal of material may be done by laser, electrical discharge machining (EDM), photochemical etching and traditional machining techniques as well as any other suitable modality. In some embodiments, the support structure 450 may have an initial manufactured configuration that is substantially tubular, such as the laser cut tube shown in FIG. 39. The support structure may then held in a desired form or configuration for the final implant and then heat treated to set the shape of the support structure 450. The structure of the expandable body may also be shaped in multiple shaping and heat treatment steps, including evertion of the distal end 458 into the body structure of the support structure 450, as shown in the sequential steps in FIG. 40 through FIG. 42. The distal end or second end 458 may be inverted into the inside of the overall shape to form a final tapered globular shape. For some embodiments, the distal or second end 458 is brought down to nearly the inside of the proximal or first end 456 as shown in FIG. 42. By inverting the distal end, the curved struts that form the distal end 464 of the device 452 are easily flexed radially providing conformance to irregular vascular defect spaces.

Embodiments of methods for fabricating vascular defect treatment device embodiments discussed herein may include a variety of procedures. For some embodiments, as discussed above, a plurality of strut members may be formed into a substantially tubular configuration with a distal end and a proximal end where the strut members are connected at both the distal and proximal ends. The strut array may then be shaped to form a globular support structure. A porous membrane, mesh or microfiber matrix may be formed that is less than about 50 microns thick for some embodiments and secured or attached to at least a portion of the support structure to form a defect spanning structure. For some embodiments, a tube structure may be cut to form a plurality of struts that are substantially parallel and thus define a substantially cylindrical array. For some embodiments, a globular support structure may be formed from the struts or strut array wherein one end of the tubular structure is everted so as to be disposed inside a structure envelope of the strut elements. This configuration may also be heat set for some embodiments.

Some method embodiments may include attaching the defect spanning structure membrane, mesh or microfiber matrix to a portion of an inner surface of at least some of the support structure struts. Some embodiments may include forming a thin membrane, mesh or microfiber matrix on a three dimensional mandrel to form a three dimensional defect spanning structure. Some embodiments include perforating the thin membrane, mesh or microfiber matrix to form a plurality of macropores between about 100 microns and 500 microns in transverse dimension or diameter. Some embodiments include casting a microfiber matrix onto a porous collector to form a defect spanning structure with both micropores and macropores which may optionally include flowing gas or creating a vacuum such that gas flows through the porous collector during the casting process. Some embodiments include forming a porous defect spanning structure that has a water permeability of more than about 2,000 ml/min/cm2 with a pressure head of 120 mmHg.

Figure 43:
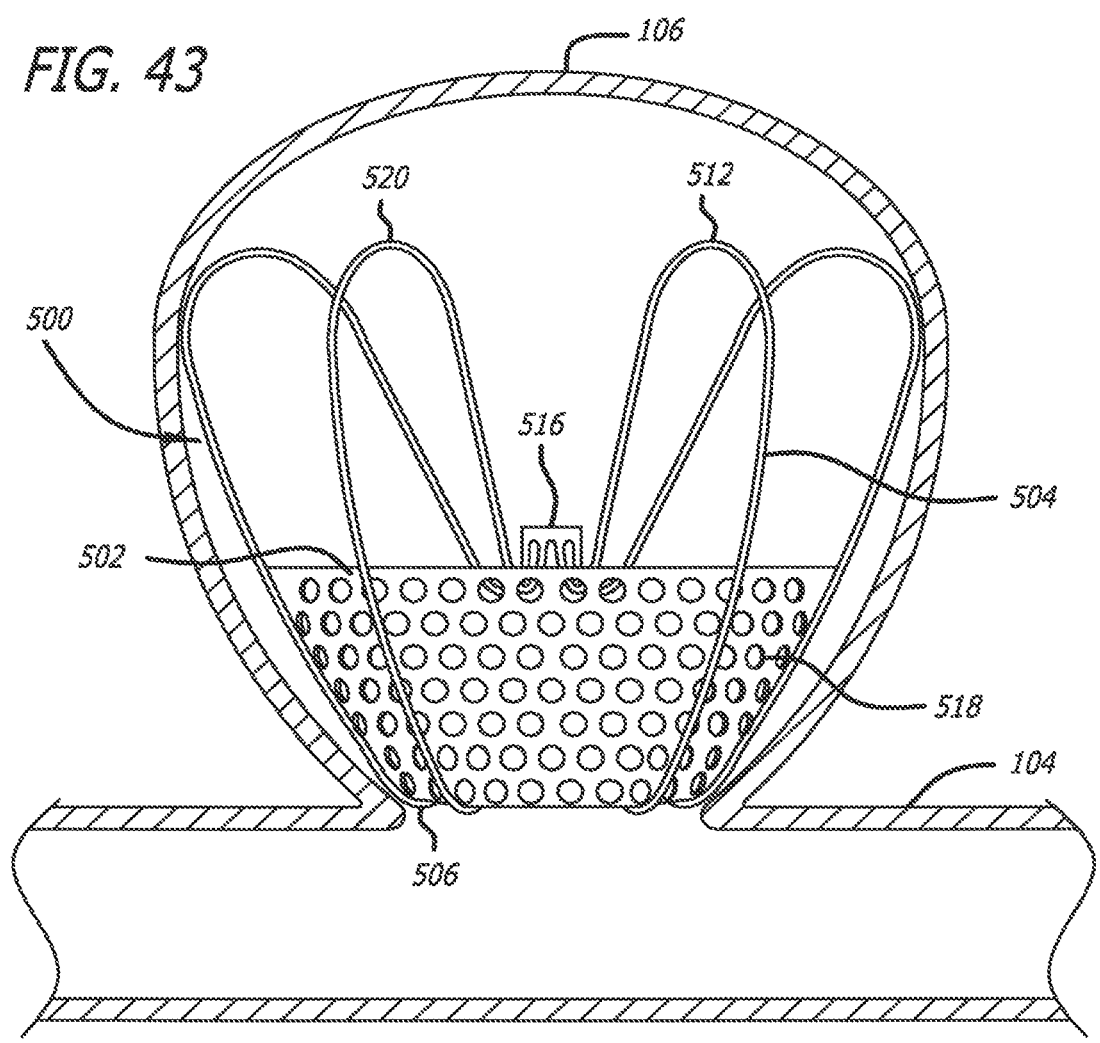
FIG. 43 is an elevation view of an embodiment of a device for treatment of a patient's vasculature in a relaxed expanded state disposed in a vascular defect of a patient.
Figure 44:
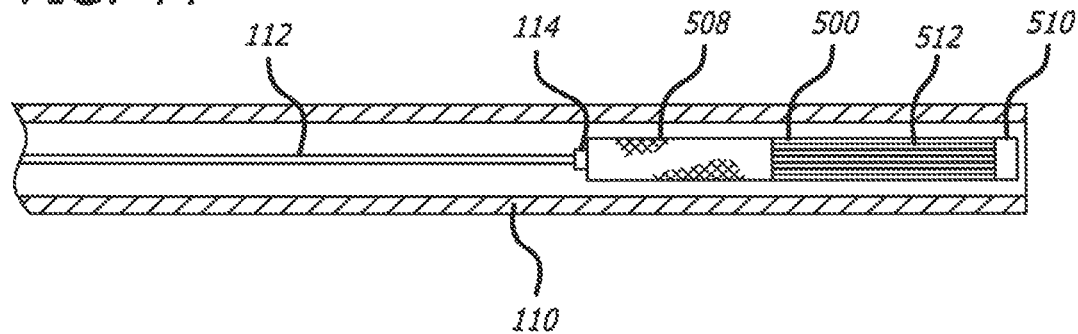
FIG. 44 shows the device of FIG. 43 disposed within an inner lumen of a microcatheter embodiment in a collapsed radially constrained state.

Referring to FIGS. 43 and 44, an embodiment of an intrasaccular device for treatment of a patient's vasculature 500 is shown that has an everted structure at a first end and second end when in an expanded relaxed state. The device 500, and particularly the defect spanning portion 502 of the device, may have some of the same or similar features, dimensions and materials as those of the device 452 of FIG. 37. The device 500 includes a support structure 504 having a substantially closed shape with a defect spanning structure 502 disposed at a first end 506 of the device when in an expanded state. The defect spanning structure may be configured to substantially block flow into the defect 106 or otherwise isolate the vascular defect 106 when the device 500 is deployed in an expanded state. The support structure 504 also has a low profile radially constrained state, as shown in FIG. 44, with an elongated tubular configuration that includes a first end 508, a second end 510, a longitudinal axis and elongate flexible struts 512 disposed substantially parallel to each other between the first end and second end.

Figure 51:
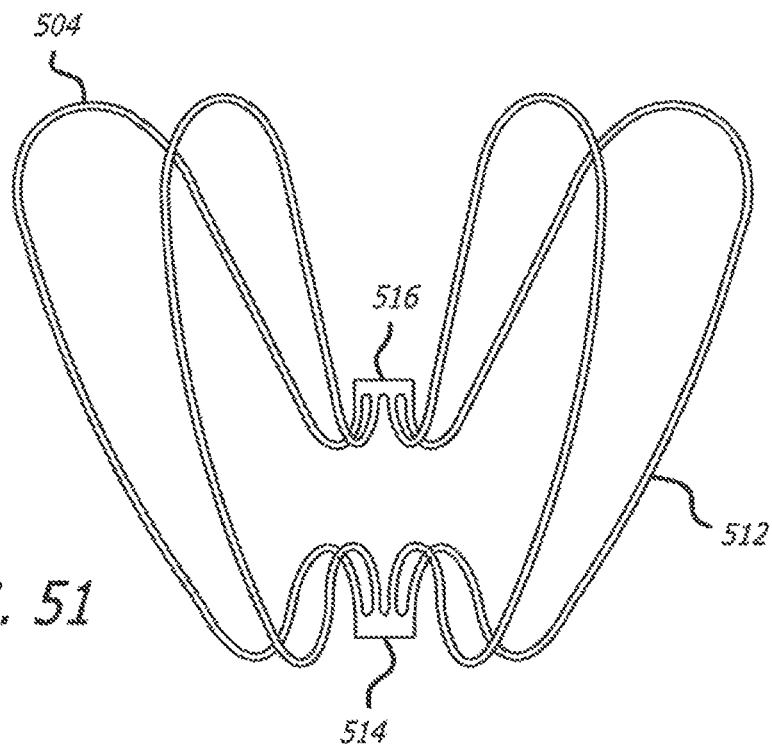
FIG. 51 is an elevation view of the laser cut tube of FIG. 49 which is heat set with first and second ends of the tube axially collapsed towards each other into an everted globe like structure.

The first ends of the expandable body 504 are secured to a first ring or hub 514 and second ends of the expandable body are secured to a second ring or hub 516, with the first and second rings being disposed substantially concentric to the longitudinal axis as shown in FIG. 51. A middle portion of the expandable body 504 may have a first transverse dimension with a low profile suitable for delivery from a microcatheter. For some embodiments, the first and second rings 514 and 516 of the expandable member 504 may be open rings having an open lumen disposed within each of the first and second rings. For some embodiments, the inner lumen of the first ring 514, second ring 516 or both may be sealed or closed. Radial constraint on the device 500 may be applied by an inside surface of the inner lumen of a microcatheter, such as the distal end portion of the microcatheter 110 shown in FIG. 44, or it may be applied by any other suitable mechanism that may be released in a controllable manner upon ejection of the device from the distal end of the catheter.

The expanded relaxed state of the expandable body 504 has an axially shortened configuration relative to the constrained state with the first ring 514 disposed adjacent the second ring 516, both rings substantially concentric to the longitudinal axis and each strut 512 forming a smooth arc between the first and second rings 514 and 516 with a reverse bend at each end. A longitudinal spacing between the first ring and second ring 514 and 516 of the expandable body 504 in a deployed relaxed state may be about 10 percent to about 50 percent of the longitudinal spacing between the first ring and second ring in the constrained tubular state, for some embodiments. The arc of the struts 512 between the first and second ends are configured such that the arc of each strut extends axially beyond each respective ring 514 and 516 and such that the middle portion of each strut 512 has a second transverse dimension substantially greater than the first transverse dimension. Further, each strut 512 may be configured to independently flex radially with respect to the longitudinal axis of the expandable body. The device 500 also includes a permeable layer portion of the defect spanning structure 502 which is disposed at the first end 506 and conforms to a profile of a first end 506 of the expandable body 504 when the expandable body is in the expanded relaxed state. The permeable layer of the defect spanning structure 502 may include a plurality of holes 518 that are configured to produce a desired amount of permeability.

The engagement of the bulbous portion of the second end portion 520 of the support structure 504, when the support structure is in an expanded relaxed state, may be achieved by the exertion of an outward radial force against tissue of the inside surface of the cavity of the patient's vascular defect 106. A similar outward radial force may also be applied by the first end portion of the device so as to engage the defect spanning structure 502 with the inside surface or adjacent tissue of the vascular defect 106. Such forces may be exerted in some embodiments wherein the nominal outer transverse dimension or diameter of the support structure 504 in the relaxed unconstrained state is larger than the nominal inner transverse dimension of the vascular defect 106 within which the support structure is being deployed. The elastic resiliency of the support structure 504 may be achieved by an appropriate selection of materials, such as superelastic alloys, including nickel titanium alloys, stainless steel, or any other suitable material for some embodiments. For some embodiments, the expandable body 504 may include a heat set shape memory material that may be heat set in the relaxed expanded state. The expandable body may also include a superelastic material or shape memory material such as a shape memory alloy such as nickel titanium. Such embodiments as well as any other embodiments of the expandable body 504 may include self-expanding embodiments.

For some embodiments, the defect spanning structure 502 may include a permeable layer of a thin membranous film or mesh which may be cast or otherwise formed onto a mandrel with a desired three dimensional shape. The three dimensionally shaped defect spanning structure may be attached to the support structure 504 forming an umbrella-like portion as shown at the first end 506 of the device 500 in FIG. 43. The defect spanning structure 502 may be secured to the interior, exterior or substantially aligned with the struts 512 of the support structure 504. In some embodiments, the defect spanning structure 502 may be disposed inside the support structure 504 so that it is inside the support structure 504 when collapsed and thus protected from abrasion and tearing during delivery and deployment of the device 500.

Embodiments of the permeable layer of the defect spanning structure 502 may include a convex configuration that spans the first end 506 of the expandable body 504 when the expandable body is in a relaxed expanded state and extends along the struts towards the second end 520. In some embodiments, the permeable layer may span the struts 512 towards the second end 520 to a longitudinal position of about 10 percent to about 60 percent the total length of the expandable body 504 when the expandable body is in a relaxed expanded state. Embodiments of the defect spanning structure 502 may include any of the materials discussed above including perforated membranes, laser cut polymer membranes, microfibers, including electrospun microfibers, as well as others. Embodiments of the defect spanning structure may be secured to the support structure 504 by adhesive bonding, suturing, lacing, or any other suitable method.

For some embodiments of the device 500, the struts 512 of the expandable body of the support structure 504 may include perforations which are configured for securing the permeable layer to the expandable body by lacing, suturing or the like. The defect spanning structure 502 in the form of a permeable layer may be disposed interiorly or exteriorly to an outer surface or structure of the expandable body. The defect spanning structure may also include multiple layers. For some such multiple layer embodiments, an outer layer of the permeable membrane, or defect spanning structure generally, disposed away from the vascular defect and toward the patient's vasculature may include an anti-thrombogenic agent. An inner layer disposed towards the vascular defect 106 on an opposite side of the outer layer may include a thrombogenic agent that may be eluted therefrom. The thrombogenic agent eluted from the inner layer, and particularly, eluted into the vascular defect, may promote thrombosis, stabilization or healing of the vascular defect. For some embodiments, the inner layer and outer layer may be secured together in a monolithic structure. For some embodiments, the permeable layer may include a thin membrane having a combination of macropores and micropores. For some embodiments, the macropores may have a transverse dimension of about 100 microns to about 500 microns and the micropores have a transverse dimension of about 10 microns to about 100 microns.

For some embodiments, a total volume of the permeable layer of the defect spanning structure 502 may be less than about 5 mm3. For some embodiments, a total volume of permeable layer may be between about 0.5 mm3 and 4 mm3. For some embodiments, the permeable layer may have a porosity greater than about 60 percent and a thickness of less than about 50 microns. For some embodiments, the permeable layer may be about 2 microns to about 10 microns thick. For some embodiments, the expandable body of the support structure 504 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the expandable body may be about 2 times to about 150 times the first transverse dimension, more specifically, about 10 times to about 20 times the first transverse dimension. Some embodiments of the device 500 may include a sealing member (not shown) disposed about a perimeter or other suitable portion of the permeable layer, or defect spanning structure 502 generally, and be configured to form a seal between the permeable layer and a surface of the patient's vasculature. Some embodiments of the sealing member may include a swellable polymer.

For some embodiments, strut elements 512 of the expandable body may have a major transverse dimension of about 0.005 inches to about 0.015 inches, a minor transverse dimension of about 0.001 inches to about 0.006 inches and a transverse cross section that is substantially rectangular or elliptical in shape. Strut embodiments may also have a transverse cross section includes a major transverse dimension disposed circumferentially with respect to the longitudinal axis of the expandable body and a minor transverse dimension disposed radially with respect to the longitudinal axis of the occlusive body. For some embodiments, the strut members 512 may be substantially round or square in transverse cross section with the same or similar transverse dimensions as those above.

Delivery systems and methods, such as any suitable delivery system or method discussed or incorporated herein, may be used that allows for accurate positioning and deployment of the device 500 such that the device is deployed within the vascular defect with the defect spanning structure 502 substantially covering the defect opening or neck as shown in FIG. 43. The device 500 may be implanted substantially within the vascular defect 106, however, in some embodiments, a portion of the device may extend into the defect opening or neck or into branch vessels. Axial movement and deployment of the device 500 from the microcatheter 110 may be controlled by an actuator member 112 and release mechanism 114 that releasably secures a distal end of the actuator member 112 to the device 500. The release or detachment mechanism 114 may include any suitable embodiment of release mechanisms discussed or incorporated herein. For some embodiments, a detachment mechanism 114, or portion thereof, may be secured within the lumen of the first ring 514 and seal or close the lumen of the first ring. While disposed within the microcatheter or other suitable delivery system, as shown in FIG. 44, the struts 512 may take on an elongated, non-everted configuration substantially parallel to each other and a longitudinal axis of the catheter. Once the device is ejected from the distal end of the catheter or the radial constraint is otherwise removed, the second ends of the struts may then axially contract towards each other so as to assume the globular everted configuration within the vascular defect as shown in FIG. 43.

In use, the device shown in FIG. 43, or any other suitable device embodiment discussed herein, may be deployed by advancing a delivery system, such as the delivery system discussed above, or any other suitable delivery system discussed or incorporated herein, to an appropriate position adjacent a vascular defect to be treated. The device 500 may then be positioned within the vascular defect such as the aneurysm 106 shown in FIG. 43, and deployed such that the expandable body 504 self-expands within the vascular defect 106 and the defect spanning structure 502 covers at least a portion of the defect opening or neck. For some embodiments, the defect spanning structure will be positioned to cover the entire opening or neck of the defect. For some embodiments, the device is positioned within the vascular defect from a proximal end of the delivery system. The device 500 may be released or detached from the delivery system by any suitable detachment mechanism or mechanisms including thermal, mechanical, electrolytic, shape memory as well as any other suitable mechanism or mechanisms.

During deployment, the device 500 may be rotated in order to achieve a desired position of the device and, more specifically, a desired position of the defect spanning structure 502 or portions of the support structure 504, prior to or during deployment of the device. For some embodiments, the device 500 may be rotated about a longitudinal axis of the delivery system with or without the transmission or manifestation of torque being exhibited along a middle portion of a delivery catheter being used for the delivery. Suitable catheters for such use have been described and incorporated herein. These delivery and deployment methods may be used for deployment within berry aneurysms, terminal aneurysms, or any other suitable vascular defect embodiments. Some method embodiments include deploying the device at a confluence of three vessels of the patient's vasculature that form a bifurcation such that the defect spanning structure substantially covers the neck of a terminal aneurysm.

For some embodiments, once the device 500 has been deployed, the attachment of platelets to the defect spanning structure 502 may be inhibited and the formation of clot within an interior space of the vascular defect 106, device, or both promoted or otherwise facilitated with a suitable choice of thrombogenic coatings, anti-thrombogenic coatings or any other suitable coatings. Such a coating or coatings may be applied either to the defect spanning structure 502 or support structure 504 adjacent thereto. Energy forms may also be applied through the delivery apparatus and/or a separate catheter to facilitate fixation and/or healing of the device adjacent the vascular defect for some embodiments. One or more embolic devices or embolic material may also optionally be delivered into the vascular defect 106 adjacent the defect spanning structure 502 after the device 500 has been deployed. For some embodiments, a stent or stent-like support device may be implanted or deployed in a parent vessel adjacent the defect such that it spans across the vascular defect prior to or after deployment of the vascular defect treatment device.

Figure 45:
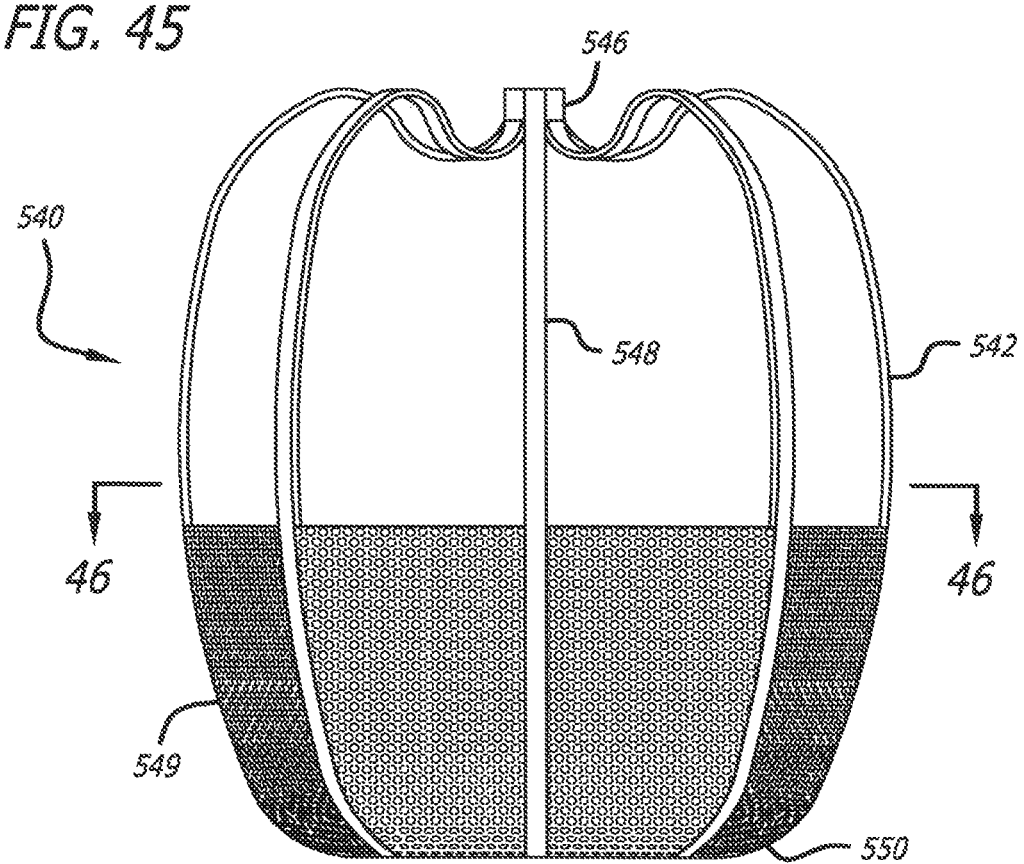
FIG. 45 is an elevation view of an embodiment of a device for treatment of a patient's vasculature.
Figure 46:
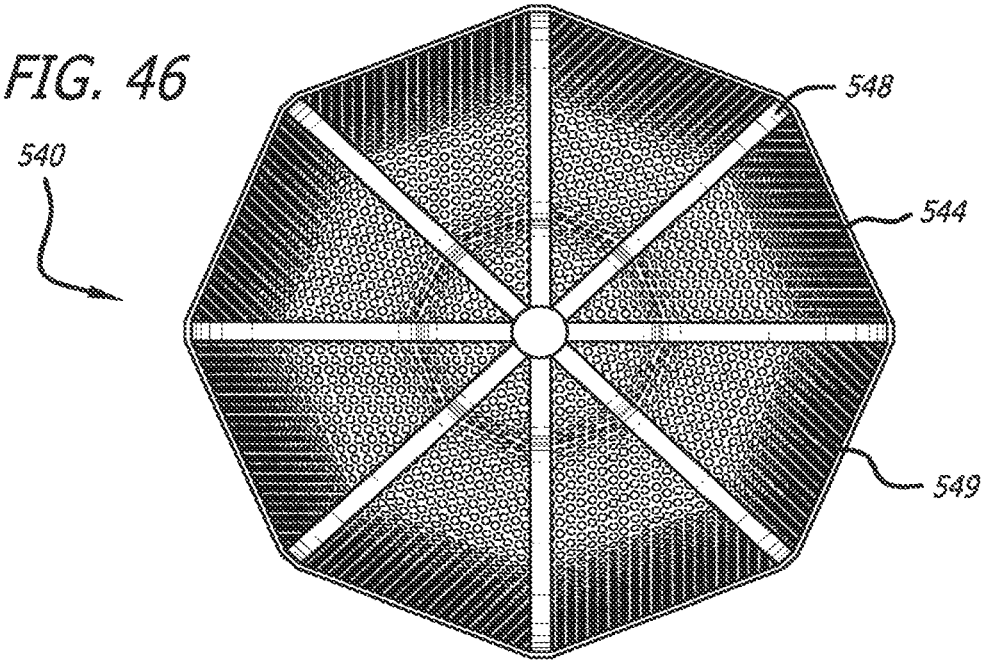
FIG. 46 is a sectional view of the device of FIG. 45 taken along lines 46-46 of FIG. 45.
Figure 47:
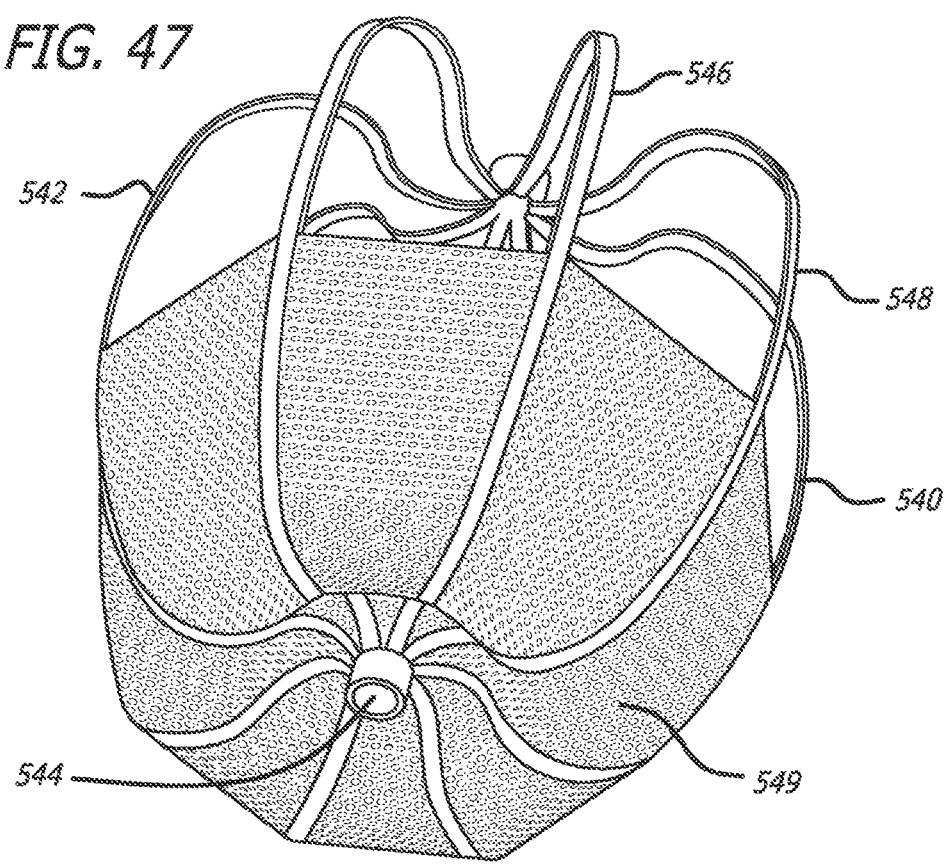
FIG. 47 shows a bottom perspective view of the device for treatment of a patient's vasculature of FIG. 45.

FIGS. 45-47 illustrate an embodiment of a device for treatment of a patient's vasculature 540 that may have similar features, dimensions and materials to those of the device for treatment of a patient's vasculature illustrated in FIGS. 43 and 44. The device in FIG. 45 includes a support structure 542 with an expandable body having an expanded relaxed state with everted or inverted ends. The support structure 542 includes a plurality of struts disposed between a first hub 544 and a second hub 546. The device 540 is shown having 8 struts disposed between the hubs 544 and 546, however, the embodiment 540, as well as embodiment 500 of FIG. 43 or any other suitable embodiment discussed herein, may have any suitable number of struts. For example, some embodiments may have about 4 struts to about 20 struts or more. Some embodiments may have about 6 struts to about 12 struts. The strut embodiments of device 540 have a transverse cross section includes a major transverse dimension disposed circumferentially with respect to a longitudinal axis of the support structure 542 and a minor transverse dimension disposed or oriented radially with respect to the longitudinal axis of the occlusive body. Embodiments of the expandable body may be formed from a slotted tubular member, as discussed above, with the first end or hub 544 and second ring or hub 546 at the ends of the tubular member shape formed or otherwise heat set in an expanded configuration wherein the first and second ends 544 and 546 are less everted than the hubs 514 and 516 of the embodiment of FIG. 43. For the device 540, some embodiments have the ends 544 and 546 of the support structure 542 disposed even with or just within a plane formed by the apices of the strut elements 548 disposed adjacent to the ends as shown in FIG. 45. The device 540 includes a defect spanning structure 549 disposed on a first end 550 of the device 540.

Devices such as the devices of FIGS. 43 and 45, as well as any other suitable embodiments discussed herein, may be made using a variety of methods. For some manufacturing embodiments, a support structure of a device may be formed by a plurality of elongate filamentary struts that are positioned into a substantially cylindrical circular array defining a lumen with the ends connected at one or more ends of the cylindrical array. At least a portion of the support structure may be radially expanded and heat treated to make a shape set of a radially expanded form or state. A thin membranous material formed of a biocompatible material may used for a defect spanning structure in conjunction with the support structure. For some embodiments, the defect spanning structure may be formed in a flat pattern to allow its folded shape to substantially conform to at least a portion of the support structure. The defect spanning structure may also be formed in a three dimensional configuration that substantially matches at least a portion of a three dimensional contour of the support structure.

Figure 48:
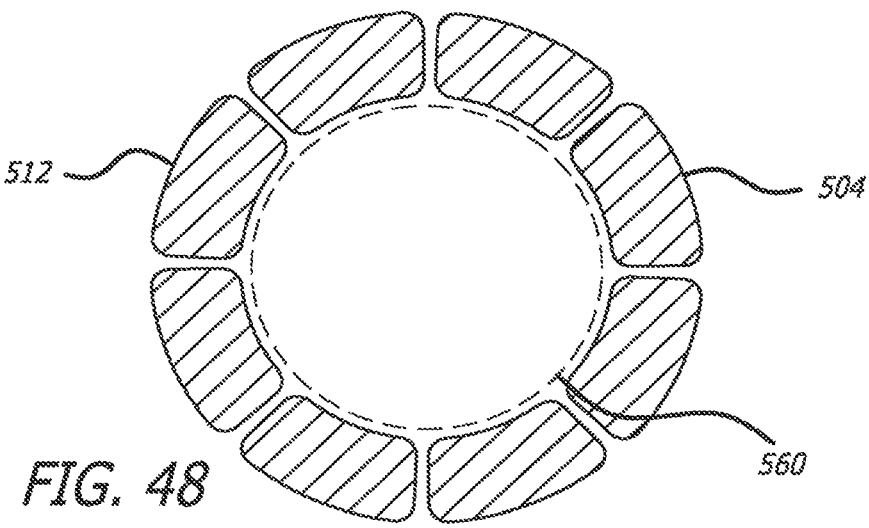
FIG. 48 is a transverse cross sectional view of a circular array of strut elements in a collapsed restrained state.

For some embodiments, pores, voids, holes, or other surface features may be made in at least a portion of the surface of the membrane of the defect spanning structure. Such features may be formed by laser cutting or any other suitable method and may have a substantially uniform array of pores. The defect spanning structure may be secured to support structure so as to span or cover at least a portion of one end of the support structure. For some embodiments, the defect spanning structure may be secured to the support structure, at least in part, by using a silane primer and an adhesive. For some embodiments, the defect spanning structure may be secured to an inner surface of the support structure 504 so that when the device is collapsed, the defect spanning structure is housed or enclosed substantially within a lumen 560 formed by struts 512 of the support structure 504, as shown in FIG. 48. Once the device has been made, the device may be removably secured to an elongate actuator 112 or the like of a delivery system designed for delivery of the device through a catheter lumen.

As discussed above, in some embodiments, the device for treatment of a patient's vasculature may include a support structure that is formed by connecting a plurality of wires or other elongate structures such as strut members in a substantially parallel orientation. The strut members may be connected at both the distal and proximal ends to form a substantially cylindrical structure. For some embodiments, the cylindrical structure may have a length that may be about 25 times greater in length than diameter. In some embodiments, a similar support structure may be formed by a tube 562 with longitudinal slots or cuts 564 as shown in FIG. 49 thus forming an array of strut members in a substantially cylindrical structure. The cuts or slots 564 in the tube 562 may be made by laser cutting or conventional machining techniques known in the art of stent fabrication. A cut tube support structure may be advantageous as it is one-piece integral structure that may not require any further welding or other joining techniques. For some embodiments, such a preform tube may have a length of about 5 mm to about 50 mm, an outer diameter of about 0.4 mm to about 1 mm and a wall thickness of about 0.025 mm to about 0.1 mm. Such a tube 562 may also include holes 566 disposed through strut portions of the tube as well as loops or other connection elements 568 disposed at a first end 570 of the tube.

Figure 50:
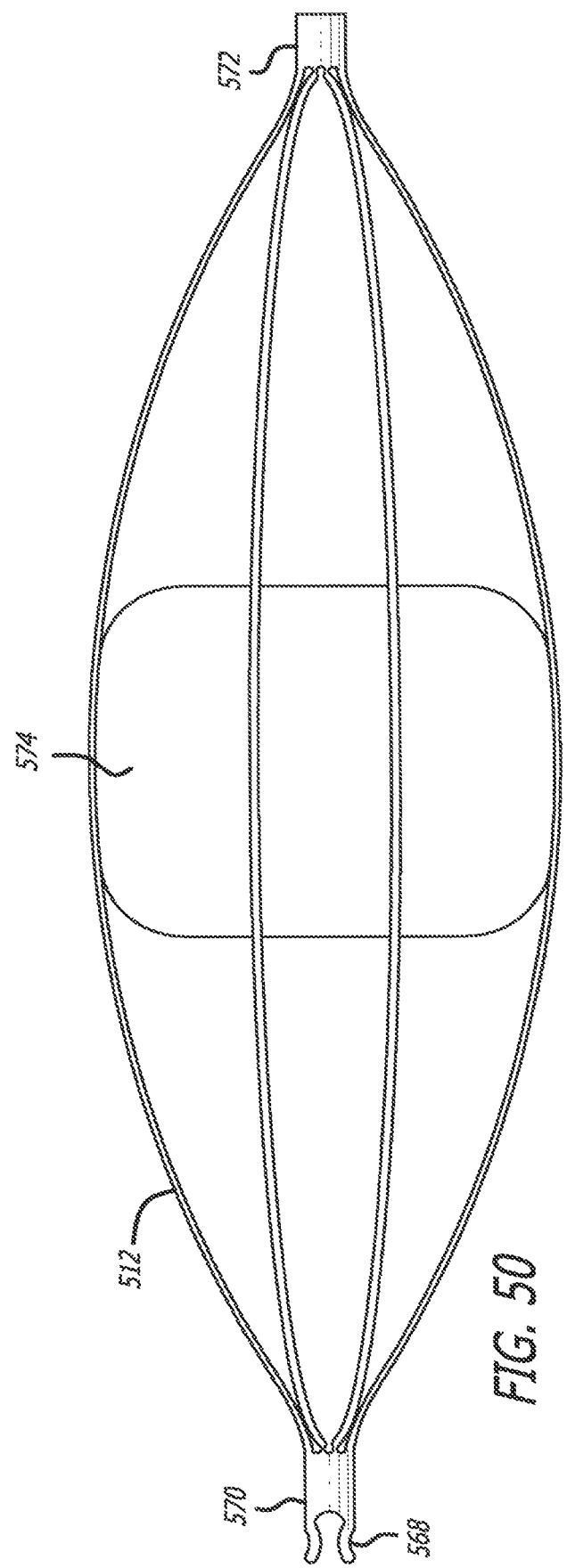
FIG. 50 is an elevation view of elongate strut elements of the laser cut tube of FIG. 49 disposed over a shaping mandrel.

Once the longitudinal slots 564 are formed into the tube, the elongate struts 512 formed between the longitudinal slots 564 may be shaped and heat set or otherwise set in order to produce a desired configuration for the support structure in a relaxed deployed state. For the embodiment shown in FIG. 49, the longitudinal slots 564 are formed in the tube which in turn forms the elongate parallel strut members 512 between the slots 564. The slots 564 may also be formed such that they terminate short of the respective ends of the tube with the first or proximal end 570, second or distal end 572 or both left in a substantially solid tubular or cylindrical configuration with fixed inner and outer diameters or transverse dimensions. Next, the strut members 512 may be elastically spread apart and a shaping mandrel 574 placed within an inner lumen disposed between the strut members with the strut members 512 expanded around an outer surface of the shaping mandrel 574 as shown in FIG. 50. The shaping mandrel 574 may be configured to produce a globular configuration with fixed diameter rings at the first end 570 and second end 572 and with one or both of the ends in an everted shape disposed within arced struts. Such a three dimensional shape may approximate the shape of common vascular defects such as saccular aneurysms. Accordingly, the support structure or expandable body thereof may be formed into a spherical, ovoid or generally globular shape for some embodiments. The struts 512 may be contoured to and forced against an outer surface of the shaping mandrel 574 by a variety of suitable fixtures (not shown).

The three dimensional shape of the strut members 512 and tubular ends determined by the shaping mandrel may be set by heat treatment as is known in the art of vascular implant fabrication. In some embodiments, the support structure 504 may be held by a fixture configured to hold the support structure in a desired shape and heated to about 475-525 degrees C. for about 5-10 minutes to shape-set the structure. For some embodiments, the support structure 504 may be shape set in two or more steps. The final support structure shape may define a generally globular envelop where both the distal and proximal ends lie within the envelope for some embodiments as shown in FIG. 51. In these embodiments, the first and second ends 514 and 516 formed from the tube ends 570 and 572 are inverted or everted so that the substantially solid tubular ends are retracted into the overall globular structure of the arced struts.

Figure 52:
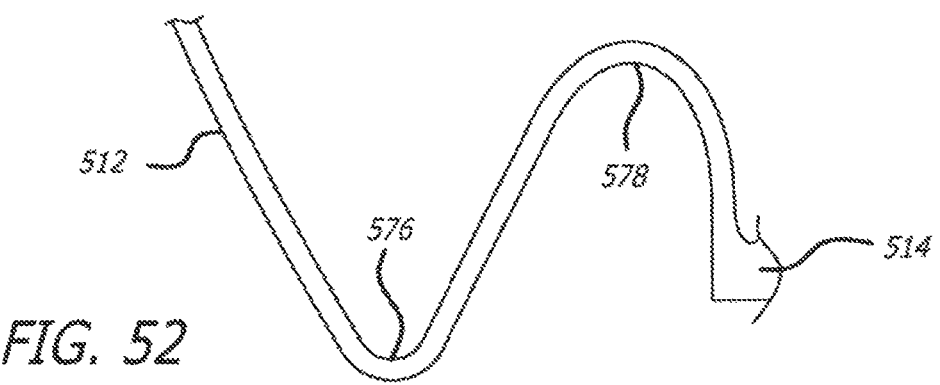
FIG. 52 is an enlarged view of a proximal portion of a strut element of the heat set support structure of FIG. 51.

As shown, the arced portion of the struts 512 may have a sinusoidal-like shape with a first or outer radius 576 and a second or inner radius 578 near a first end of the support structure 504 of the device 500 as shown in FIG. 52. For some embodiments, the first radius 576 and second radius 578 of the support structure 504 may be between about 0.12 mm to about 3 mm. In some embodiments, the outer first radius may be larger than the inner second radius. The ratio of the inner to outer radius may be between about 20% and 60%. For some embodiments, the distance between the first end 514 and second end 516 may be less than about 60% of the overall length of the support structure 504 for some embodiments. A small gap between the rings 514 and 516 at the first end and second end allows for the distal or second end ring 516 to flex downward toward the proximal or first end ring 514 when the device meets resistance at the distal end and thus provides longitudinal conformance. The struts members 512 may be shaped such that there are no portions that are without curvature over a distance of more than about 2 millimeters. Thus, for some embodiments, each strut 512 may have a substantially continuous curvature. This substantially continuous curvature may provide smooth deployment and may reduce the risk of vessel perforation. For some embodiments, the second end 516 may be retracted or everted to a greater extent than the first end 514 such that the second end portion 520 of the support structure or device generally may be more radially conformal than the first end portion. Conformability of a distal or second end portion directed toward the interior of a vascular defect when deployed may provide better device conformance to irregular shaped aneurysms or other vascular defects, such as defects 106 or 210.

Figure 53:
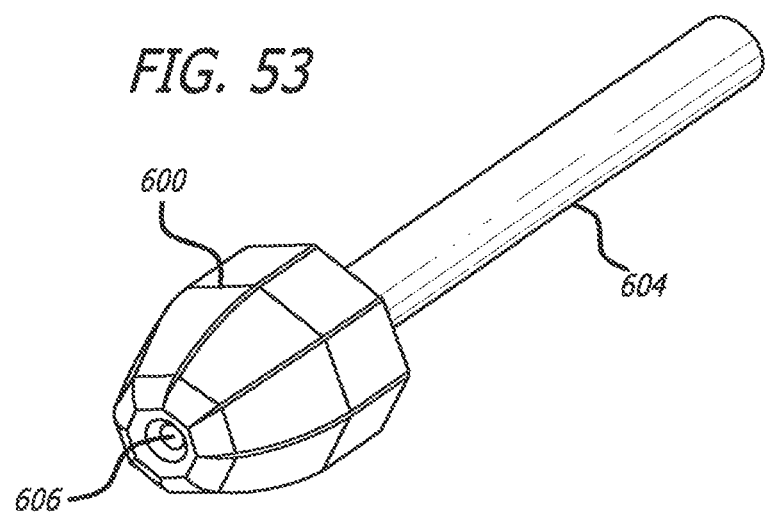
FIG. 53 shows an embodiment of a mandrel that may be used for forming embodiments of defect spanning structures.
Figure 54:
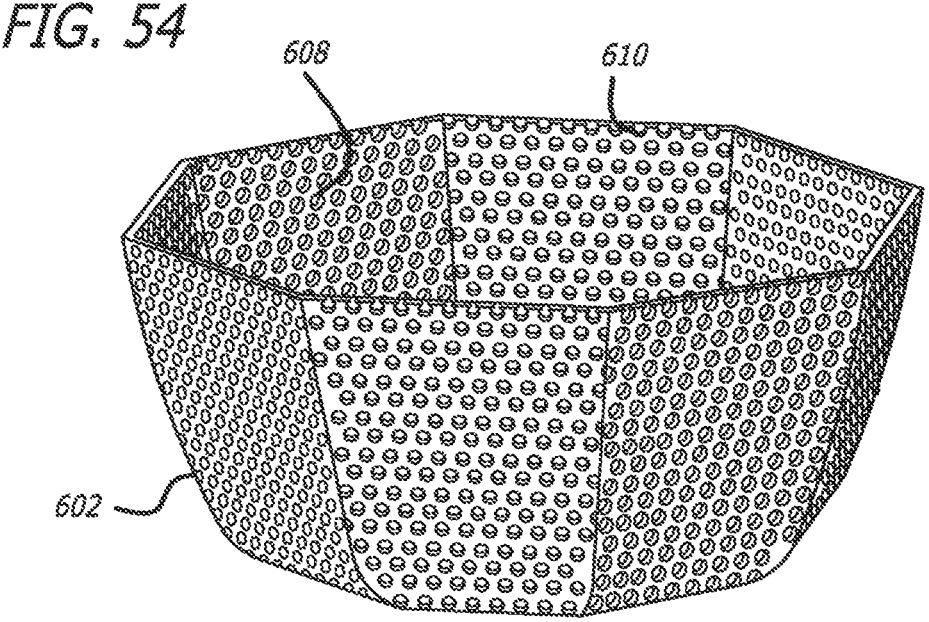
FIG. 54 shows a perspective view of a permeable membrane of a defect spanning structure embodiment.

Some defect spanning structure embodiments for the devices of FIGS. 43, 45, or any other suitable embodiment discussed herein may include a thin metallic film. The metallic film thickness may be between 0.0015 and 0.015 mm in some cases. The thin metallic film may be made by rolling, physical or chemical vapor deposition (PVD or CVD) also known as sputtering and other means known in the art of metallic film fabrication. Sputter depositon of nickel-titanium or nitinol may be done at a low pressure, preferably less than about 10-8 torr. A mandrel 600, made in the shape of the desired film as shown in FIG. 53, may be used as a target for the deposition. Optionally, this same mandrel may be used for dipping, spraying or other processes for the formation of polymeric membranes described herein. The metallic film 602, shown in FIG. 54, may be deposited on to the mandrel 600 and then removed for attachment to a support structure, such as support structure embodiment 542 shown in FIG. 45. The mandrel 600 may have a handle 604 that may be used to hold the mandrel. The mandrel may also have a depression 606 in one end to form a recessed end of the device or expandable body thereof. The mandrel 600 and thus the film 602 formed thereon may have panels 608 so that the film spans a gap between the support structure struts in a substantially straight line. The resulting shape may be somewhat like an umbrella or umbrella-like in shape with panels as shown in FIG. 54. The film 602 may also have holes or perforations 610 disposed therein to provide a desired level of permeability.

Figure 55:
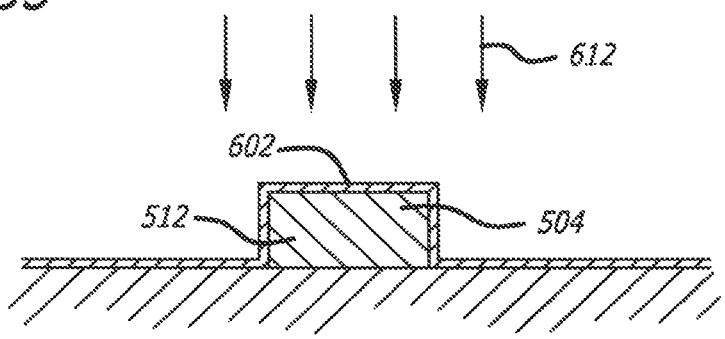
FIG. 55 illustrates a schematic view of a vapor deposition process.

The thin film defect spanning structure 600 may be made at least in part of nitinol. CVD fabrication of thin film nitinol membranes is described by Desatnik et al. in U.S. Patent Application No. US2007/0061006, filed Sep. 14, 2005, titled Methods of Making Shape Memory Films by Chemical Vapor Deposition and Shape Memory Devices Made Thereby, which is incorporated by reference herein in its entirety. Metallic film embodiments may be sputtered on to a mandrel 600 or target that has a temperature greater than about 400° C. as described by Ho et al. in U.S. Pat. No. 6,689,486, filed Oct. 28, 2002, titled Bimorphic, Compositionally-Graded, Sputter-Deposited, Thin Film Shape Memory Device, which is incorporated by reference herein in its entirety. In some embodiments, metallic thin film embodiments may be sputtered directly on to the struts 512 of the support structure 504 by placing the support structure over a mandrel thus eliminating the need to make a separate attachment step. The mandrel 600 may be pivoted or angled within a CVD chamber to coat the sides that are substantially non-orthogonal to the sputter stream 612 as shown in FIG. 55.

Figure 56:
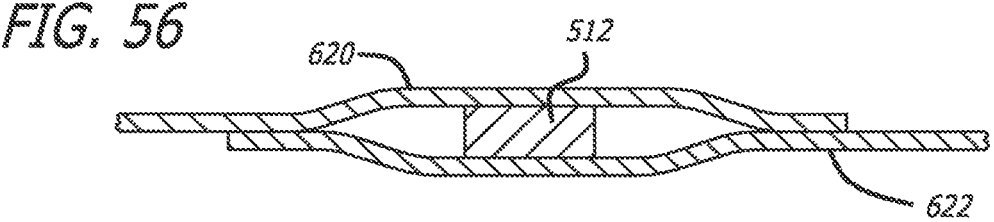
FIG. 56 shows a cross sectional view of a portion of a junction between an embodiment of a defect spanning structure and strut of a support structure.

Some defect spanning structure embodiments may include two or more layers. A two-layer structure may be attached or secured to support structure struts 512 by adhering the two layers to themselves on opposing sides of each strut 512. For example, a first layer 620 may cover an outer surface of at least a portion of a support structure strut 512 and a second layer 622 may cover at least a portion of the inner surface of the strut as shown in the embodiment illustrated in FIG. 56. Thus, the support structure struts 512 may be trapped, captured or otherwise encapsulated by the first and second layers 620 and 622 without being physically bonded or fused to the defect spanning structure. This configuration may be desirable if the support structure 504 is made of a material such as nitinol that may be difficult to bond with other materials. Further, the attachment may be accomplished without significant heating of the support structure. For some embodiments, significant heating of the support structure 504 may have an undesirable affect on its mechanical characteristics.

For some embodiments, a thin permeable membrane may be secured to a support structure embodiment by adhesive bonding using a biocompatible adhesive. Adhesives such as ultraviolet (UV) cured or visible light cured adhesives may be used in some cases. For such embodiments the adhesive bonding process may involve the use of a primer material in order to improve the adherence or bonding process. For some embodiments, a binding agent or primer material may be applied to the support structure or polymer membrane adjacent the support structure prior to applying the adhesive to the membrane or support structure. Some examples of adhesives that may be used to secure the membrane to a support structure include Dymax 1000 series adhesives, Loctite 3200, 3300 and 3900 series adhesives as well as others. Some suitable primer material embodiments may include gamma methacryloxypropyltrimethoxysilane (g-MPTS) a monofunctional silane, vinyltriethoxysilane, bis(3-trimethoxysilyl)propyletylenediamine, tris(3-trimethoxysilylpropyl)isocyanurate, or any other suitable primer material depending on the application and polymer membrane material. Either or both of the adhesive and primers may be applied by spraying, wiping, dipping or any other suitable application technique. For some embodiments, it may be desirable to apply the adhesive, primer or both in a thin even coat prior to the adhesive bonding process.

Figure 57:
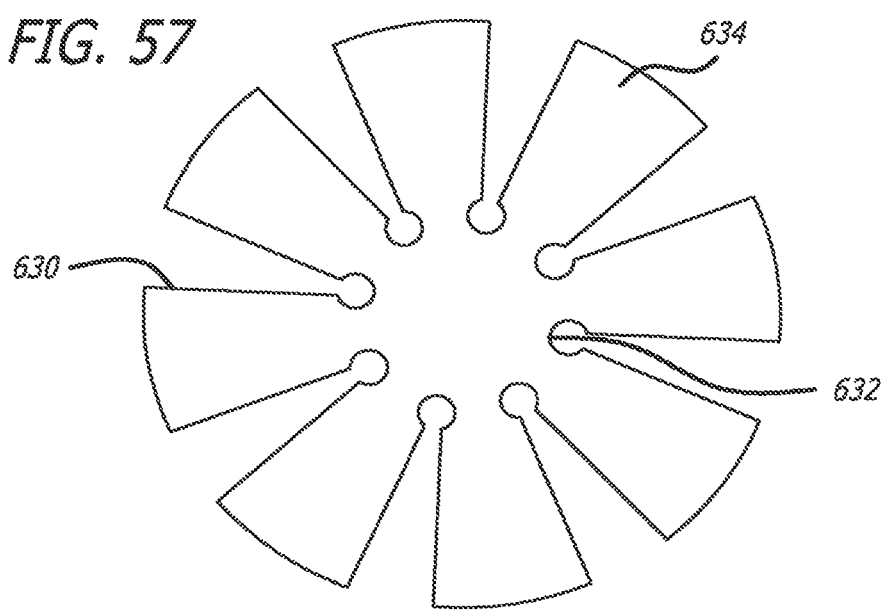
FIG. 57 illustrates an embodiment of a defect spanning structure flat pattern.

In some embodiments, a membrane 630 of a defect spanning structure 502 may be fabricated in a flat pattern from a film or sheet of material and then folded, thermoformed, vacuum-formed or otherwise reshaped to form a desired three dimensional shape approximating the shape of the support structure portion to which it will be secured. For some embodiments, the flat pattern of the membrane 630 may have a central portion 632 that is substantially circular with a plurality of panels 634 that extend radially as shown in FIG. 57. Holes (not shown) may be formed in the flat pattern by laser perforation, mechanical perforation, photochemical etching (PCM) or any other suitable method.

Figure 58:
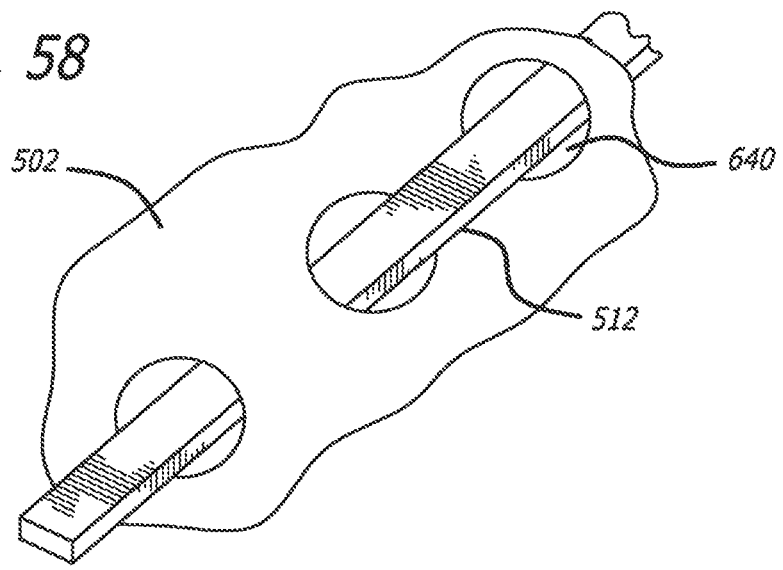
FIG. 58 illustrates a perspective view broken away of an embodiment of a strut engaged with a defect spanning structure membrane.
Figure 59:
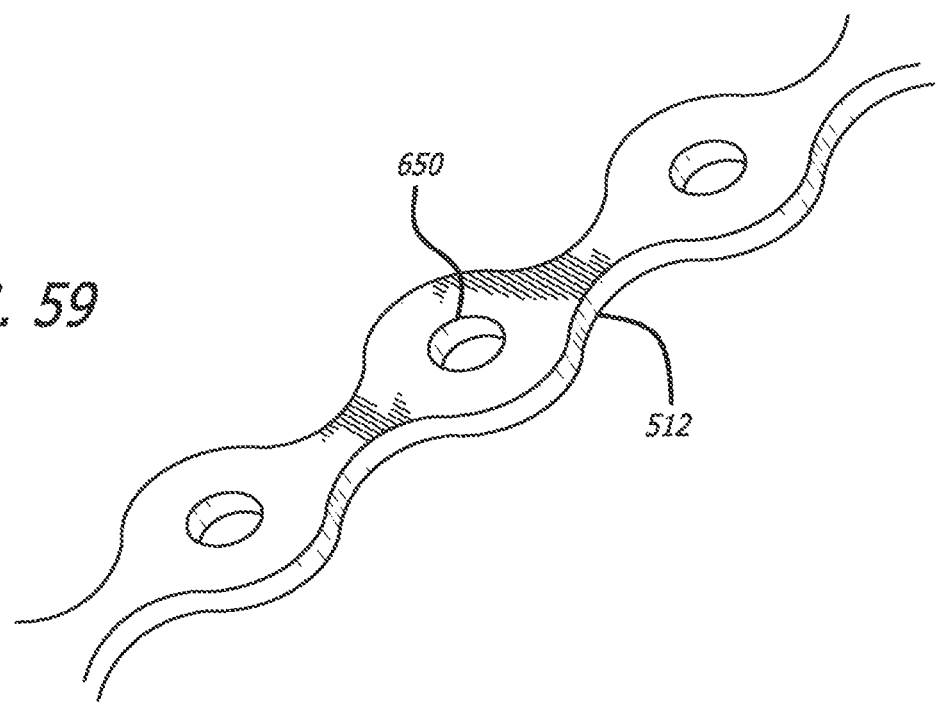
FIG. 59 is a perspective view of a segment of a strut member of a support structure embodiment.

For some embodiments, a defect spanning structure 502 may be fabricated with holes 640 to facilitate attachment to struts 512 or other portions of support structure embodiments. Struts 512 or other projections of the support structure may be threaded through the holes 640, as shown in FIG. 58, so that when the support structure 504 is allowed to expand to its globular configuration, it opens the defect spanning structure 502 with it. As such, a single layer of membrane may be disposed on both sides of the support structure 502. For some embodiments, the support structure struts 512 may have slots, grooves, holes 650 or other features for receiving a portion of the defect spanning structure 502 or otherwise facilitate attachment as shown in FIG. 59.

Figure 60:
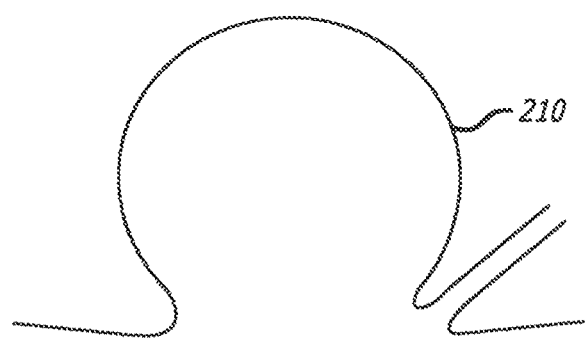
FIGS. 60-63 show a deployment sequence of a device for treatment of a patient's vasculature.
Figure 61:
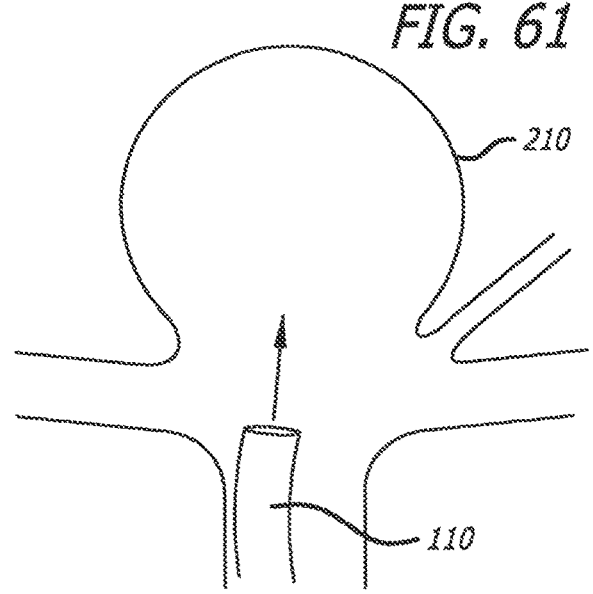

In any of the described embodiments, the device, such as device 540, may be used to treat various vascular defects or sites including blood vessels, cerebral and peripheral aneurysms, fistula and other vascular conditions where occlusion is desired. An example of a terminal aneurysm 210 is shown in FIG. 60 in section. For some deployment embodiments, one or more elongate access instrument(s) such as canula, catheters, guidewires and the like may be use to facilitate placement of the device 540. The tip of a catheter, such as a microcatheter 110 may be advanced into or adjacent the vascular site (e.g., aneurysm 210) as shown in FIG. 61. For some embodiments, an embolic coil or other vaso-occlusive device (not shown) may be placed within the aneurysm 210 to provide a framework for receiving the device 540. In addition, a stent may be placed within a parent vessel of the aneurysm 210 substantially crossing the aneurysm neck prior to or during delivery of devices for treatment of a patient's vasculature discussed herein. For some embodiments, a device 540, attached to an elongate actuator 112 of a delivery apparatus may be inserted within or adjacent an access instrument that may include a micro-catheter 110.

Figure 62:
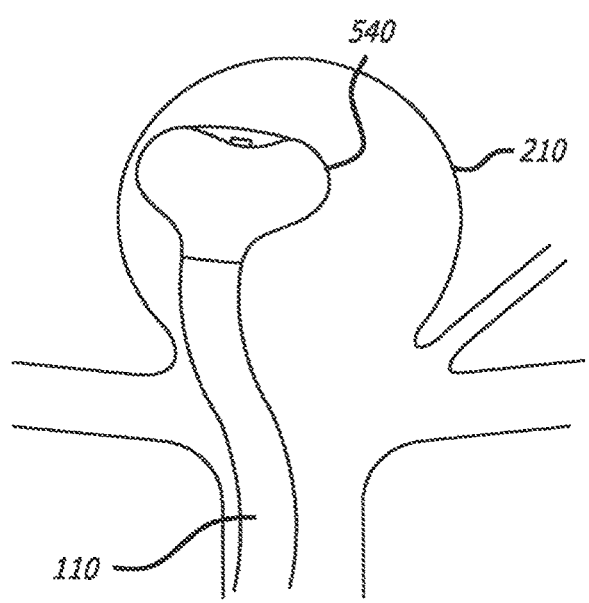
Figure 63:
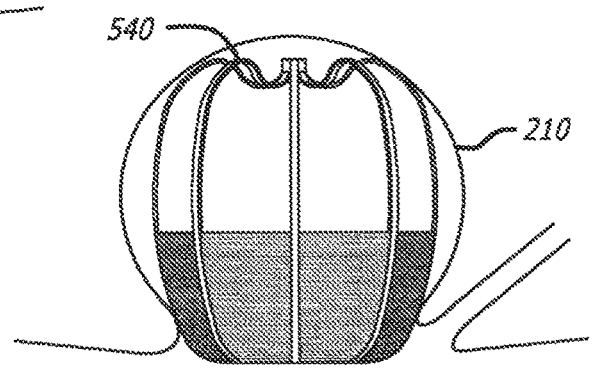
Figure 63:
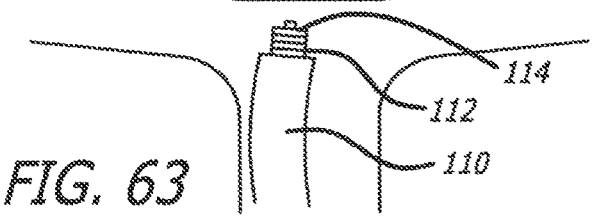

The device 540 may be inserted through a microcatheter 110 such that the catheter lumen restrains radial expansion of the device 540 during delivery. Once the distal tip or deployment port of the delivery system is positioned in a desirable location adjacent or within a vascular defect 210, the device 540 may be deployed out the distal end of the catheter thus allowing the device to begin to radially expand as shown in FIG. 62. As the device 540 emerges from the distal end of the delivery system, the device 540 expands to an expanded state within the vascular site, but may be at least partially constrained by an interior surface of the vascular defect 210. Radial expansion of the device 540 may serve to secure the device within the vascular defect 210 and also deploy the defect spanning structure across at least a portion of an opening (e.g., aneurysm neck) so as to at least partially isolate the vascular defect 210 from flow, pressure or both of the patient's vasculature adjacent the vascular defect as shown in FIG. 63. For some embodiments, once deployed, the defect spanning structure may substantially slow flow into the vascular site.

For some embodiments, the device may be manipulated by the user to position the device within the vascular site during or after deployment. Markers, such as radiopaque markers, on the device or delivery system may be used in conjunction with external imaging equipment (e.g., x-ray) to facilitate positioning of the device or delivery system during deployment. Once the device is properly positioned, the device may be detached by the user. For some embodiments, the detachment of the device from the elongate actuator of the delivery system may be affected by the delivery of energy (e.g., heat, radiofrequency, ultrasound, vibrational, or laser) to a junction or release mechanism between the device and the delivery apparatus. Once the device has been detached, the delivery apparatus may be withdrawn from the patient's vasculature or patient's body. For some embodiments, a stent may be place within the parent vessel substantially crossing the aneurysm neck after delivery of the device.

For some embodiments, a biologically active agent or a passive therapeutic agent may be released from a responsive material component of the device. The agent release may be affected by one or more of the body's environmental parameters or energy may be delivered (from an internal or external source) to the device. Hemostasis may occur within the vascular defect as a result of the isolation of the vascular defect, ultimately leading to clotting and substantial occlusion of the vascular site by a combination of thrombotic material and the device. For some embodiments, thrombosis within the vascular site may be facilitated by agents released from the device and/or drugs or other therapeutic agents delivered to the patient.

Embodiments herein are directed to positioning and delivery of medical devices including methods and devices for the positioning and delivery of devices into luminal organs such as blood vessels. Some embodiments may be used in a variety of luminal body organs or spaces, including embodiments directed to treatment for vascular lesions and defects such as aneurysms. Some embodiments may be particularly useful for vascular navigation and the treatment of vascular defects including aneurysms and more particularly cerebral aneurysms. The devices may also be useful for positioning of a stent that is configured for use at a vessel bifurcation. The apparatus may also find use in the positioning of drug delivery devices so as to allow the delivery of therapeutic agent(s) at a selected site within or about a luminal organ. The devices may also be useful for positioning a needle, cutting element or other surgical instrument at the desired rotational position within a luminal organ. Some delivery system embodiments may be configured for the positioning of medical instrumentation and devices within luminal organs. Some embodiments may be useful for positioning a variety of medical instruments, implants, drug delivery devices and diagnostic devices.

Figure 64:
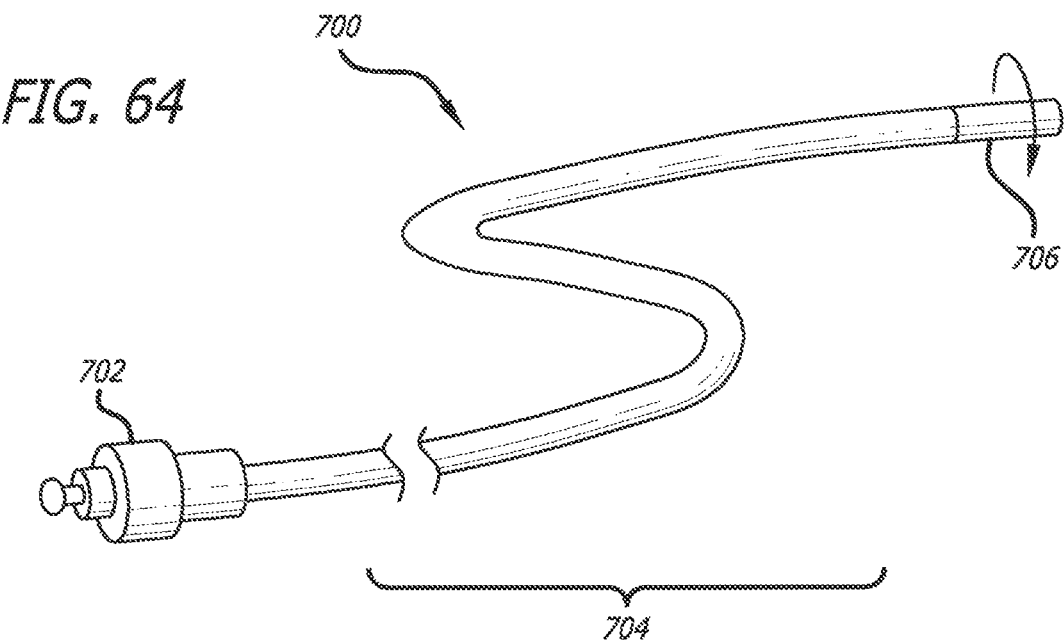
FIG. 64 shows a perspective view of a delivery catheter embodiment.

Referring to FIG. 64, some delivery catheter embodiments 700 include a flexible, elongate member with a proximal end 702 which may include a hub or handle, an intermediate portion or shaft 704 and a rotationally positionable or rotatable distal end 706 that may be configured for use with existing surgical and vascular access catheters, introducers, microcatheters, guidewires, cannula and other elongate medical instruments. In some embodiments, rotation of the rotatable distal end 706 may be accomplished without transmission of torque throughout a length of the apparatus 700 and without rotation of an outer surface of the length or intermediate portion 704 of the delivery catheter 700. For some embodiments, there is no rotation, rotating elements or torque transmission in the intermediate portion 704 between the proximal end 702 the rotatable distal end 706. Thus, rotation of the distal end 706 is accomplished without the transmission of torque along the length of the catheter 700.

Figure 65:
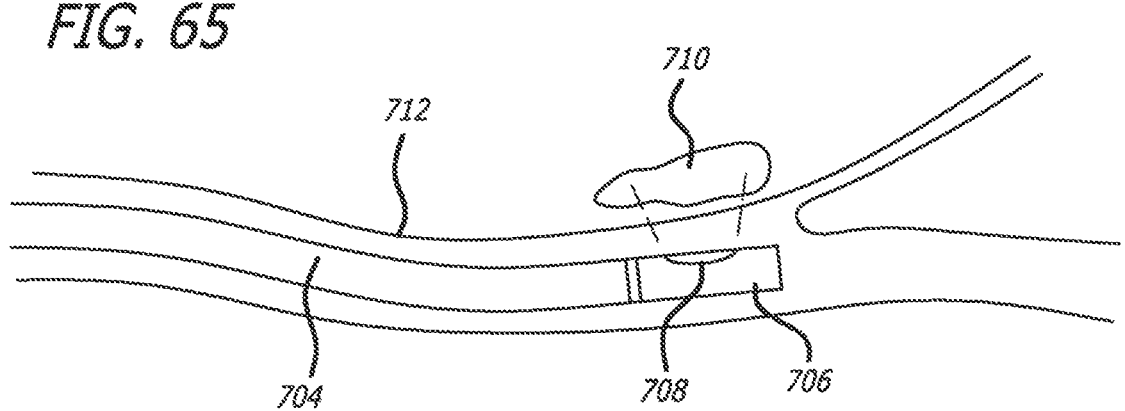
FIG. 65 illustrates a delivery catheter embodiment disposed within a vascular lumen of a patient.

In some embodiments, the catheter 700 may be configured to be advanced through a catheter such as a guide catheter for the rotational positioning of medical devices or instruments within the vasculature for the treatment of focal lesions or defects. The delivery catheter 700 and implant device may be configured to be delivered through the lumen of a microcatheter, known in the art of neurovascular navigation and therapy. Focal lesions or defects such as aneurysms often lie along one side of a blood vessel wall. The rotatable distal end 706 may rotate relative to and substantially independent of the rest of the positioning catheter as shown in FIG. 64. Accordingly, some catheter embodiments may provide a user with the ability to position a medical device with a portion or peripheral region 708 with diagnostic or therapeutic capability in the desired rotation position or circumferential relationship to the target site, lesion or defect 710 of a patient's vasculature 712 as shown in FIG. 65.

The rotatable distal end 706 may be freely rotating like a bearing or it may be driven by another member or mechanism within the apparatus. The drive mechanism may be housed distally near the rotatable distal end 706 or at some position toward the proximal end 702 and connected to the rotatable distal end by a connecting member. For some embodiments, the rotatable distal end 706 may be driven by an electro-mechanical mechanism, electro-magnetic mechanism (e.g., micromotor), push rod and screw mechanism, shape-memory coil mechanism, hydraulic mechanism, multi-layered torque cable mechanism or other flexible torque transmission mechanism. The drive mechanism may allow for slow, continuous rotation or controlled rotation in increments of less than about 45' and more preferably less than about 30'.

Figure 66:
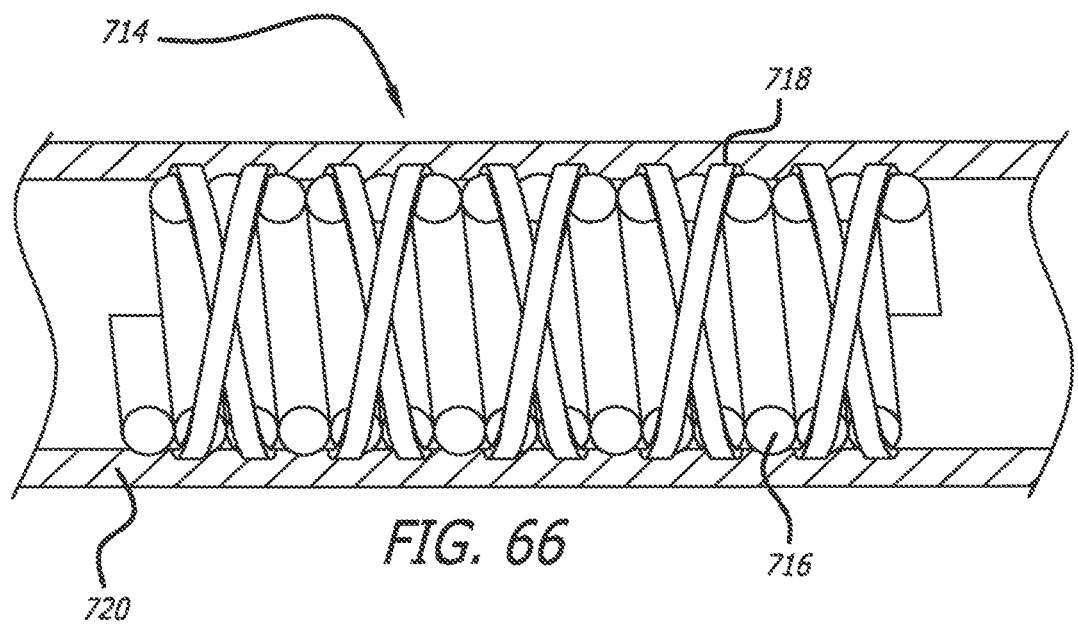
FIG. 66 shows an embodiment of a torque transfer mechanism.

Referring to FIG. 66, for some embodiments, the delivery catheter may include a multi-layered torque cable (MLTC) mechanism 714 for transmission of torsion through the apparatus in a flexible structure. The MLTC mechanism may include one or more tubular layers of coiled or braided wire. The MLTC mechanism may have at least one inner layer 716 and an inner layer comprising a multi-stranded or multifilar structure. In some embodiments, the inner layer 716 includes a coil and the outer layer 718 includes a multi-stranded braid as shown in FIG. 66. An outer polymer layer 720 may also be disposed over the inner and outer layers 716 and 718 of the mechanism 714. Other multi-layered torque cable mechanisms are described in U.S. Pat. No. 5,154,705 to Fleischhacker et al., titled Hollow lumen cable apparatus, filed Jul. 24, 1989 and U.S. Pat. No. 5,165,421 to Fleischhacker et al., titled Hollow lumen cable apparatus, filed Jul. 20, 1990, which are herein incorporated in their entirety by reference.

For some embodiments, the delivery catheter may include a flexible, hollow elongate member (e.g., catheter) with a rotatable distal end member. A medical device that is attached to a flexible, elongate delivery member may be advanced inside the catheter in a substantially co-axial arrangement until the medical device is at least partially within the rotatable distal end member. The delivery catheter may include a transmission member for the transmission of force or energy to the distal end. When force and or energy is delivered through the transmission member, the force or energy is converted to torque which is delivered to the medical device thus rotation of the rotatable distal end of the delivery catheter.

Figure 67:
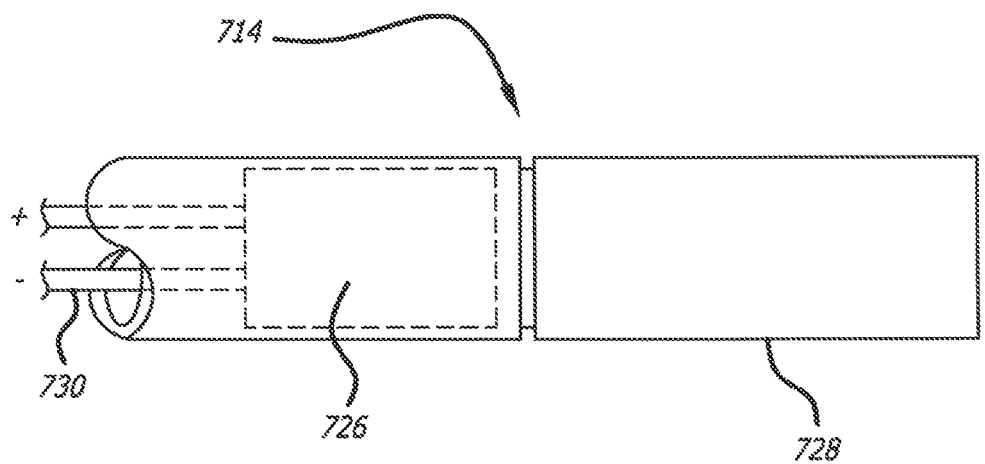
FIG. 67 shows an elevation view of a distal portion of a delivery catheter embodiment.

For some embodiments, a delivery catheter 724 may include a micromotor which is coupled to a rotatable distal end 728 and provided an energy source by energy transmission members such as electrical wires 730 or the like. The micromotor may be part of the proximal hub, shaft or distal end. The micromotor 726 may be at or proximate the distal end 728 as shown in FIG. 67. The micromotor 726 may be fabricated using micro-electromechanical (MEMS) manufacturing techniques and may be electromagnetic, piezoelectric, hydraulic or other type known in the art of micromotors. A MEMS motor may be constructed with an outer ring and reciprocating shuttle similar to that described by Allen et al. in Micromachine Wedge Stepping Motor, 1998 ASME International Mechanical Engineering Congress, Anaheim, Calif. The micromotor may include a lead screw which rotates due to ultrasonic vibrations as described in U.S. Pat. No. 6,940,209 to Henderson, titled Ultrasonic lead screw motor, filed Sep. 8, 2003, which is herein incorporated in its entirety by reference.

For some embodiments, a delivery catheter having a rotatable distal end may include a stored energy member such as a spring. The stored energy member may be a linear spring, torsion spring, or leaf spring. The release of energy stored by the spring may be activated upon retraction of a restraining member that prevents rotation of the rotationally positionable distal. Multiple restraining members may be used to allow several incremental rotations. Alternatively, several springs may be used in combination. In one embodiment, a torsional spring stored energy member is attached to the rotationally positionable distal member. One or more retractable restraining members are positioned to engage the torsional spring member.

Figure 68:
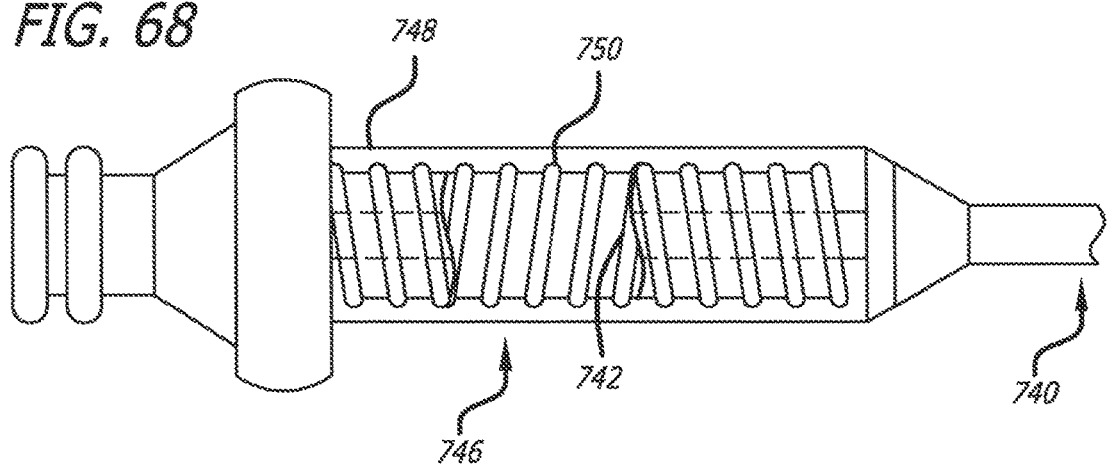
FIG. 68 is an elevation view of a proximal portion of a delivery catheter embodiment.
Figure 69:
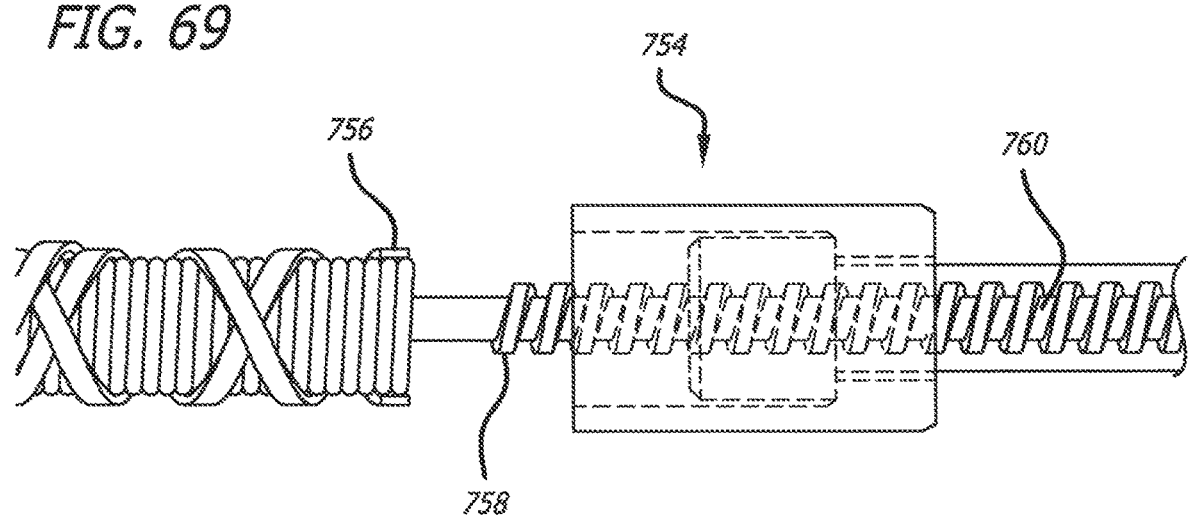
FIG. 69 is an elevation view of a rotation mechanism of a delivery catheter embodiment.

Referring to FIGS. 68-70A, for some embodiments, a delivery catheter having a rotatable distal end 740 may include a push/pull rod 742 and screw mechanism 744 that converts linear force to and/or from rotation force. The threads of the screw mechanism may have a helix angle that is greater than or equal to 45 degrees. The included angle of the teeth may be about 29 degrees to about 60 degrees. For such embodiments, a proximal portion 746 of the mechanism may convert rotation force to linear force at the proximal end thus advancing and retracting a push/pull rod member 742 within a lumen of the elongate delivery apparatus 740. The mechanism may include an internally threaded member 748 and an externally threaded member 750 as shown in FIG. 68. An external rotating member 752 may also be disposed at the proximal portion 746 which is configured to impart relative rotational motion. At the distal end 754 of the delivery catheter 740, the linear force is converted back to rotational force with a similar mechanism thus rotating the rotatable distal member as shown in FIG. 69. As shown in FIG. 69, a flexible outer shaft 756 is disposed about a shaft having an externally threaded member 758 which is coupled to an internally threaded member 760 with the two threaded members in threaded engagement. Thus, torsion is not transmitted through the majority of the apparatus.

Figure 70:
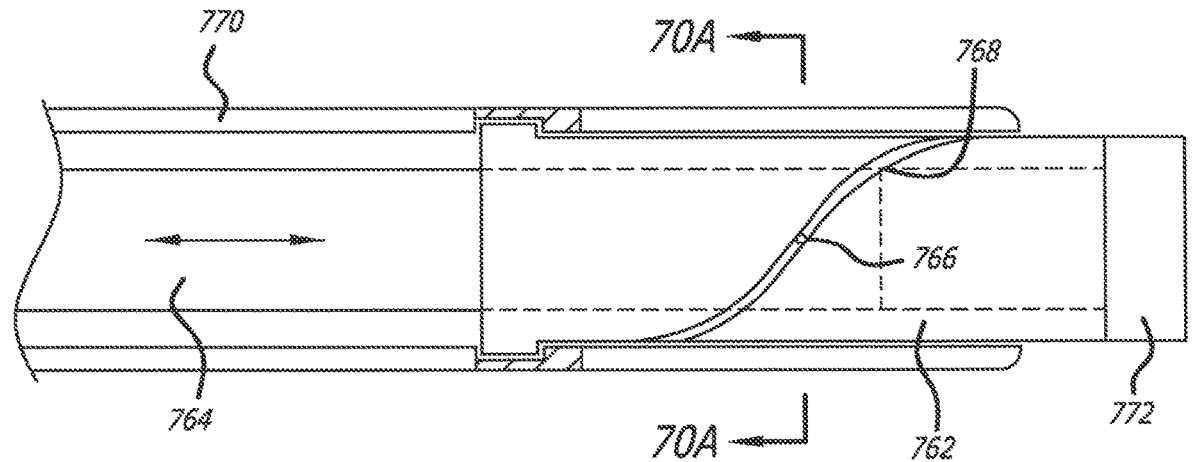
FIG. 70 is an elevation view in partial section of a distal portion of a delivery catheter embodiment.
Figure 70A:
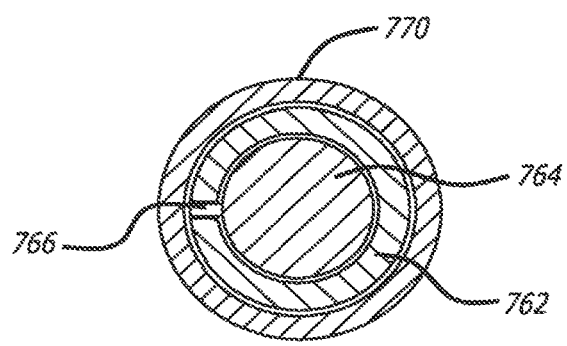
FIG. 70A is a transverse cross section of the embodiment of FIG. 70 taken along lines 70A-70A of FIG. 70.

The conversion of torque may also be accomplished with a slotted tube 762 as shown in FIGS. 70 and 70A. For this embodiment, a push/pull shaft 764 having a radially extending pin 766 is disposed within the rotatable slotted tube 762. The pin 766 is slidingly engaged with the slot 768 of the slotted tube. The slotted tube is configured to be coupled to the shaft 770 of the catheter so as to allow rotation but not axial translation. The push/pull shaft is configured to be axially translated without rotation. Thus, axial translation of the push/pull shaft 764 relative to the rotatable slotted tube 762 generates rotational movement between the slotted tube 762 and the catheter body and push/pull shaft 764. A release mechanism 772 may be disposed at a distal end of the slotted tube 762.

Figure 71:
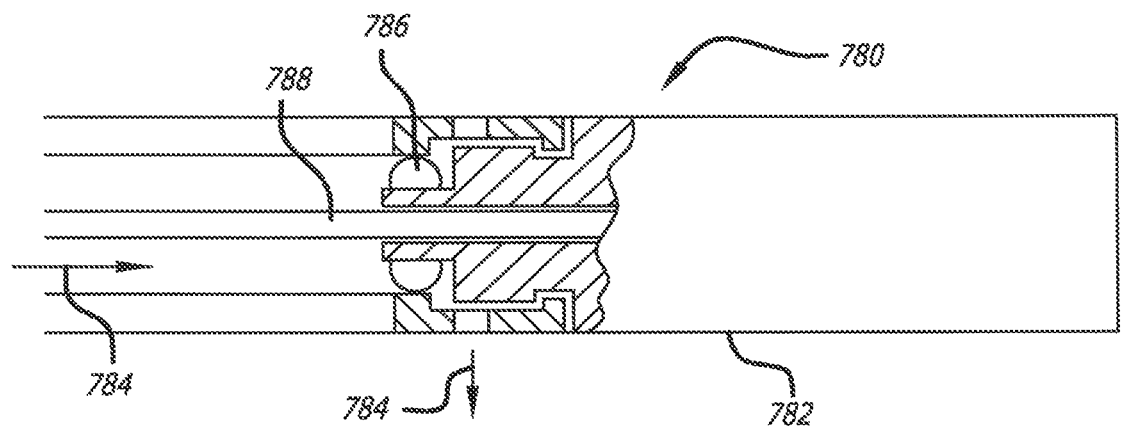
FIG. 71 is an elevation view in partial section of a distal portion of a delivery catheter embodiment.

Referring to FIG. 71, some embodiments, a delivery catheter 780 with a rotatable distal end 782 may include a fluid actuated member or mechanism that rotates in response to a fluid force. The fluid actuated member may be part of or attached to the rotationally positionable distal end. The apparatus also has a fluid path 784 that allows for the injection of a fluid to apply pressure on the fluid actuated member. The fluid actuated member may include one or more surfaces, blades or elements 786 that are angulated relative to the fluid path. The fluid actuated member may include a microturbine for some embodiments. Optionally, the injected fluid also provides lubrication of the rotationally positionable distal end. The injected fluid may be a biocompatible fluid such as sterile saline and may exit the apparatus within the body. Alternatively, the fluid path may describe a closed circuit and the fluid may pass through the fluid actuated member and then return to exit the apparatus outside the body. The term fluid as used herein with regard to the delivery system embodiments should be interpreted broadly as any liquid, gas or emulsion that can readily flow through a small catheter lumen. A push/pull shaft 788 may be secured to a device for treatment of a patient's vasculature disposed at a distal end of the catheter 780.

Figure 72:
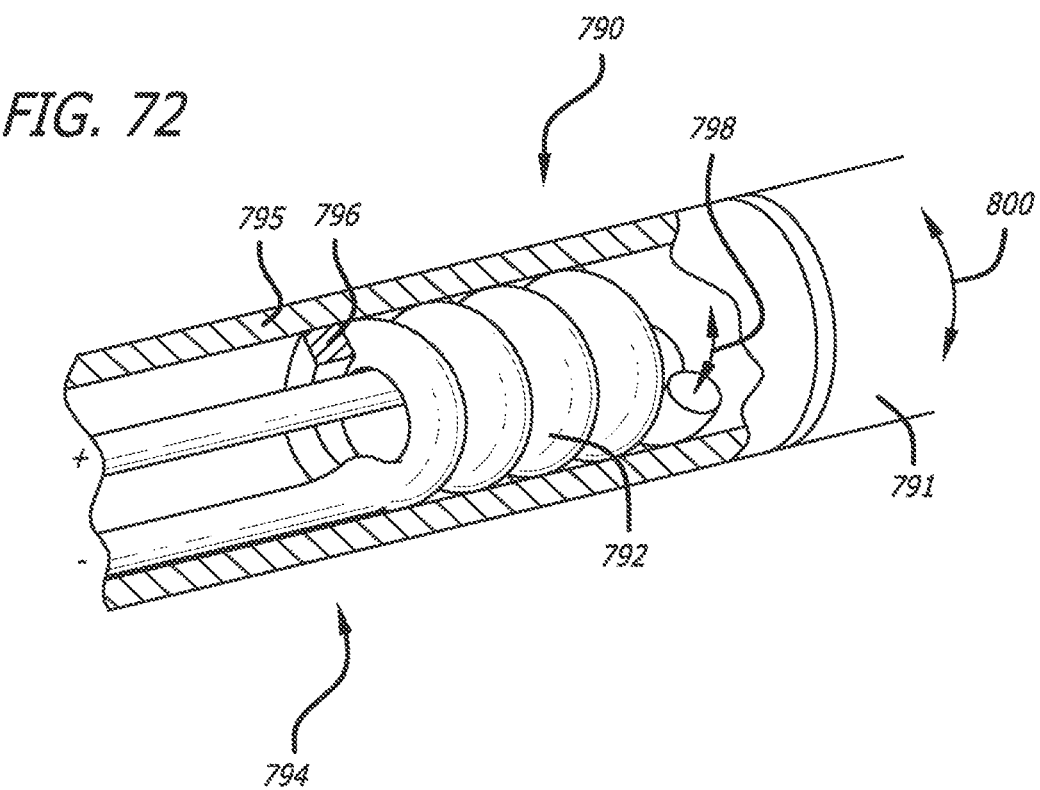
FIG. 72 is a perspective view in partial section of a distal portion of a delivery catheter embodiment.

Referring to FIG. 72, some embodiments of a delivery catheter 790 having a rotatable distal end 791 may include an energy responsive material (ERM) member 792 that responds to the input of energy by increasing or decreasing in length. The ERM member 792 may be configured in a way so that rotation is created when it increases in length. One such configuration is a helix or coil. The ERM coil 792 may be in the distal section 794 of the delivery catheter 790. A second helical or threaded guide member either inside or outside the ERM coil 792 and a restraining member 795 may be used to prevent an expansion ERM coil that would force the ERM coil to rotate. An external coil or internally threaded tube could provide both guide member and restraining member functions. Alternatively, a proximal stop 796 and external restraining tube can force rotation of the coil as shown by arrows 798 in FIG. 72. As energy is delivered to the ERM coil, the ERM coil changes in length and thus is forced to rotate within or about the guide member due to restraint by the restraining member and in turn, rotates the distal end 791 as indicated by arrows 800. The coil of ERM may be made of a nickel-titanium alloy commonly known as Nitinol, shape memory polymers or other ERMs known in the art. The nitinol ERM coil may be heat treated to have an austenite finish temperature (Af) greater than about 25 degrees Celsius. A potentially suitable material is commercially available from Dynalloy, Inc. under the tradename Flexinol®.

The delivery catheter embodiments may include a release mechanism to temporarily retain and or connect to a device such as any of the devices for treatment of a patient's vasculature discussed herein. In addition, the release mechanism may include any of the release mechanism embodiments discussed herein, such as a thermal mechanism, electrolytic mechanism, hydraulic mechanism, shape memory material mechanism, or any other mechanism known in the art of endovascular implant deployment. Some delivery catheter embodiments may be made of various biomaterials known in the art of implant devices including but not limited to polymers, metals, and composites thereof. Suitable polymers include acrylics, polyurethanes, silicones, polypropylene, polyvinyl alcohol, polyesters (e.g., polyethylene terephthalate or PET) and PolyEtherEther Ketone (PEEK). Suitable metals include cobalt-chrome alloys, nickel-titanium alloys (e.g., nitinol), zirconium-based alloys, platinum, stainless steel, titanium, gold, and tungsten. Optionally, the apparatus may comprise wires, fibers or strands that are coiled, woven, or braided as is known in the art of reinforced medical catheters. Optionally, the apparatus may be coated with various polymers to enhance lubricity or other performance characteristics.

In any of the previously described rotatable delivery catheter embodiments, the rotatable distal end member may further comprise a ratcheting mechanism to provide indexing of the rotation and thus greater control over the amount of rotation by the user. The ratcheting mechanism may be at the proximal interface of the rotatable distal end and a flexible elongate member (e.g., catheter) so that as the rotatable distal end rotates, it preferentially seeks discrete rotational positions. The ratcheting mechanism may be configured to provide at least 4 and more preferably at least 6 discrete rotational positions within 360'.

Some method embodiments for positioning medical devices or instruments within luminal organs may include inserting a vascular access apparatus or system including a guidewire, catheter or both to a position proximate a vascular defect. A luminal implant device that is releasably connected to an elongate delivery member having a rotatable distal member may then be disposed within or about the vascular access apparatus. The implant device may be positioned proximate a focal lesion, defect or treatment site and the rotatable distal member and the implant device rotated to achieve a desired angular orientation. The implant device may then be released from the elongate delivery member. For some embodiments, the method may include providing a medical device for treatment of a patient's vasculature having a peripheral region with diagnostic or therapeutic capability attached to a flexible, elongate endoluminal delivery catheter with a proximal end and a rotationally positionable distal end. The method may also include advancing the endoluminal delivery catheter within or about a vascular access device having a catheter, guidewire, or combination thereof. The medical device may then be rotationally positioned such that the peripheral region is positioned adjacent a target site within or about a luminal organ. Some of the method embodiments may further include delivering force or energy through the elongate delivery apparatus or catheter in order to activate an energy responsive material, motor, or mechanism to effect rotation of the rotatable distal member, rotating the implant device within the luminal organ such that a specific portion of its periphery is positioned over or adjacent a lesion, defect or target treatment site, positioning an implant device such that a portion of it spans a blood vessel opening or defect, advancing a push member through a lumen of the elongate delivery apparatus to effect rotation of the rotatable distal member, or heating a portion of the delivery apparatus to effect rotation of the rotatable distal member.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A method of occluding a lumen of a tubular blood vessel, comprising the steps of:
   advancing a distal end of a microcatheter to a region of interest within the tubular blood vessel;
   advancing a device through a lumen of the microcatheter and out of the distal end of the microcatheter by advancing a pusher member such that the device deploys within the lumen of the tubular blood vessel, wherein the device comprises a first hub, a second hub, a support structure having a longitudinal axis, the support structure disposed between the first hub and the second hub, the support structure including a plurality of struts, and a layer of material disposed over the plurality of struts, wherein the first hub is cylindrical and connected to an end of each of the struts of the plurality of struts, wherein the pusher member is detachably coupled to the first hub via a detachment mechanism located within a lumen of the first hub, wherein the support structure has a radially constrained state with an elongated tubular configuration having a transverse dimension, the radially constrained state having a low profile suitable for delivery from the microcatheter, and wherein the support structure expands to an expanded state within the lumen of the tubular blood vessel, the expanded state having a tubular configuration having a first end, a second end, a total length, a longitudinal axis, a smooth outer surface and having an axially shortened configuration relative to the radially constrained state, wherein a first portion of the plurality of struts are in a zig-zag pattern and a second portion of the plurality of struts are straight in the expanded state, and wherein the layer of material spans the expanded state of the support structure from the first hub to a longitudinal position less than the total length of the expanded state; and
   detaching the first hub from the pusher member,
   wherein the longitudinal axis of the expanded state is substantially parallel to a longitudinal axis of the tubular vessel, and wherein the expanded support structure blocks a flow of fluid through the tubular vessel.

2. The method of claim 1, wherein the layer of material comprises at least one of acrylic, silk, silicone, polyvinyl alcohol, polypropylene, polyester, PolyEtherEther Ketone (PEEK), polytetrafluoroethylene (PTFE), polycarbonate urethane (PCU) and polyurethane (PU).

3. The method of claim 1, wherein the layer of material comprises polytetrafluoroethylene (PTFE).

4. The method of claim 1, wherein the support structure is formed from a slotted tubular member.

5. The method of claim 1, wherein the support structure comprises between about 4 struts and about 20 struts.

6. The method of claim 1, wherein the support structure comprises between about 6 struts and about 12 struts.

7. The method of claim 1, wherein the support structure comprises 8 struts.

8. The method of claim 1, wherein 8 struts extend from at least one of the first hub and the second hub.

9. The method of claim 1, wherein the plurality of struts of the support structure in its radially constrained state comprises a circumferential array of struts numbered between about 4 and about 20.

10. The method of claim 1, wherein the plurality of struts of the support structure in its radially constrained state comprises a circumferential array of struts numbered between about 6 and about 12.

11. The method of claim 1, wherein the plurality of struts of the support structure in its radially constrained state comprises a circumferential array of 8 struts.

12. The method of claim 1, wherein at least one of the first or second ends is inverted.

13. The method of claim 1, wherein the plurality of struts includes struts having a transverse cross section including a major transverse dimension disposed circumferentially with respect to the longitudinal axis of the support structure and a minor transverse dimension disposed radially with respect to the longitudinal axis of the support structure.

14. The method of claim 1, wherein the support structure has a three dimensional contour, and wherein the layer of material has a three dimensional configuration that substantially matches at least a portion of the three dimensional contour of the support structure.

15. The method of claim 1, wherein the layer of material is secured to the support structure at least in part by an adhesive.

16. The method of claim 1, wherein the layer of material includes pores.

17. The method of claim 1, wherein the expanded state of the support structure is a heat-formed three-dimensional shape.

18. The method of claim 1, wherein the layer of material is stretched between adjacent struts of the plurality of struts when the support structure is in the expanded state.

19. The method of claim 1, wherein each strut of the plurality of struts extends from the first hub to the second hub.

20. The method of claim 1, wherein the expanded support structure does not block a flow of fluid through a saccular cavity.

21. The method of claim 20, wherein the saccular cavity is an aneurysm.

22. The method of claim 1, wherein the detachment mechanism is selected from a group consisting of a mechanical detachment mechanism, a thermal detachment mechanism and a electrolytic detachment mechanism.

23. The method of claim 1, wherein a distal end of the device has a substantially closed configuration.

24. The method of claim 1, wherein the second portion of the plurality of struts has a tapered configuration.

* * * * *